(12) United States Patent
Rogers et al.

(10) Patent No.: US 11,365,410 B2
(45) Date of Patent: Jun. 21, 2022

(54) PRODUCTION AND MONITORING OF METABOLITES IN CELLS

(71) Applicant: President and Fellows of Harvard College, Cambridge, MA (US)

(72) Inventors: Jameson K. Rogers, Boston, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 738 days.

(21) Appl. No.: 15/566,040

(22) PCT Filed: Apr. 12, 2016

(86) PCT No.: PCT/US2016/027106
§ 371 (c)(1),
(2) Date: Oct. 12, 2017

(87) PCT Pub. No.: WO2016/168182
PCT Pub. Date: Oct. 20, 2016

(65) Prior Publication Data
US 2018/0127746 A1    May 10, 2018

Related U.S. Application Data

(60) Provisional application No. 62/146,478, filed on Apr. 13, 2015.

(51) Int. Cl.
C12N 15/10     (2006.01)
C12P 19/02     (2006.01)
C07K 14/00     (2006.01)

(52) U.S. Cl.
CPC .......... *C12N 15/1086* (2013.01); *C07K 14/00* (2013.01); *C12N 15/10* (2013.01); *C12P 19/02* (2013.01)

(58) Field of Classification Search
CPC ............................ C12N 15/1086; C12P 19/02
See application file for complete search history.

(56) References Cited

U.S. PATENT DOCUMENTS

2013/0310458 A1   11/2013  Eggeling et al.
2014/0342414 A1   11/2014  Valle et al.

FOREIGN PATENT DOCUMENTS

DE    10 2010 019 059 A1    11/2011
JP    2010-533483 A          10/2010
JP    2013-529073 A           7/2013
JP    2014-511697 A           5/2014
WO    2014/158594 A1         10/2014

OTHER PUBLICATIONS

Kolin et al. (J. Bacteriol., 189 (1) (2007), 269-271) (Year: 2007).*
Möhrle et al. (Anal. Bioanal. Chem., 2007, 388:1117-1125) (Year: 2007).*
Tang et al. (Angew. Chem. Int. Ed. 2011, 50, 1084-1086) (Year: 2011).*

(Continued)

*Primary Examiner* — Jeremy C Flinders
(74) *Attorney, Agent, or Firm* — Banner & Witcoff, Ltd.

(57) ABSTRACT

Methods of making and monitoring metabolites in cells are provided.

10 Claims, 28 Drawing Sheets

Specification includes a Sequence Listing.

(56) References Cited

OTHER PUBLICATIONS

Martineau et al. (Biosensors and Bioelectronics, 2009, 25:759-766) (Year: 2009).*

Extended European Search Report of European Application No. 16780558.9 dated Jul. 26, 2018.

Rogers, Jameson K. et al., "Biosensor-based engineering of biosynthetic pathways", Current Opinion in Biotechnology, London, GB, vol. 42, Mar. 18, 2016 (Mar. 18, 2016), pp. 84-91, XP029831138, ISSN: 0958-1669, DOI: 10.1016/J. COPBIO.2016.03.005.

Rogers, Jameson K. et al., "Genetically encoded sensors enable real-time observation of metabolite production", Proceedings of the National Academy of Sciences, vol. 113, No. 9, Feb. 8, 2016 (Feb. 8, 2016), pp. 2388-2393, XP055492813, US. ISSN: 0027-8424, DOI: 10.1073/pnas.1600375113.

Rogers, Jameson K. et al., "Multiplexed Engineering in Biology" Trends in Biotechnology, ELSEVIER Publications, Cambridge, GB, vol. 34, No. 3, Feb. 17, 2016 (Feb. 17, 2016), pp. 198-206, XP029421400, ISSN: 0167-7799, DOI: 10.1016/J.TIBTECH.2015.12.004.

Rogers, Jameson K. et al., "Synthetic biosensors precise gene control and real-time monitoring of metabolites", Nucleic Acids Research, vol. 43, No. 15, Jul. 7, 2015 (Jul. 7, 2015), pp. 7648-7660, XP055492816, ISSN: 0305-1048, DOI: 10.1093/nar/gkv616.

Taylor, Noah D. et al., "Engineering an allosteric transcription factor to respond to new ligands", Nature Methods, vol. 13, No. 2, Feb. 1, 2016 (Feb. 1, 2016), pp. 177-183, XP055469782, New York ISSN: 1548-7091, DOI: 10.1038/nmeth.3696.

Yang, Jina et al., "Synthetic RNA devices to expedite the evolution of metabolite-producing microbes". Nature Communications, vol. 4, Jan. 29, 2013 (Jan. 29, 2013), p. 1413, XP055130450, DOI: 10.1038/ncomms2404.

Sullivan et al., "Unusual Regulation of a Leaderless Operon Involved in the Catabolism of Dimethylsulfoniopropionate in Rhodobacter sphaeroides," PLoS One, vol. 6, Issue 1, e15972, pp. 1-11 (Jan. 2011).

Palacios et al., "2-Methylcitrate-dependent actibation of the propionate catabolic operon (prpBCDE) of *Salmonella enterica* by the PrpR protein," Microbiology, vol. 150, No. 11, pp. 3877-3887 (2004).

Rathnasingh et al., "Production of 3-hydroxypropionic acid via malonyl-CoA pathway using recombinant *Escherichia coli* strains," Journal of Biotechnology, vol. 157, No. 4, pp. 633-640 (Feb. 20, 2012).

Raman et al. Evolution-guided optimization of biosynthetic pathways. Proc. Natl. Acad. Sci. Dec. 1, 2014 (Jan. 12, 2014) vol. 111 Issue 50 pp. 17803-17808.

Van Sint Fiet et al. "Selection of biocatalysts for chemical synthesis" Proc. Natl Acad. Sci. 07 Feb. 1, 2006 (Jul. 2, 2006), vol. 103, Issue 6 pp. 1696-1698.

Dec. 8, 2020—(JP) Decision of Refusal—App. No. 2017-553949.

* cited by examiner 3-hydroxypropionate biosynthesis and sensing

PRODUCTION AND MONITORING OF METABOLITES IN CELLS

RELATED APPLICATIONS

This application is a National Stage Application under 35 U.S.C. 371 of PCT application PCT/US16/27106 designating the United States and filed Apr. 12, 2016; which claims the benefit of Provisional application No. 62/146,478 and filed Apr. 13, 2015 each of which are hereby incorporated by reference in their entireties.

STATEMENT OF GOVERNMENT INTERESTS

This invention was made with government support under DE-FG02-02ER63445 awarded by the U.S. Department of Energy. The government has certain rights in the invention.

FIELD

The present invention relates in general to genetically modified bacteria and methods of detecting metabolite production in genetically modified bacteria.

BACKGROUND

Small molecule inducible systems are genetically encoded biosensors that modulate gene expression in response to the presence of a small molecule inducer. One of the most widely used biosensors is the allosteric DNA binding protein LacI, which natively regulates the lactose catabolism operon in $E.\ coli$ by binding near the transcriptional start site and repressing transcription initiation. When an inducing molecule such as isopropyl β-D-1-thiogalactopyranoside (IPTG) is present in the cell, it binds to the LacI protein and the LacI-IPTG complex disassociates from DNA, allowing transcription to proceed. Construction and characterization of engineered LacI-inducible systems has resulted in widespread use in applications ranging from protein overexpression, to signal processing, and even chromosomal visualization.

Because of their general applicability and extensive characterization, a small set of canonical inducible regulators (LacI, TetR, AraC, LuxR) are repeatedly used for a diverse range of applications. Other well-characterized inducible systems are available (PrpR, RhaRS, CymR, XylS), but with the exception of CymR, these suffer from catabolite repression and/or weak induction. Other expression control paradigms include riboswitches, which provide ligand-mediated control of translation, and light-regulated optogenetic systems, which are a complement to chemical induction.

SUMMARY

Embodiments of the present disclosure are directed to methods of identifying a bacterial strain that is optimized for production of a metabolite from a population of bacterial strains. The methods described herein can be used to quickly identify the best strains for chemical production out of millions of less effective strains. Embodiments described herein are intended to be applicable to a broad range of chemicals that can be synthesized by microorganisms having their genomes genetically modified to include the synthetic pathway for a desired chemical.

According to one aspect, the genome of a microorganism is genetically modified to include a DNA sequence, such as a synthetic or foreign DNA sequence, encoding a metabolite binding molecule (which may be referred to herein as a "sensor" to the extent that the metabolite binding molecule binds to the metabolite and "senses" the presence of the metabolite directly or indirectly). As DNA is included or inserted into the genome of the microorganism, the resulting microorganism may be referred to as a recombinant microorganism. According to one aspect, the sensor or metabolite binding molecule is an allosteric biomolecule that undergoes a conformation change upon binding a desired chemical or metabolite resulting in a change in gene regulation. Sensors and their corresponding binding partners are known to those of skill in the art and include allosteric molecules such as transcription factors (which bind to DNA to regulate expression of the bound DNA sequence), riboswitches, two-component signaling proteins and nuclear hormone receptors.

The genome of the microorganism is also genetically modified to include DNA encoding for a detectable molecule or reporter, such as a fluorescent compound, protein or molecule. When expressed, the sensor regulates the production of the reporter within the microorganism. Depending on the nature of the sensor, it can regulate reporter production by repressing in the absence of the metabolite, activating in the presence of the metabolite, occluding ribosome binding site in the absence of metabolite etc., and other methods known to those of skill in the art. If the reporter, such as a fluorescent molecule, is produced within the microorganism, it can be detected by methods known to those of skill in the art. According to one aspect, the level of fluorescence is proportional to the amount of metabolite produced. The level of fluorescence can be detected in real-time to provide an indication of the amount of metabolite produced over time.

According to one aspect, metabolite production is a function of fluorescence which can be detected in real-time and monitored over time to determine increase and decrease of fluorescence. Accordingly, an optimal fluorescence can be detected to allow the separation and isolation of cells which produce desirable amounts of the metabolite from cells which produce reduced amounts or undesirable amounts of metabolite. According to one aspect, a method is provided for determining the optimum, desirable timing for separating cells within a population which produce a desirable amount of metabolite from cells within the population which produce an undesirable amount of metabolite or no metabolite. Enzymes and cellular processes within the separated cells can then be identified and used in cells (i.e., same or different species of cells) or in cell-free systems such as immobilized enzyme reactors, to produce desirable amounts of metabolite.

The microorganism has also been genetically modified to include DNA encoding genes to produce a metabolite which is a binding partner of the sensor. Alternatively, endogenous genes in the microbe can produce the metabolite. The metabolite is a target chemical desired to be produced by the microorganism. The sensor which can be a DNA binding molecule will bind to the metabolite, when expressed. In this manner, the genetically modified microorganism can sense its own level of chemical production insofar as the sensor can sense for the presence within the microorganism of the metabolite. When the metabolite is produced by the cell, the metabolite binds to the sensor in a manner to regulate the reporter gene and, as a result, the reporter is produced by the microorganism proportional to the amount of metabolite binding partner produced by the microorganism.

According to one aspect, a selected strain is subjected to genetic modification intended to optimize metabolite production by diversifying the population of microorganisms with a large number of semi-random chemical production designs, typically on the order of a billion. A genetically modified strain can be screened for its ability to produce the reporter and therefore the metabolite. Cells within a population producing desirable amounts of the metabolite as determined by detection of the reporter can be selected, isolated and grown to produce a population of cells (subpopulation of the original population) with desirable metabolite production. A selected strain can be subjected to repeated rounds of genetic modification and screening to produce a strain with optimized metabolite production. Accordingly, an additional aspect includes identifying a strain that is optimized for production of the metabolite by identifying strains that produce increased amount of the reporter.

According to one aspect, a method of selecting a subset of microorganisms for the production of a metabolite is provided wherein the population of microorganisms has been genetically modified to include exogenous or foreign DNA encoding for a reporter molecule, wherein the population of microorganisms has been genetically modified to include exogenous or foreign DNA encoding a sensor which when expressed regulates production of the reporter molecule by the microorganisms, wherein the population of microorganisms has been genetically modified to include exogenous or foreign DNA encoding pathway genes for a metabolite binding partner of the sensor or which may already include DNA encoding pathway genes to a metabolite binding partner, which when expressed binds to the DNA binding molecule to induce production of the reporter molecule in a manner dependent on the concentration of the expressed metabolite, and selecting a subset of microorganisms that produce sufficient metabolite based on detection of the reporter.

According to one aspect, the sensor is a transcription factor, riboswitch, two-component signaling protein or a nuclear hormone receptor.

According to one aspect, the binding of the metabolite to the sensor activates gene expression to induce production of the reporter in a manner dependent on the concentration of the expressed metabolite.

According to one aspect, binding of the metabolite to the DNA binding protein represses gene expression to induce production of the reporter in a manner dependent on the concentration of the expressed metabolite.

According to one aspect, the step of genetically modifying the subset of microorganisms to alter genes that produce the metabolite includes multiplexed automated genome engineering.

According to one aspect, a method is providing for selecting a subset of microorganisms for the production of a metabolite, wherein the population of microorganisms have been genetically modified to include exogenous or foreign DNA encoding for a reporter, wherein the population of microorganisms have been genetically modified to include exogenous or foreign DNA encoding a sensor which when expressed regulates production of the reporter by the microorganisms, wherein the population of microorganisms may or may not have been genetically modified to include pathway genes to produce a metabolite binding partner of the sensor, which when expressed binds to the sensor to induce production of the reporter in a manner dependent on the concentration of the expressed metabolite, screening the microorganisms based on detection of the reporter, repeatedly genetically modifying the microorganisms to alter genes that produce the metabolite and screening the microorganisms based on detection of the reporter, to result in a desired pool of microorganisms.

According to one aspect, a method of selecting a subset of microbes for the production of a metabolite is provided which includes providing a population of microbes, wherein the population of microbes has been genetically modified to include exogenous DNA encoding for a reporter, wherein the population of microbes has been genetically modified to include exogenous DNA encoding a sensor biomolecule which when expressed regulates expression of the reporter by the microbes, wherein the population of microbes has been genetically modified to include exogenous DNA encoding genes to produce a metabolite binding partner of the sensor, and wherein the microbes produce the metabolite binding partner which binds to the sensor to induce expression of the reporter in a manner dependent on the concentration of the produced metabolite, and screening the population of microbes by detecting the reporter to identify a subset of microbes. According to one aspect, the reporter is a fluorescent protein. According to one aspect, the screening is carried out by fluorescence activated cell sorting. According to one aspect, the sensor biomolecule and the metabolite binding partner are member pairs known to those of skill in the art. According to one aspect, the method further includes genetically modifying the subset of microbes to alter genes that affect production of the metabolite directly or indirectly, and screening the subset of microbes by detecting the reporter to identify a subsequent subset of microbes.

According to one aspect, a method of modifying a microbe to include a sensor biomolecule corresponding to a metabolite is provided including genetically modifying the microbe to include exogenous DNA encoding the sensor biomolecule that regulates expression by the microbe of a gene encoding a protein, genetically modifying the microbe to include exogenous DNA encoding genes to produce the metabolite corresponding to the sensor, and wherein the microbes produce the metabolite which binds to the sensor to induce expression of the protein in a manner dependent on the concentration of the produced metabolite, and wherein the sensor is AcuR and the metabolite is acrylate or wherein the sensor is ttgR and the metabolite is phenol. According to one aspect, the microbe is genetically modified to include exogenous DNA encoding for the protein. According to one aspect, the protein is a fluorescent protein. According to one aspect, the protein is an antidote to a toxin.

According to one aspect, a microbe is provided wherein the microbe is genetically modified to include exogenous DNA encoding a sensor biomolecule that regulates expression by the microbe of a gene encoding a protein, and wherein the microbe is genetically modified to include exogenous DNA encoding genes to produce a metabolite, and wherein the microbe produces the metabolite which binds to the sensor biomolecule to induce expression of the protein in a manner dependent on the concentration of the produced acrylate, and wherein the sensor is AcuR and the metabolite is acrylate or wherein the sensor is ttgR and the metabolite is phenol. According to one aspect, the microbe is genetically modified to include exogenous DNA encoding for the protein. According to one aspect, the protein is a fluorescent protein. According to one aspect, the protein is an antidote to a toxin.

According to one aspect, a method of modifying a microbe to include a sensor biomolecule corresponding to a metabolite is provided including genetically modifying the microbe to include exogenous DNA encoding a prpR sensor biomolecule that regulates expression by the microbe of a gene encoding a protein, genetically modifying the microbe to include exogenous DNA encoding genes to produce 3-hydroxypropionate and to transformed 3-hydroxypropionate into 2-methylcitrate, and wherein the microbes produce the 2-methylcitrate which binds to the prpR sensor to induce expression of the protein in a manner dependent on the concentration of the 2-methylcitrate. According to one aspect, the microbe is genetically modified to include exogenous DNA encoding for the protein. According to one aspect, the protein is a fluorescent protein. According to one aspect, the protein is an antidote to a toxin.

According to one aspect, a microbe is provided wherein the microbe is genetically modified to include exogenous DNA encoding a prpR sensor biomolecule that regulates expression by the microbe of a gene encoding a protein, and wherein the microbe is genetically modified to include exogenous DNA encoding genes to produce 3-hydroxypropionate and to transformed 3-hydroxypropionate into 2-methylcitrate, and wherein the microbe produces the 2-methylcitrate which binds to the prpR sensor biomolecule to induce expression of the protein in a manner dependent on the concentration of the produced 2-methylcitrate. According to one aspect, the microbe is genetically modified to include exogenous DNA encoding for the protein. According to one aspect, the protein is a fluorescent protein. According to one aspect, the protein is an antidote to a toxin.

According to one aspect, a method of modifying a microbe to include a sensor biomolecule corresponding to a metabolite is provided including genetically modifying the microbe to include exogenous DNA encoding an acuR sensor biomolecule that regulates expression by the microbe of a gene encoding a protein, genetically modifying the microbe to include exogenous DNA encoding genes to produce 3-hydroxypropionate and to transformed 3-hydroxypropionate into acrylate, and wherein the microbes produce the acrylate which binds to the acuR sensor to induce expression of the protein in a manner dependent on the concentration of the acrylate. According to one aspect, the microbe is genetically modified to include exogenous DNA encoding for the protein. According to one aspect, the protein is a fluorescent protein. According to one aspect, the protein is an antidote to a toxin.

According to one aspect, a microbe is provided wherein the microbe is genetically modified to include exogenous DNA encoding an acuR sensor biomolecule that regulates expression by the microbe of a gene encoding a protein, and wherein the microbe is genetically modified to include exogenous DNA encoding genes to produce 3-hydroxypropionate and to transformed 3-hydroxypropionate into acrylate, and wherein the microbe produces the acrylate which binds to the acuR sensor biomolecule to induce expression of the protein in a manner dependent on the concentration of the produced acrylate. According to one aspect, the microbe is genetically modified to include exogenous DNA encoding for the protein. According to one aspect, the protein is a fluorescent protein. According to one aspect, the protein is an antidote to a toxin.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which.

Acrylate and anhydrotetracycline (aTC) increase in 2-fold increments while arabinose, glucarate, erythromycin and naringenin increase in 3-fold increments. The inducing chemical and biosensor name are indicated to the left and right of the table, respectively. The gray band is the fluorescent response of a control strain containing no fluorescent reporter. Fluorescence measurements are performed 15 hours after addition of the inducing chemicals.

Figure 2:
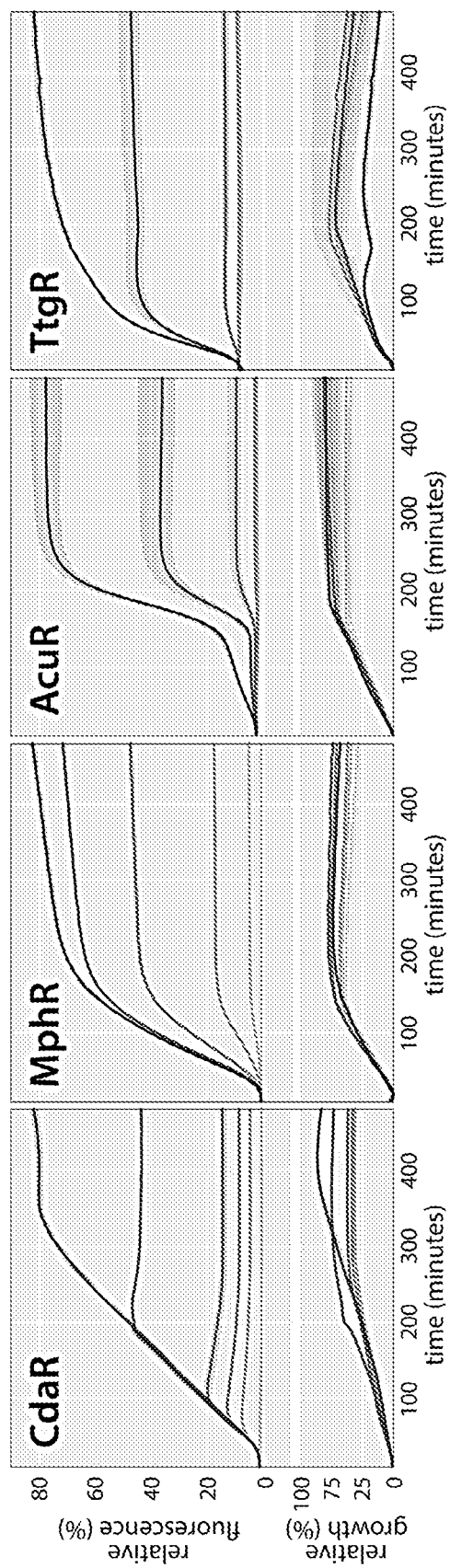

FIG. 2 depicts induction and growth kinetics for the low-copy glucarate (CdaR), erythromycin (MphR), acrylate (AcuR) and naringenin (TtgR) biosensors. Chemical inducers are added at time zero and fluorescence is observed for eight hours. Lower panels show the optical density of the induced cultures over time. Induction levels are indicated by shade, with darker colors indicating higher inducer concentrations. Glucarate induction levels are 40 mM, 13 mM, 4.4 mM, 1.5 mM, 0.49 mM and no inducer addition. Erythromycin induction levels are 1400 µM, 450 µM, 150 µM, 51 µM, 17 µM and no inducer addition. Acrylate induction levels are 5 mM, 2.5 mM, 1.3 mM, 0.63 mM, 0.31 mM and no inducer addition. Naringenin induction levels are 9 mM, 3 mM, 0.33 mM, 0.11 mM, 0.037 mM and no inducer addition. Fluorescence and optical density are normalized as described herein. The standard error of the mean is represented with a 95% confidence interval (n=3).

Figure 3:
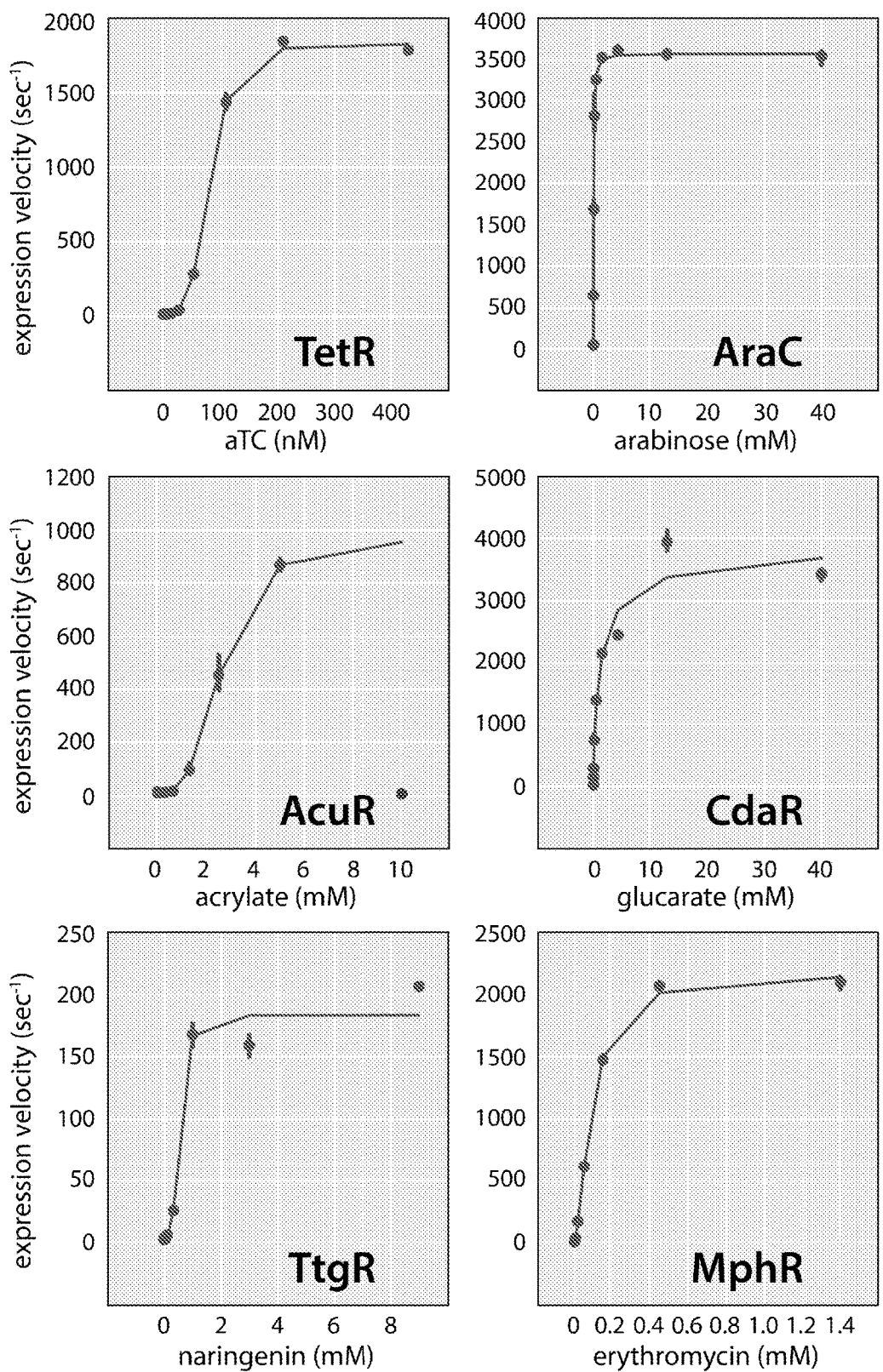

FIG. 3 depicts high-copy promoter activity fit to a model of inducible gene expression. The maximum expression velocity of each inducible promoter was determined at various levels of induction (points). The data was fit to a Hill function modified to account for basal and maximal promoter activity (green lines). The anhydrotetracycline (TetR), acrylate (AcuR) and naringenin (TtgR) biosensors all show high induction cooperativity. The arabinose (AraC), glucarate (CdaR) and erythromycin (MphR) biosensors show low or moderate levels of cooperativity. The 10 mM acrylate induction condition was omitted from the modeling data due to high toxicity (red point). Error bars reflect the 95% confidence interval for the measured expression velocity.

Figure 4:
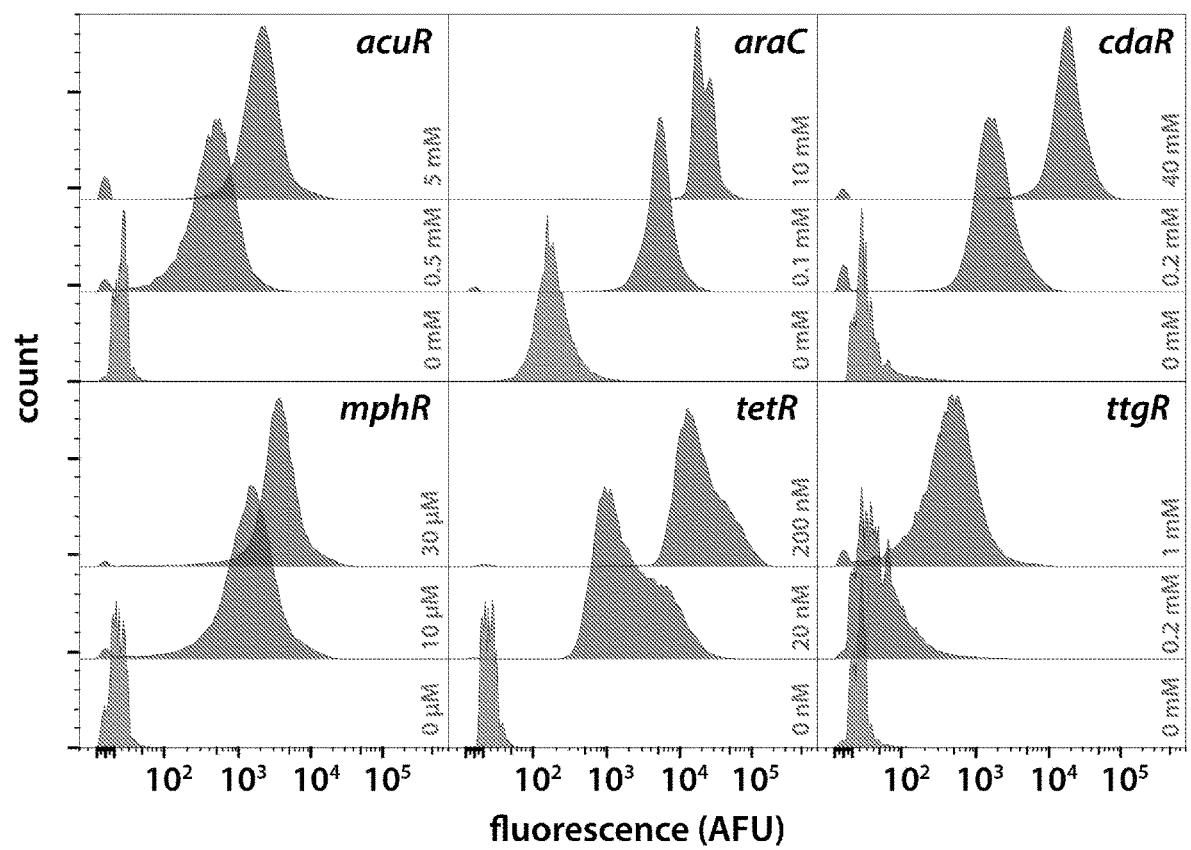

FIG. 4 depicts the behavior of single cells in response to chemical induction evaluated by flow cytometry. 100,000 cells from uninduced (grey), partially induced (green) and fully induced (blue) populations were observed for each high copy biosensor. The specific concentration of inducer is indicated in the plot. Histograms are plotted with a biexponential scale to render the wide range of biosensor activation. The absence of large, well-separated bimodal distributions indicates that bulk fluorescent measurements reflect the induction behavior of individual cells.

Figure 5:
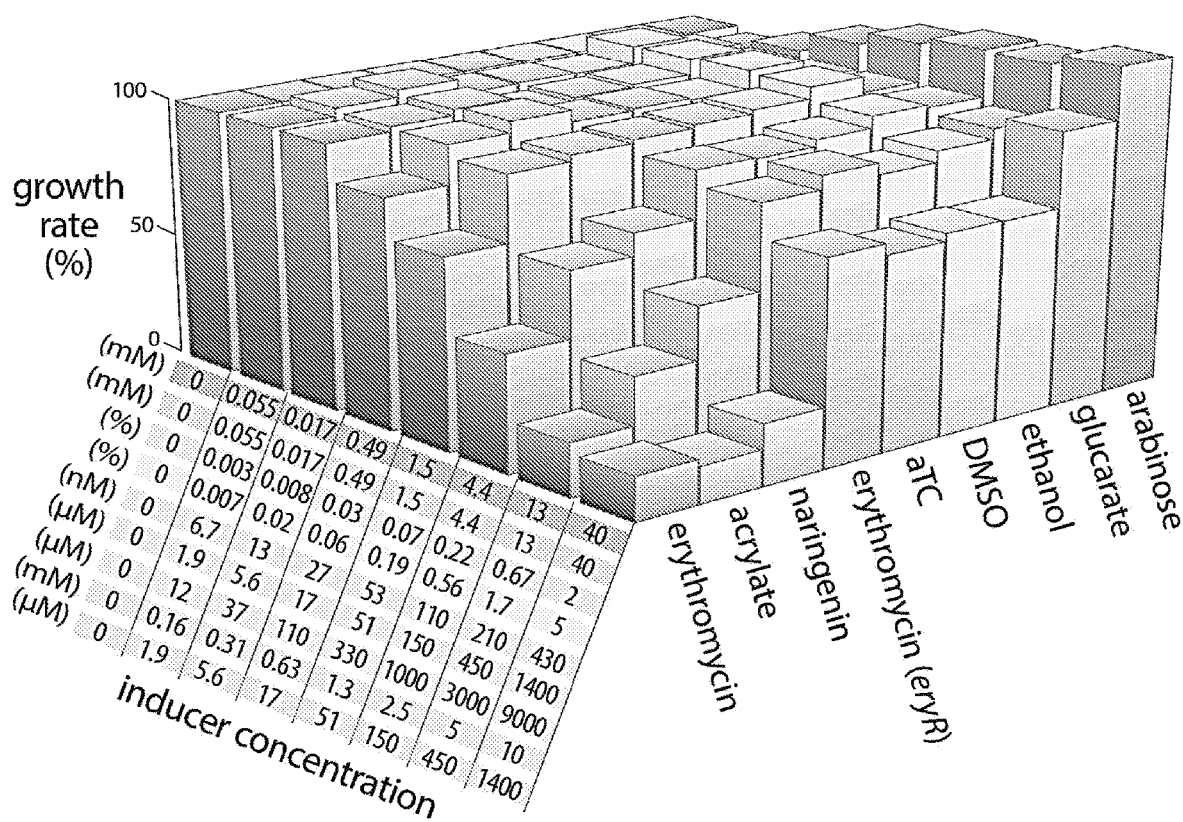

FIG. 5 depicts the toxicity of each inducer chemical evaluated over a wide range of concentrations. Growth rate was measured for each combination of chemical and concentration during the exponential phase of growth. Rates were normalized to the growth rate of cells without any added chemical and plotted as bar height. Concentration of each inducer is indicated in the table, corresponding to the bar chart by order and color. Ethanol and DMSO were included as they are the solvents for aTC and naringenin, respectively. Erythromycin was evaluated twice: with and without the erythromycin resistance gene, eryR. Inducer concentrations mirror the concentrations used in the induction experiments.

Figure 6:
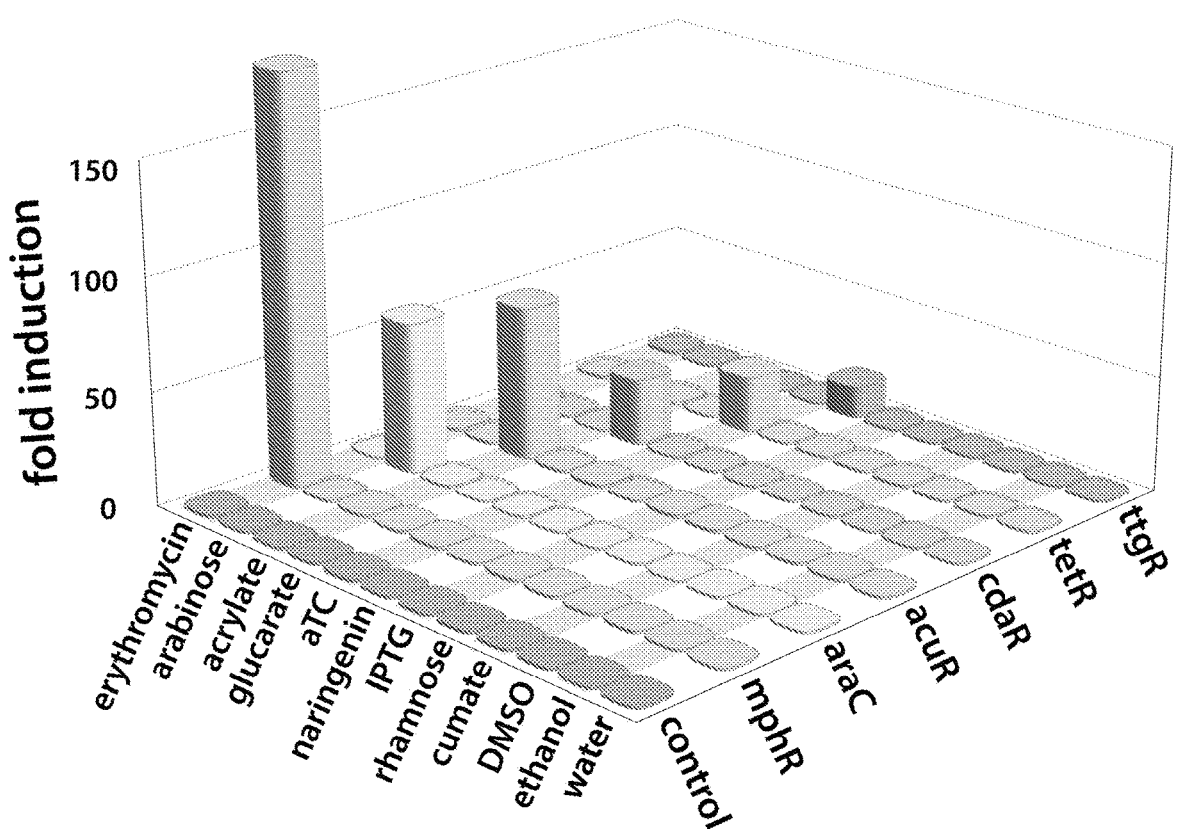

FIG. 6 depicts the evaluated potential for the chemical inducers to activate non-target sensors. The cross-reactivity of the new inducers, along with a selection of other commonly used inducers and inducer solvents, was evaluated against each of six inducible systems. Fold-induction above the basal off-state of each inducible system is plotted as height (n=3). No cross-reactivity was observed.

Figure 7:
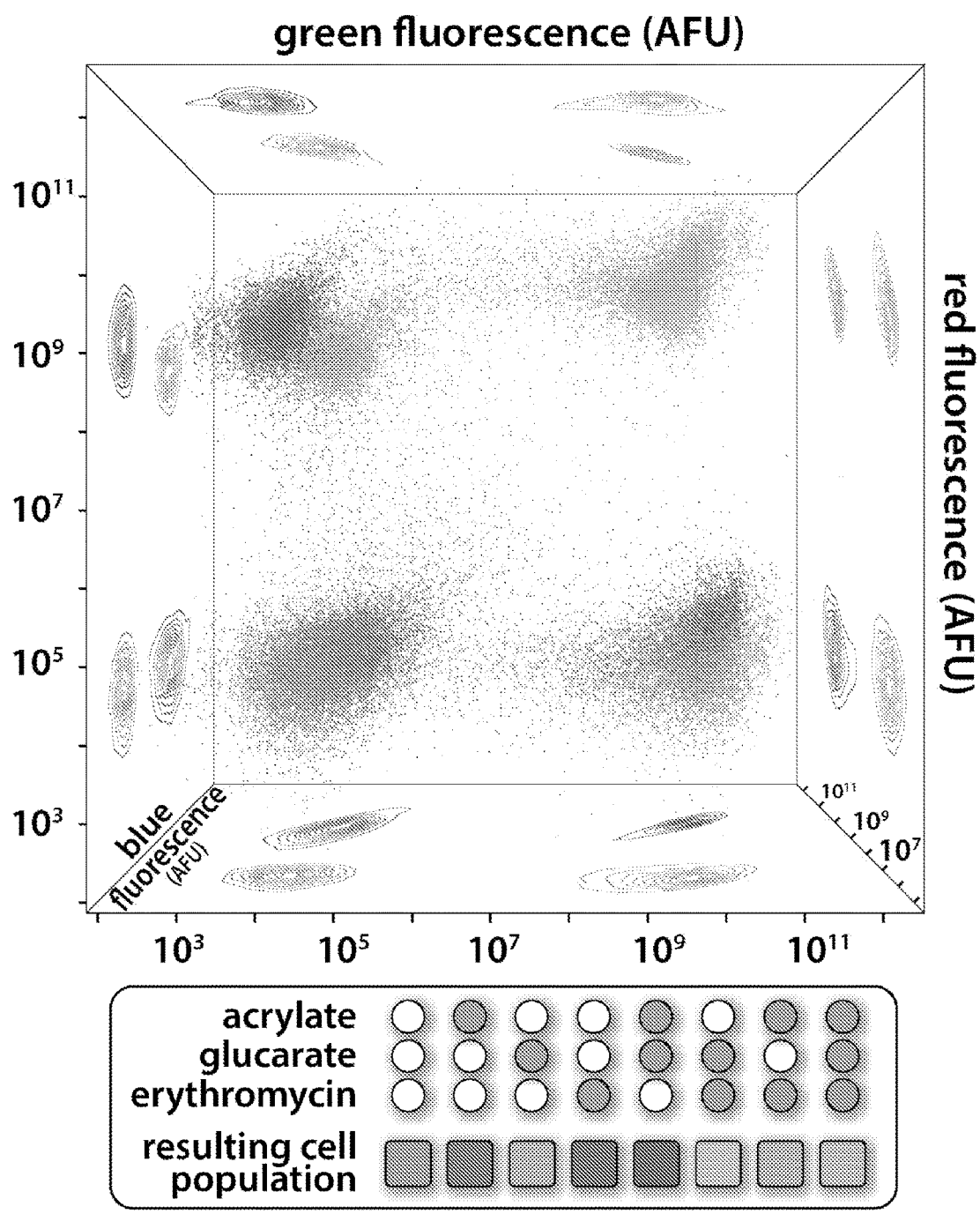

FIG. 7 depicts compatible CdaR-GFP, AcuR-CFP and MphR-mCherry biosensors transformed into the same cell. The potential for these biosensors to be controlled independently was evaluated by flow cytometry. The isogenic cell population was exposed to no inducer (orange), glucarate (light blue), acrylate (dark green), erythromycin (dark blue), glucarate and acrylate (red), glucarate and erythromycin (tan), erythromycin and acrylate (pink) or glucarate, acrylate and erythromycin (light green). The eight combinations of binary induction resulted in eight distinct cell populations when characterized in the three fluorescent channels. The point clouds, each point representing 1 of 10,000 cells, are projected onto the faces of the cube in order to aid in visualization of the 3D space. All axes are log scale to capture the wide range of fluorescent responses.

Figure 8:
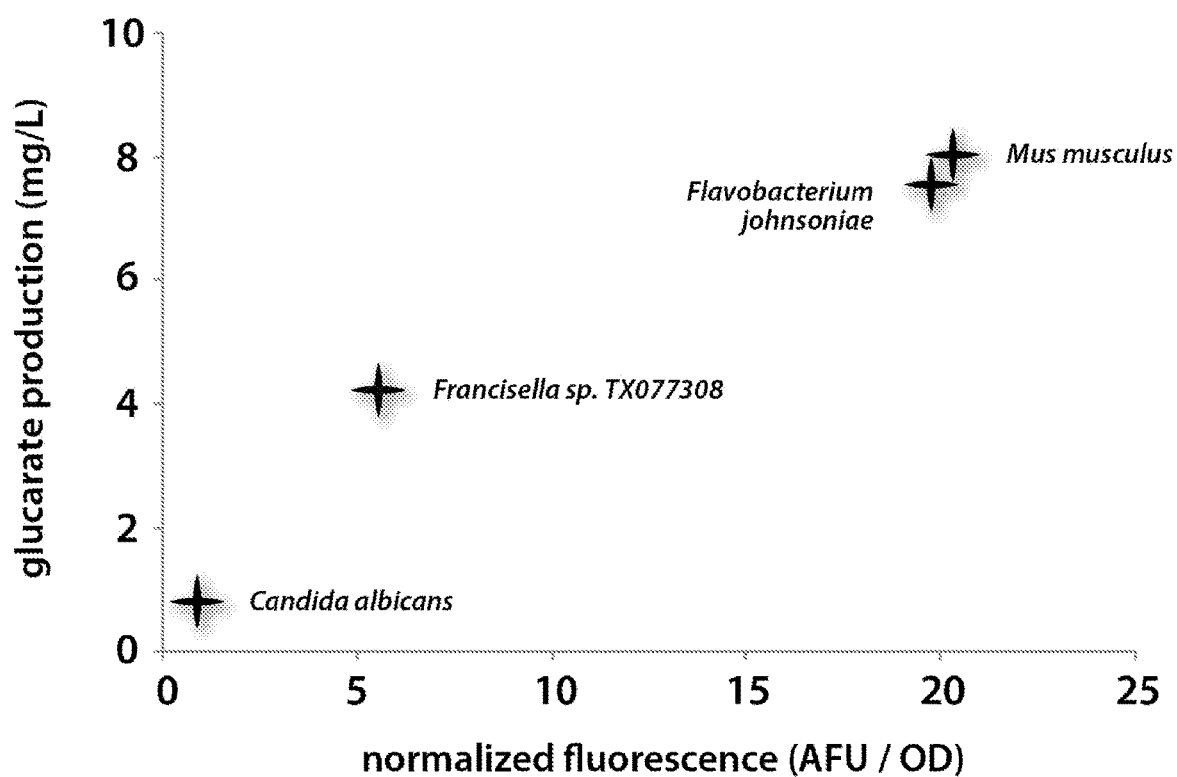

FIG. 8 depicts activation of the CdaR biosensor being well correlated with glucarate titers. Glucarate can be produced from myo-inositol by the enzymes MIOX and Udh. MIOX orthologs were transformed into cells containing Udh and the CdaR biosensor. Fluorescence was observed 48 hours after addition of myo-inositol. Glucarate titers were measured after the same period of time in identical strains without the glucarate biosensor. All coefficients of variation are less than 10% (n=3).

Figure 9:
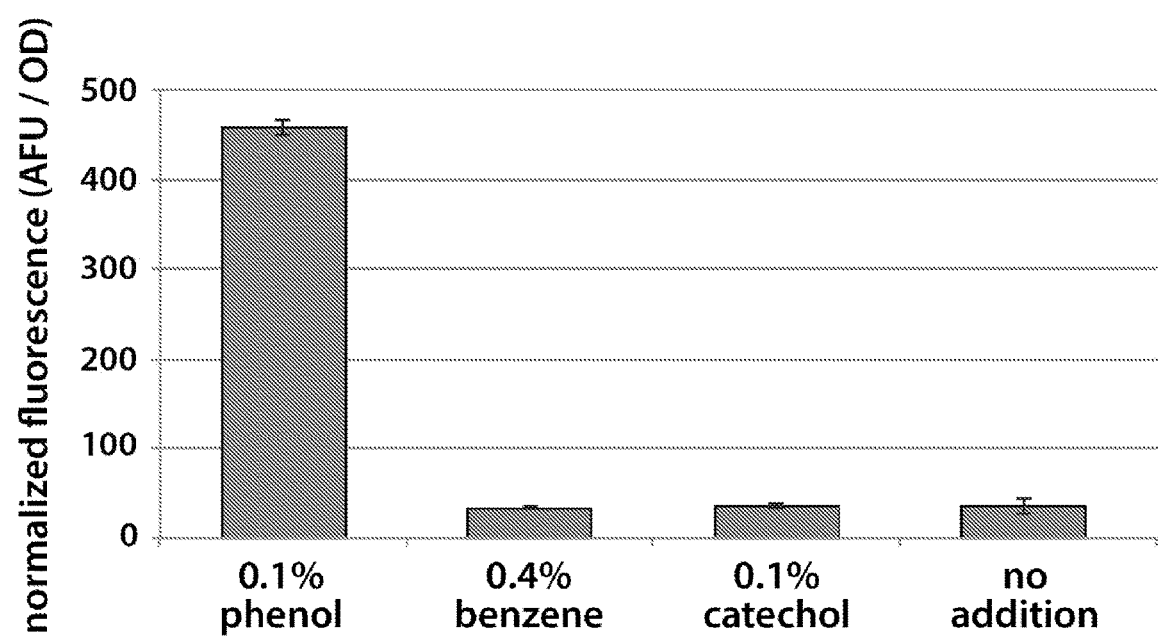

FIG. 9 depicts the TtgR biosensor being evaluated for its ability to aid in the directed evolution of enzymatic phenol production. A fluorescent response was observed in the presence of 0.1% phenol, while background levels of fluorescence were observed when the sensor was induced with the precursor molecule benzene. Catechol is a side-product of phenol production and did not activate the sensor. All experiments were carried out in triplicate.

Figure 10:
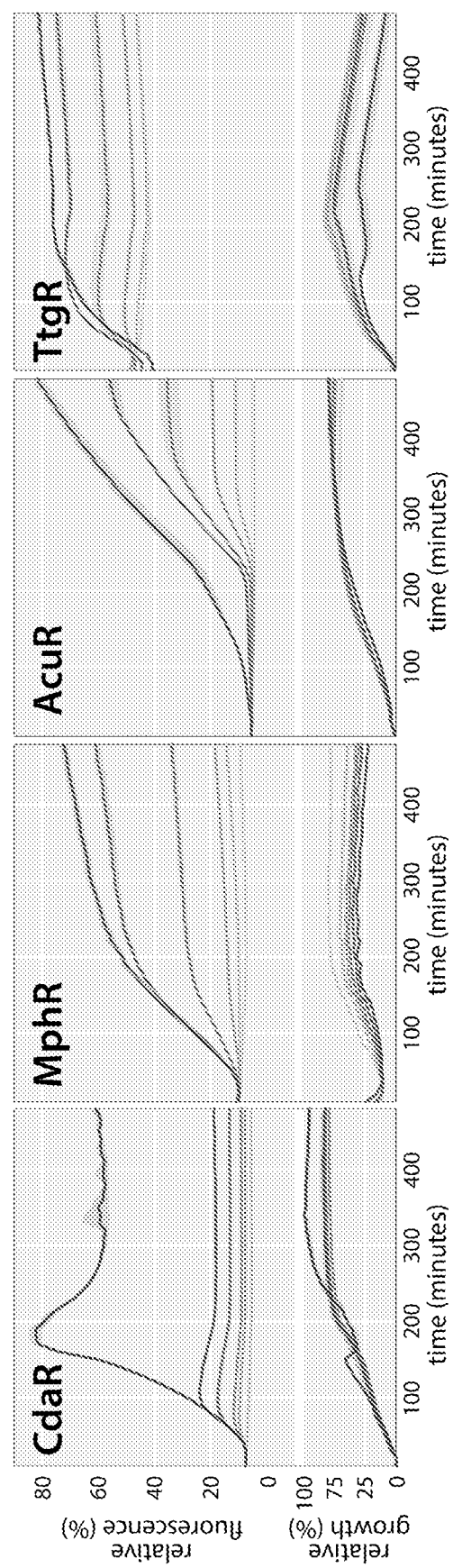

FIG. 10 depicts induction and growth kinetics for the low-copy glucarate (CdaR), erythromycin (MphR), acrylate (AcuR) and naringenin (TtgR) biosensors. Chemical inducers are added at time zero and fluorescence is observed for eight hours. Lower panels show the optical density of the induced cultures over time. Induction levels are indicated by shade, with darker colors indicating higher inducer concentrations. Glucarate induction levels are 13 mM, 4.4 mM, 1.5 mM, 0.49 mM, 0.17 mM and no inducer addition. Erythromycin induction levels are 150 µM, 51 µM, 17 µM, 5.6 µM, 1.9 µM and no inducer addition. Acrylate induction levels are 5 mM, 2.5 mM, 1.3 mM, 0.63 mM, 0.31 mM and no inducer addition. Naringenin induction levels are 9 mM, 3 mM, 0.33 mM, 0.11 mM, 0.037 mM and no inducer addition. Fluorescence and optical density are normalized as described herein. The standard error of the mean is represented with a 95% confidence interval (n=3).

Figure 11:
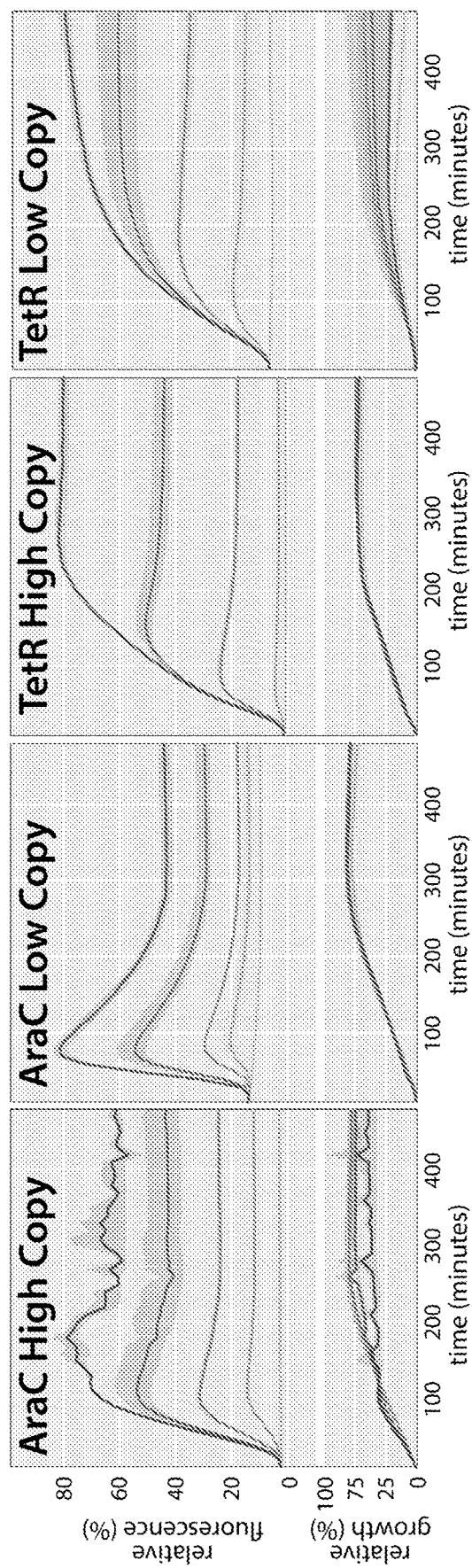

FIG. 11 depicts induction and growth kinetics for the high- and low-copy arabinose (AraC) and anhydrotetracycline (TetR) biosensors. Chemical inducers are added at time zero and fluorescence is observed for eight hours. Lower panels show the optical density of the induced cultures over time. Induction levels are indicated by shade, with darker colors indicating higher inducer concentrations. Arabinose induction levels are 490 µM, 170 µM, 55 µM, 18 µM and no inducer addition. Anhydrotetracycline induction levels are 430 nM, 210 nM, 110 nM, 53 nM and no inducer addition. Fluorescence and optical density are normalized as described herein. The standard error of the mean is represented with a 95% confidence interval (n=3).

Figure 12:
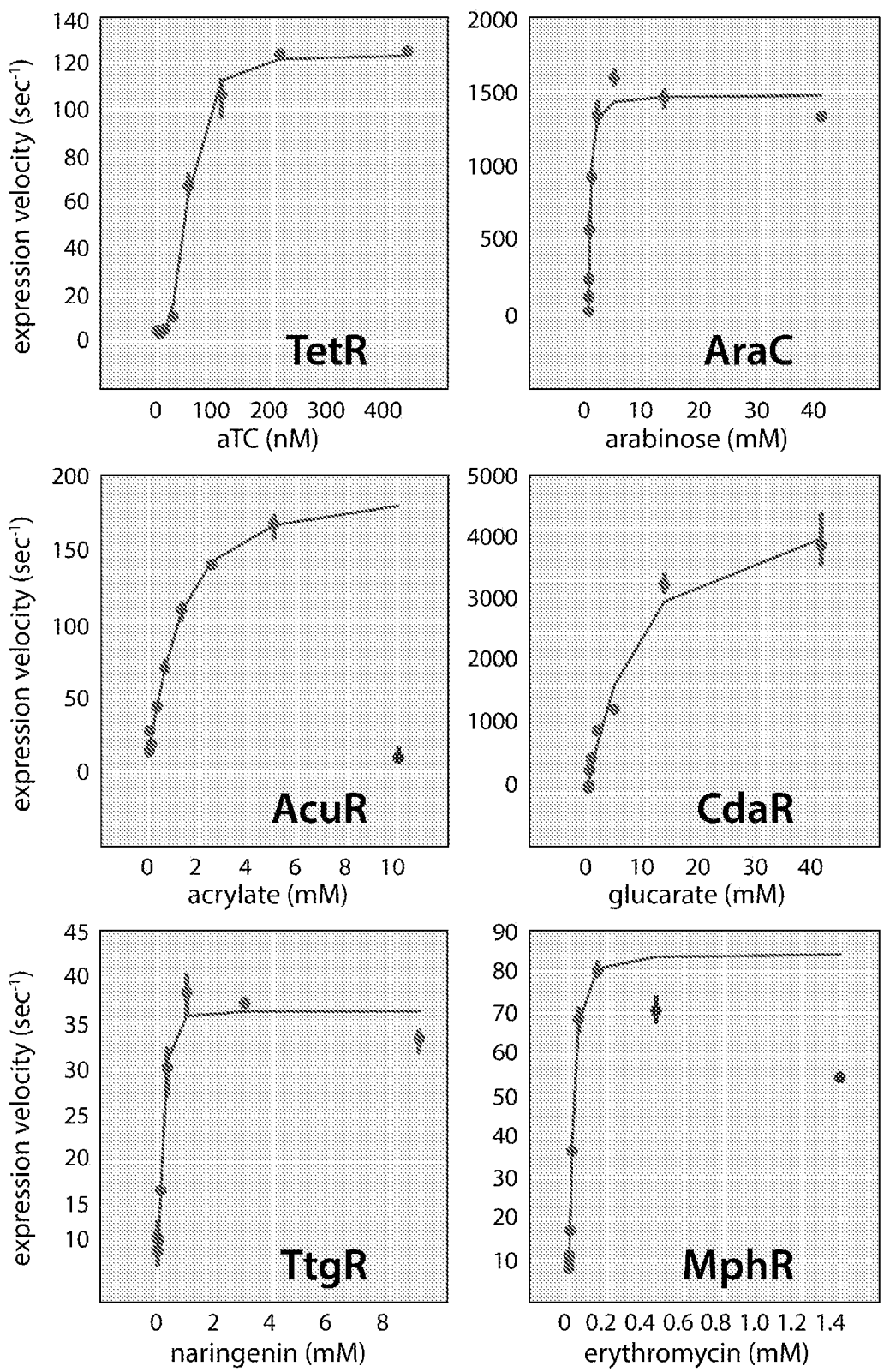

FIG. 12 depicts fitting of low-copy promoter activity to a model of inducible gene expression. The maximum expression velocity of each inducible promoter was determined at various levels of induction (points). The data was fit to a Hill function modified to account for basal and maximal promoter activity (green lines). The anhydrotetracycline (TetR) and naringenin (TtgR) biosensors show high induction cooperativity. The arabinose (AraC), glucarate (CdaR), acrylate (AcuR) and erythromycin (MphR) biosensors show low or moderate levels of cooperativity. The 10 mM acrylate, 1400 µM and 450 µM erythromycin induction conditions were omitted from the modeling data due to high toxicity (red points). Error bars reflect the 95% confidence interval for the measured expression velocity.

Figure 13:
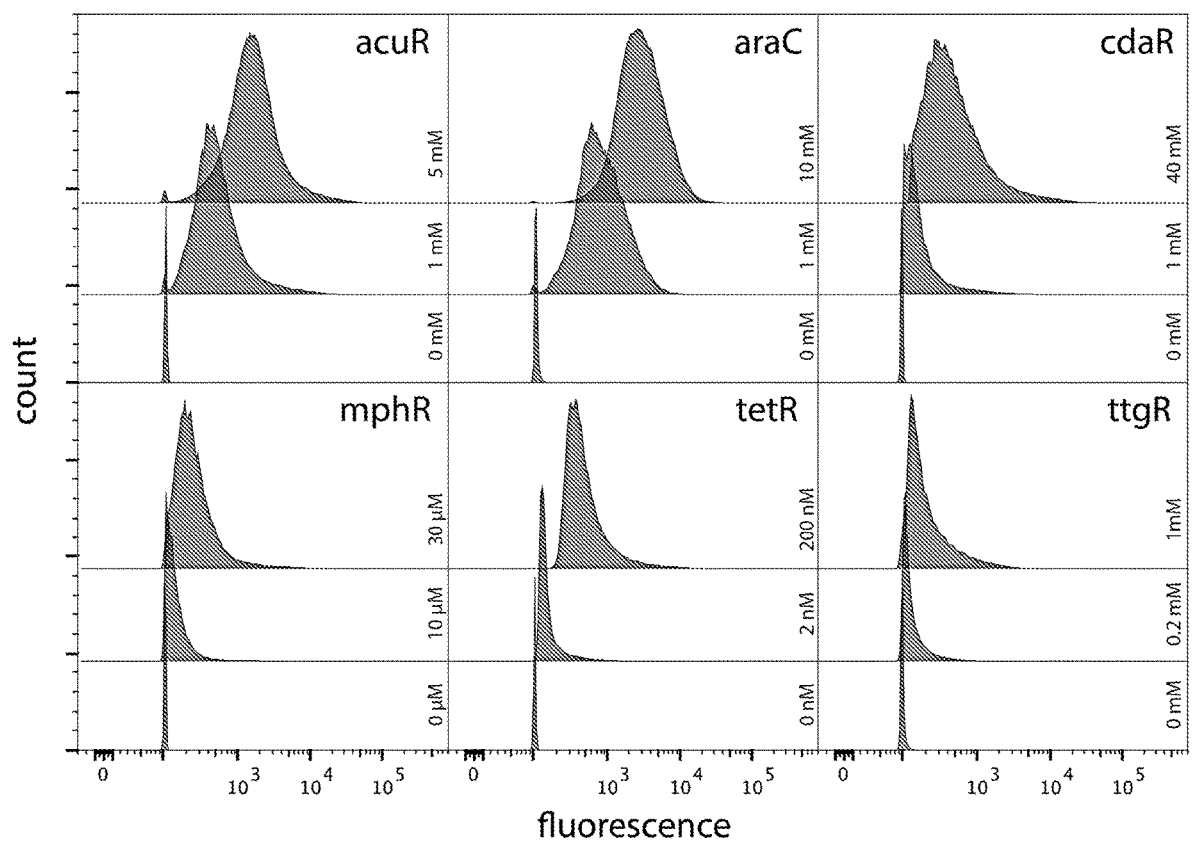

FIG. 13 depicts the behavior of single cells in response to chemical induction evaluated by flow cytometry. 100,000 cells from uninduced (grey), partially induced (green) and fully induced (blue) populations were observed for each low-copy biosensor. The specific concentration of inducer is indicated in the plot. Histograms are plotted with a biexponential scale to render the wide range of biosensor activation. The absence of large, well-separated bimodal distributions indicates that bulk fluorescent measurements do indeed reflect the induction behavior of individual cells.

Figure 14:
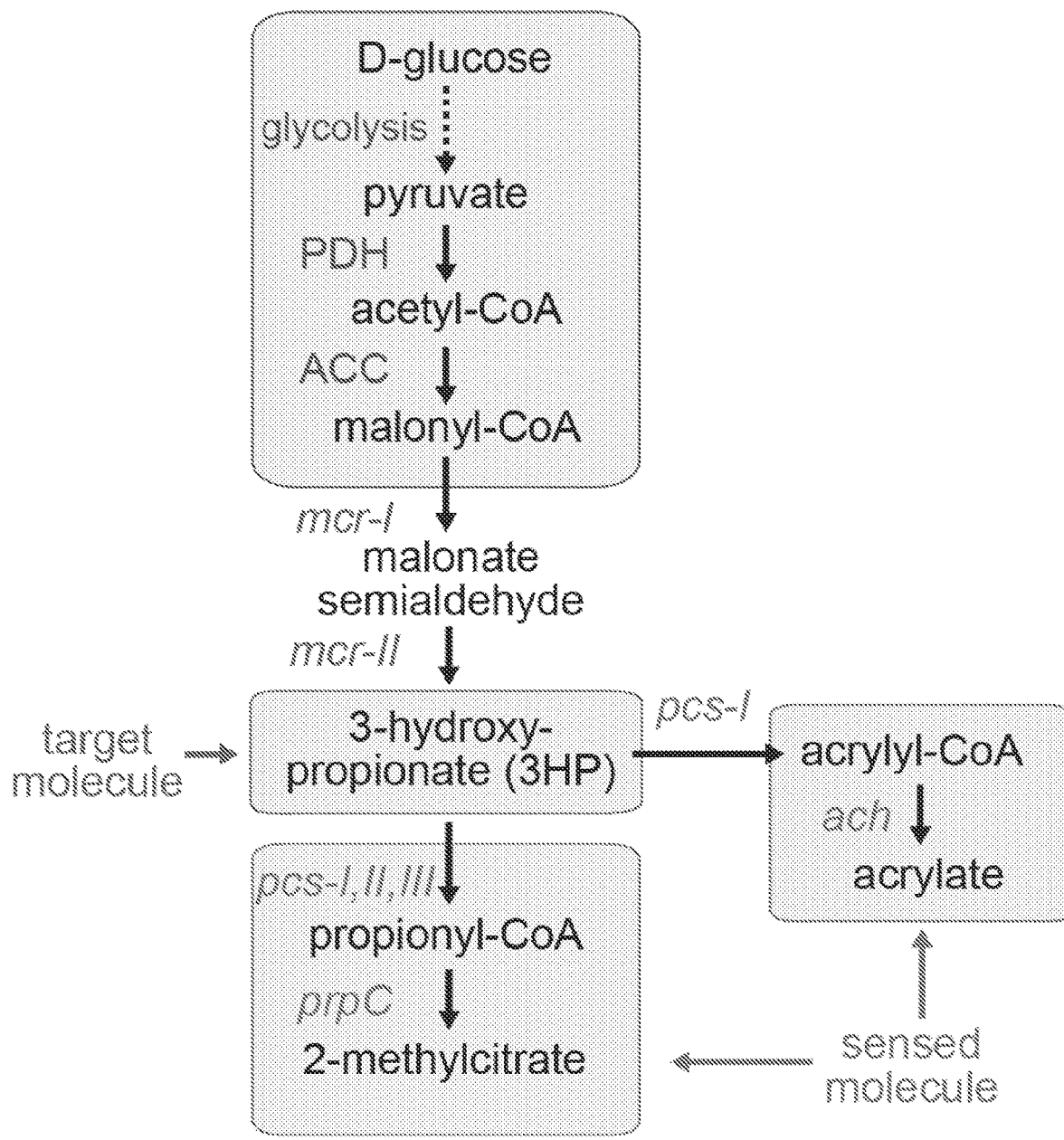

FIG. 14 is a schematic showing one biological route to 3HP from glucose and the enzymatic reactions necessary to convert 3hP into compounds for sensing.

Figure 15A:
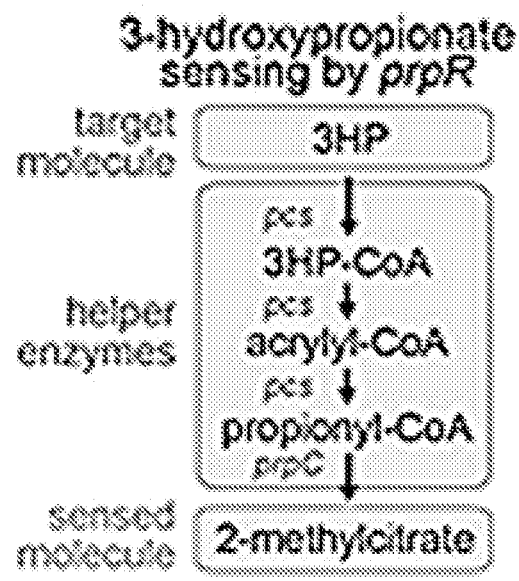
Figure 15B:
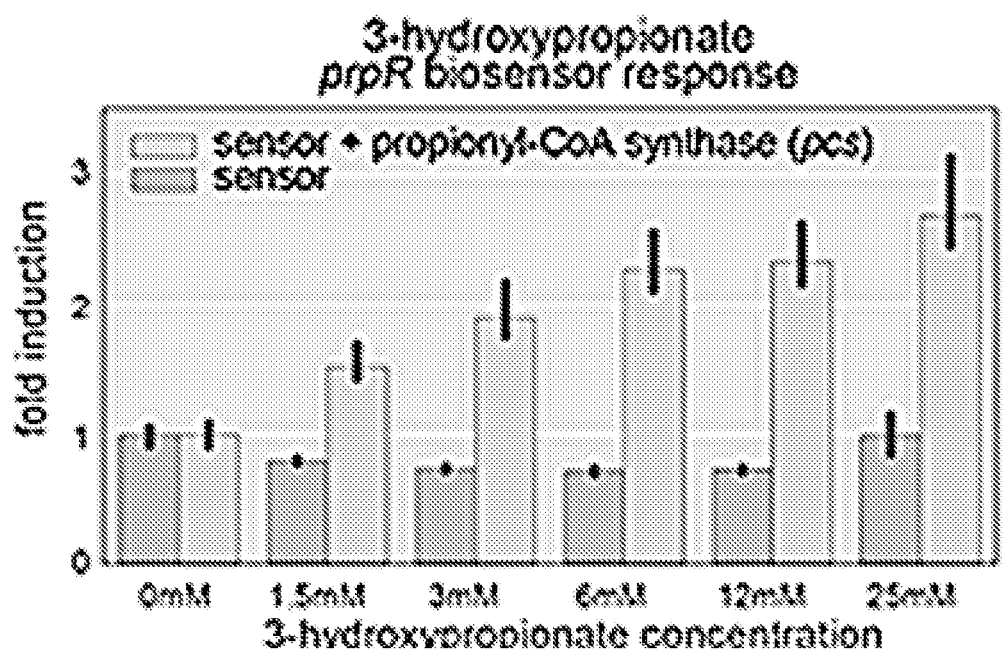
Figure 15C:
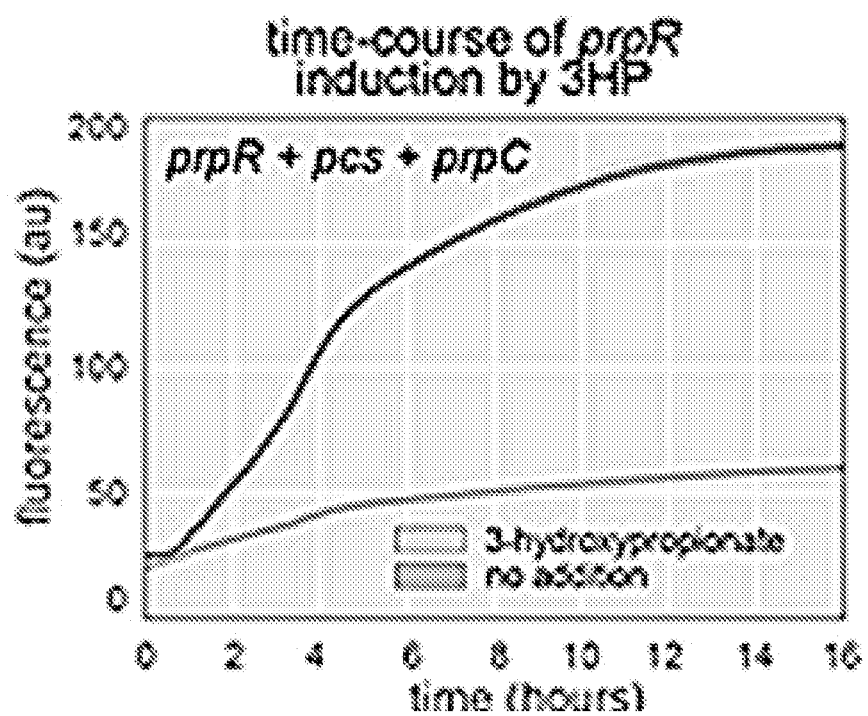

FIG. 15A, FIG. 15B and FIG. 15C depict development of the prpR-based 3-hydroxypropionate (3HP) biosensor. FIG. 15A depicts two helper enzymes, pcs from *Chloroflexus aurantiacus* and the endogenous prpC, convert 3HP into the prpR-binding compound 2-methylcitrate. FIG. 15B is a graph depicting that exogenously supplied 3HP triggers a fluorescent response in cells containing the biosensor (green bars). Increasing the concentration of 3HP results in a higher fluorescent output. No biosensor activation is observed without the helper enzyme pcs (grey bars). FIG. 15C is a graph depicting that the fluorescent response of the biosensor begins after one hour and achieves 90% saturation after ten hours (green line). Basal induction increases over time but remains low (grey line). Error bars and confidence bands represent the 95% confidence interval (n=3).

Figure 16A:
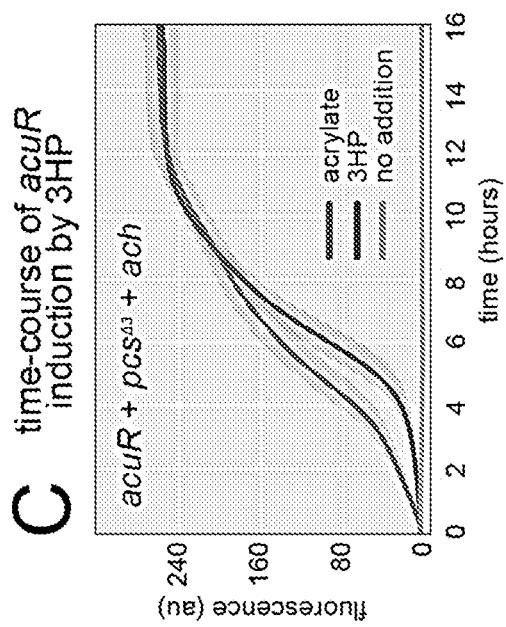
Figure 16B:
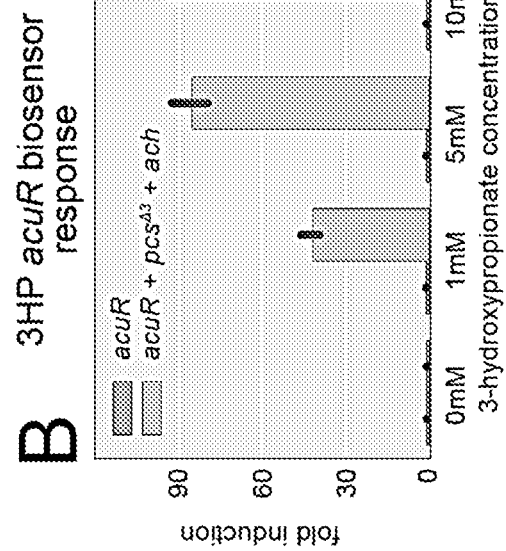
Figure 16C:
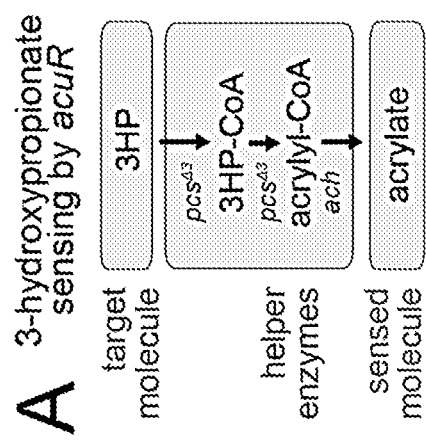

FIG. 16A, FIG. 16B and FIG. 16C depict development of the acuR-based 3-hydroxypropionate (3HP) biosensor. FIG. 16A depicts that two heterologous helper enzymes, a truncated form of pcs (pcs$^{\Delta 3}$) and the acrylyl-CoA hydrolase ach, convert 3HP into the acuR-binding compound acrylate. FIG. 16B is a graph depicting that exogenously supplied 3HP triggers a fluorescent response in cells containing the biosensor (blue bars). Higher concentrations of 3HP result in higher fluorescent outputs. No biosensor activation is observed without the helper enzymes pcs$^{\Delta 3}$ and ach (grey bars). FIG. 16C is a graph depicting that the fluorescent response of the biosensor to 3HP begins immediately and achieves 90% saturation after eight hours (blue line). Induction by acrylate is initially more rapid but achieves the same final fluorescence (green line). Basal induction is low over the duration of the experiment (grey line). Error bars and confidence bands represent the 95% confidence interval (n=3).

Figure 17:
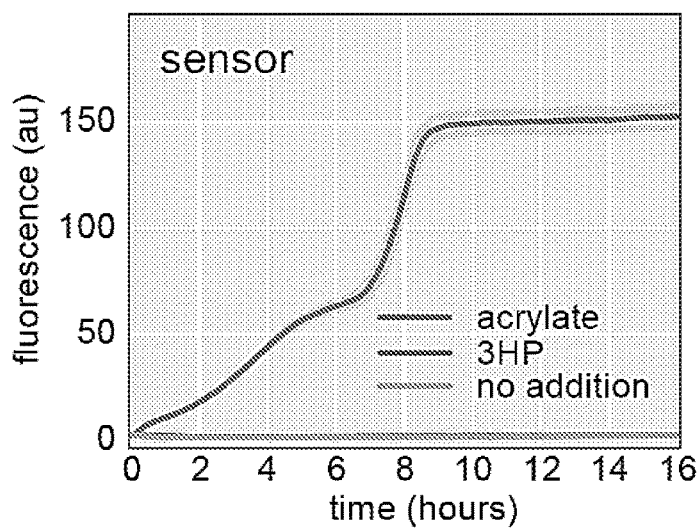

FIG. 17 is a graph depicting that cells containing the acrylate biosensor without the helper plasmid respond to acrylate but not to 3HP.

Figure 18:
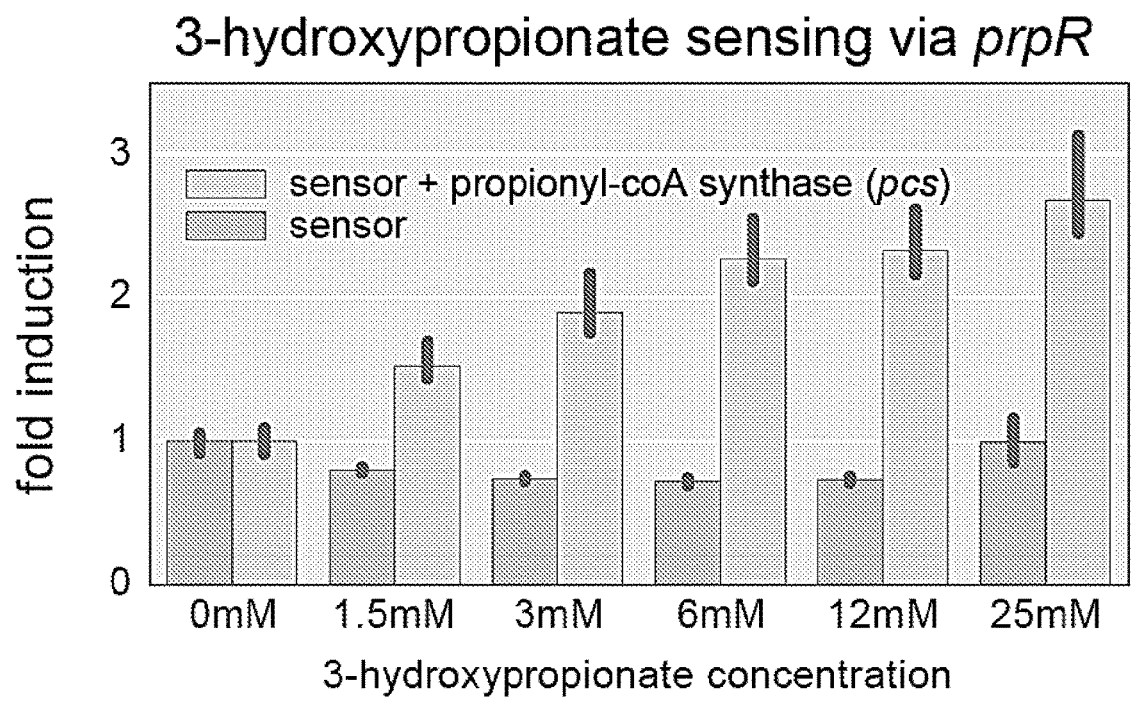

FIG. 18 is graph depicting the response of the prpR-based 3HP biosensor to increasing concentrations of 3HP. The green bars show the complete system is responsive to 3HP while the gray bars show that the prpR sensor alone cannot detect 3HP.

Figure 19:
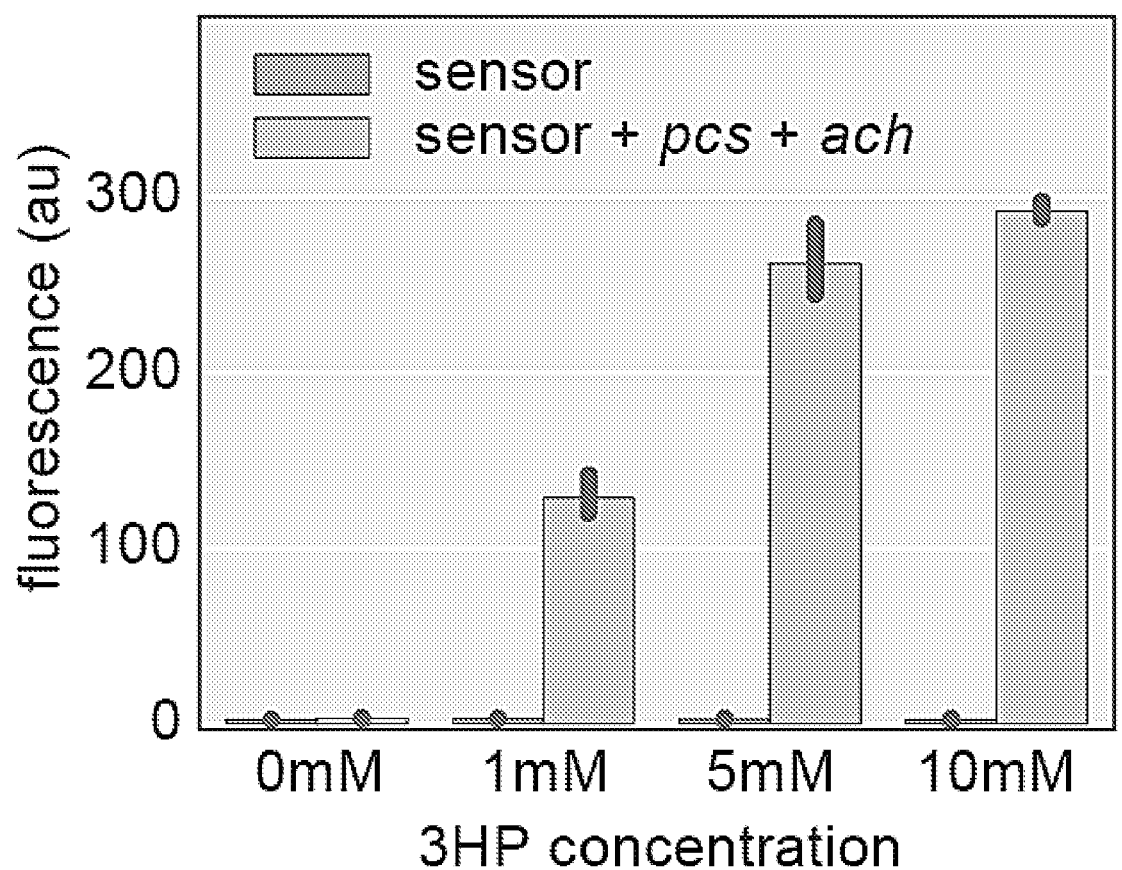

FIG. 19 is a graph depicting the response of the acuR-based 3HP biosensor to increasing concentrations of 3HP. The blue bars show the complete system is responsive to increasing amounts of 3HP while the gray bars show that the acuR sensor alone does not react to the presence of 3HP.

Figure 20A:
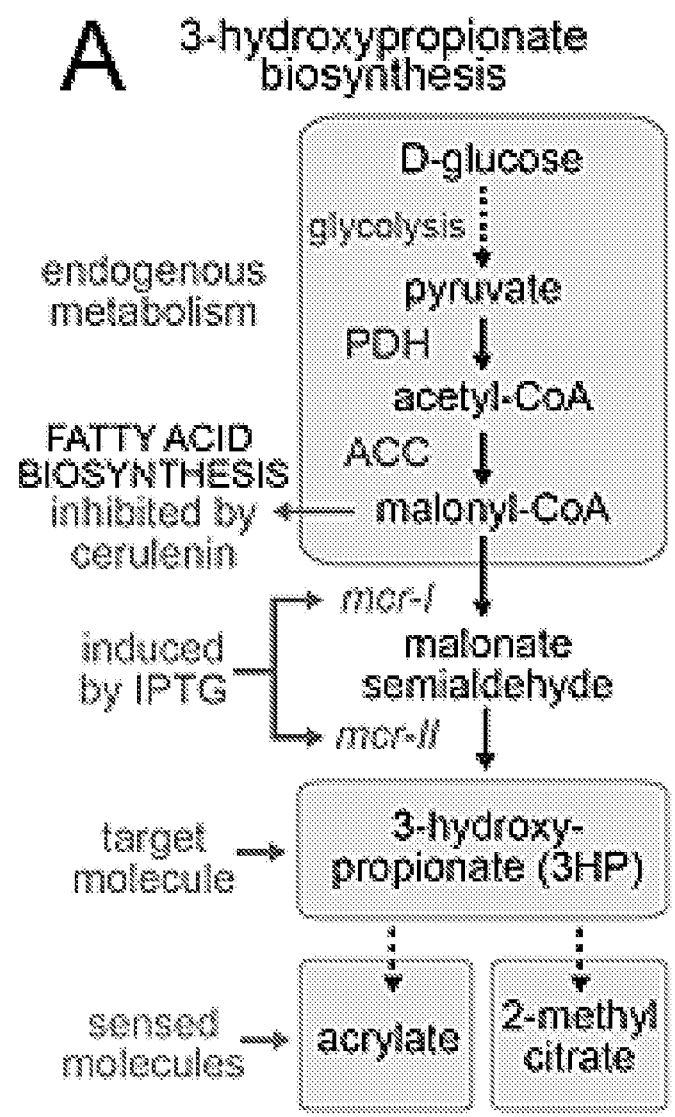
Figure 20B:
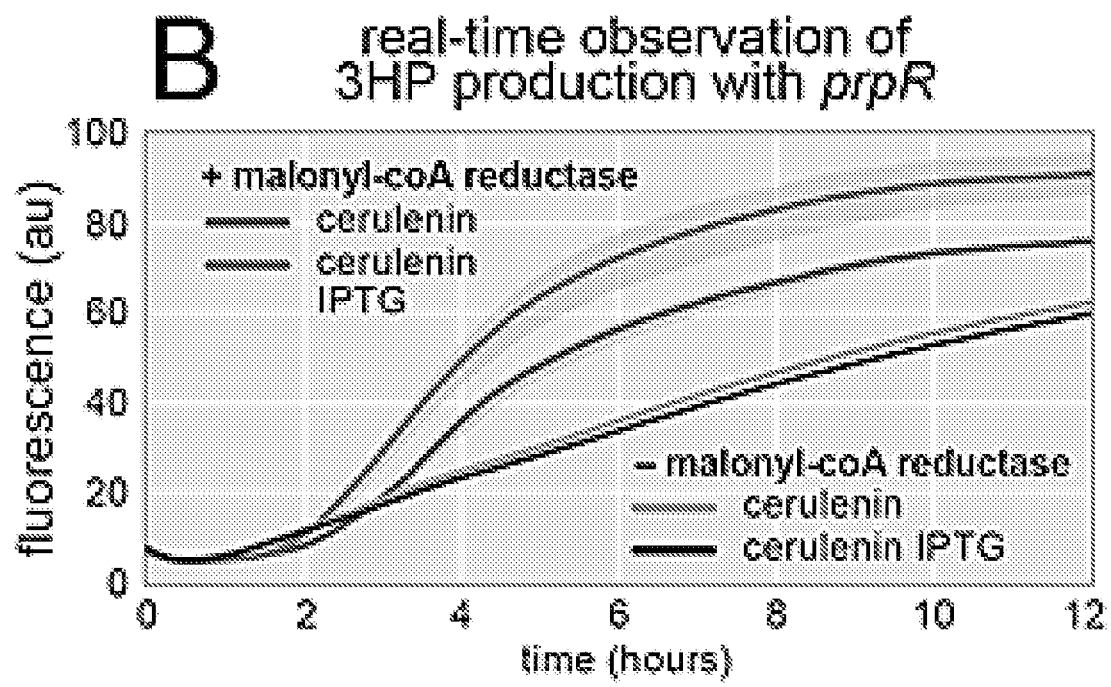
Figure 20C:
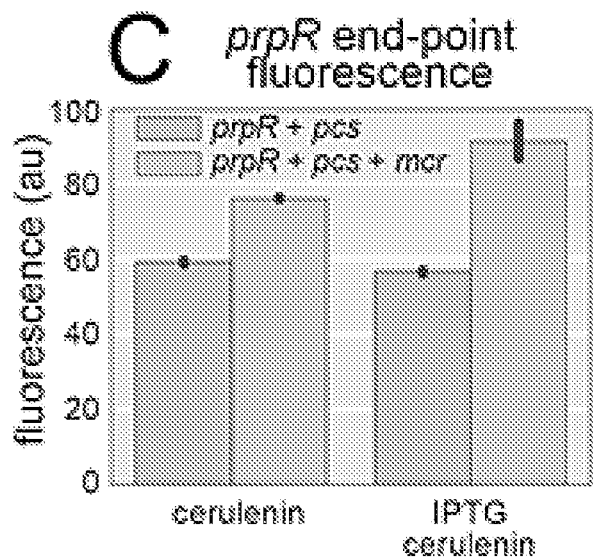
Figure 20D:
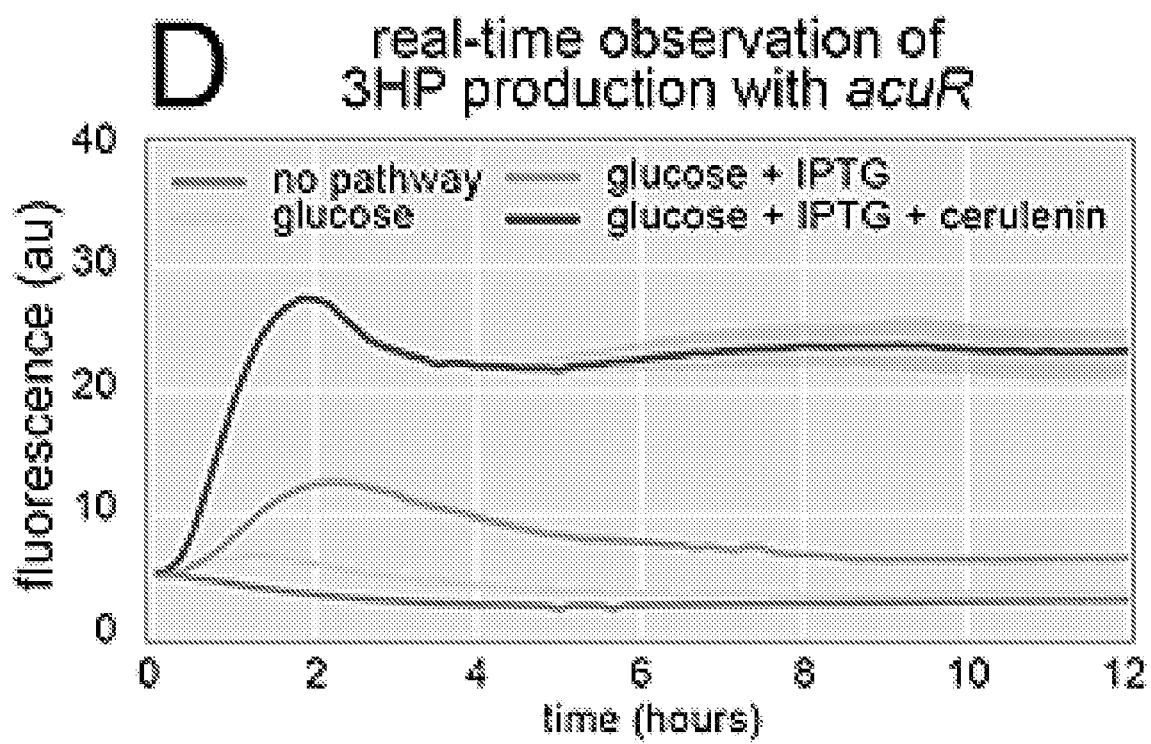
Figure 20E:
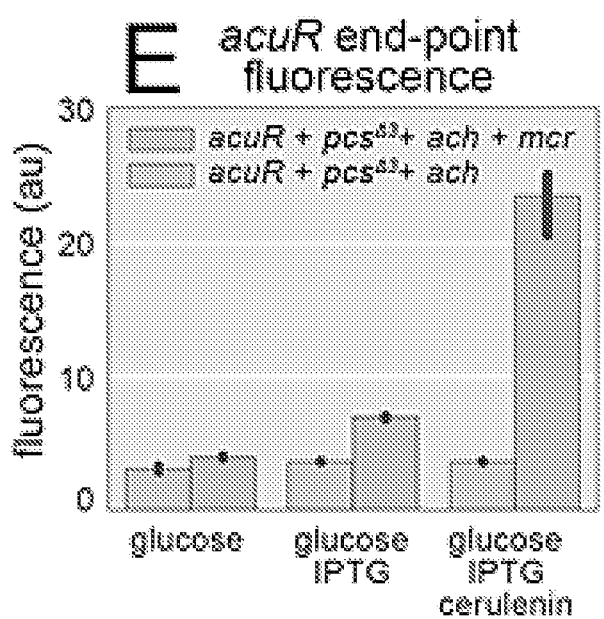
Figure 20F:
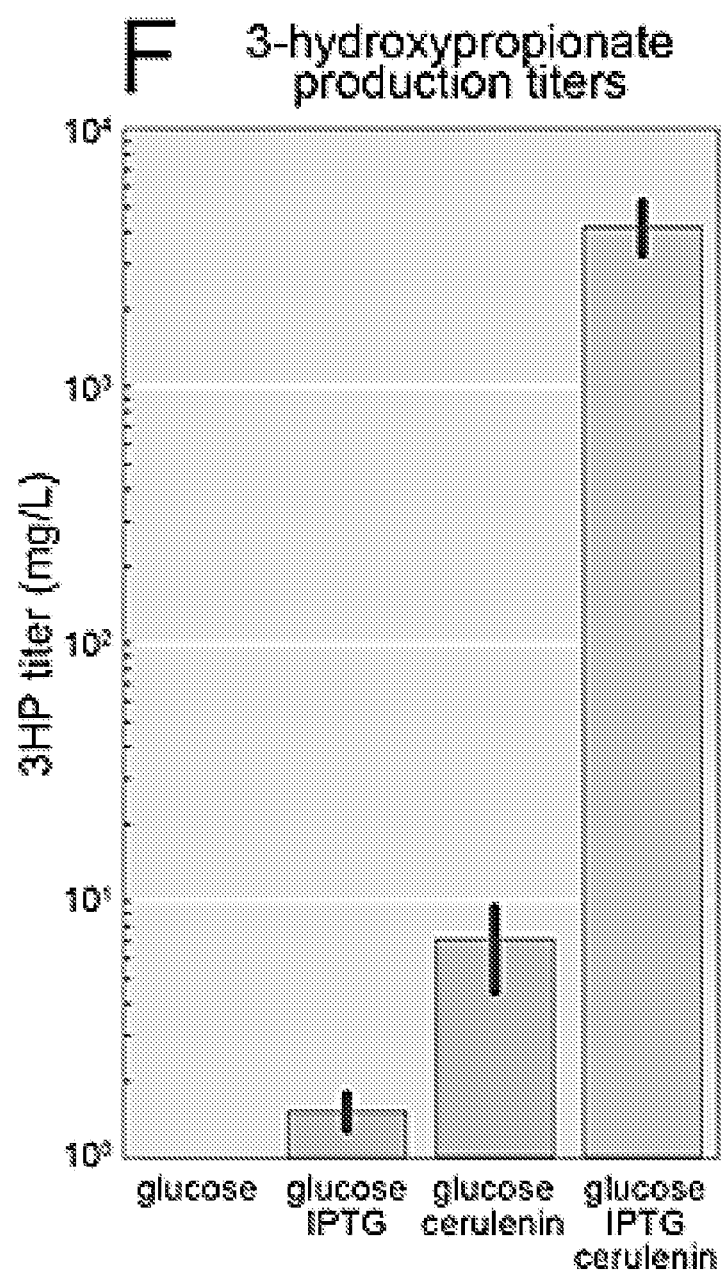

FIG. 20A, FIG. 20B, FIG. 20C, FIG. 20D, FIG. 20E and FIG. 20F depict formation of 3-hydroxypropionate observed by fluorescence. FIG. 20A is a schematic depicting that 3HP can be produced from glucose by converting malonyl-CoA into malonate semialdehyde and then on to 3HP. Malonyl-CoA reductase (mcr) performs both of these reactions but competes with fatty acid biosynthesis for malonyl-CoA. FIG. 20B is a graph depicting that the prpR-based 3HP biosensor reports 3HP production progress in real-time. Addition of cerulenin increases the malonyl-CoA pool, providing a boost in 3HP production (purple line). Addition of IPTG increases mcr activity and further increases 3HP production (blue line). Cerulenin and IPTG have no impact on the fluorescent response of cells without mcr (grey and black lines). FIG. 20C is a graph depicting end-point fluorescence of the prpR-based biosensor. FIG. 20D is a graph depicting that the acuR-based 3HP biosensor reports the progress of 3HP production in real-time. The addition of 50 mM glucose (tan line) results in a small increase in fluorescence over background (grey line). Addition of IPTG increases the activity of mcr and the activation of the biosensor (orange line). Providing glucose, IPTG and cerulenin together results in the highest rate of biosensor activation (red line). FIG. 20E is a graph depicting that the end-point fluorescence of the acuR-based biosensor reveals an approximately 5-fold increase in fluorescence under optimized culture conditions (glucose, IPTG, cerulenin) when compared to non-optimized culture conditions (glucose, purple bars). In the absence of mcr, culture conditions have no effect on biosensor activation (blue bars). FIG. 20F is a graph depicting that the culture conditions evaluated by biosensor activation were evaluated for 3HP production. Titers were measured by LC/MS and found to correspond to biosensor activation. A record 4.2 g/L 3HP was achieved with glucose, IPTG and cerulenin. Error bars and confidence bands represent the 95% confidence interval (n=3). Fluorescence measurements are in arbitrary units and different panels should not be quantitatively compared.

Figure 21A:
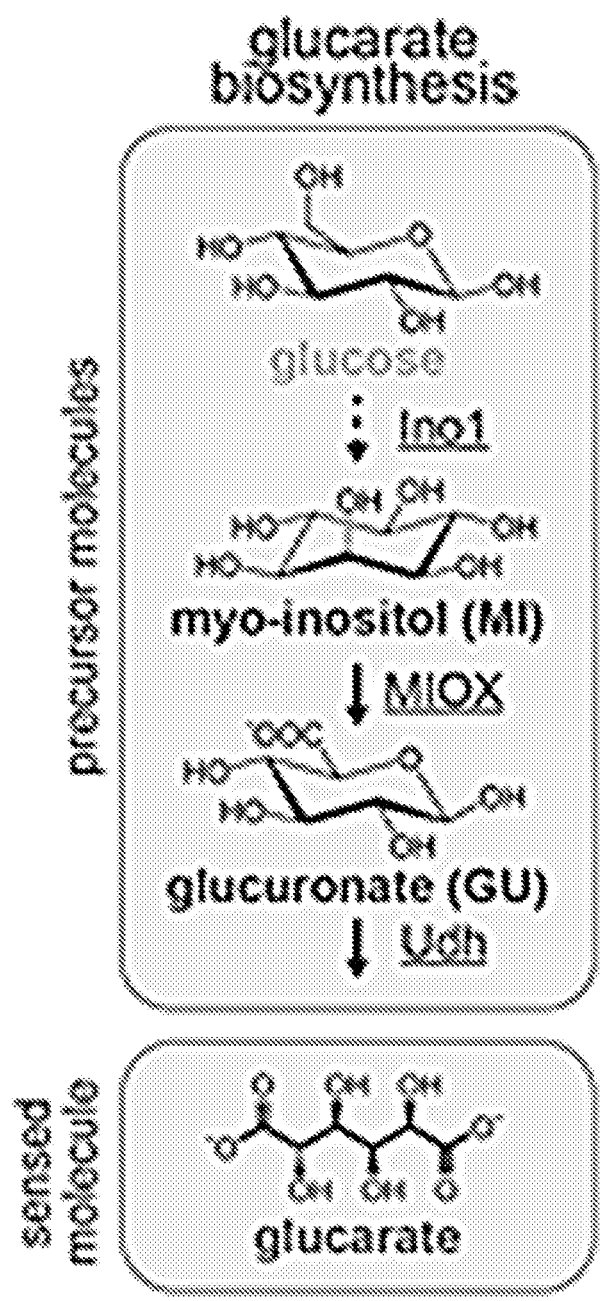
Figure 21B:
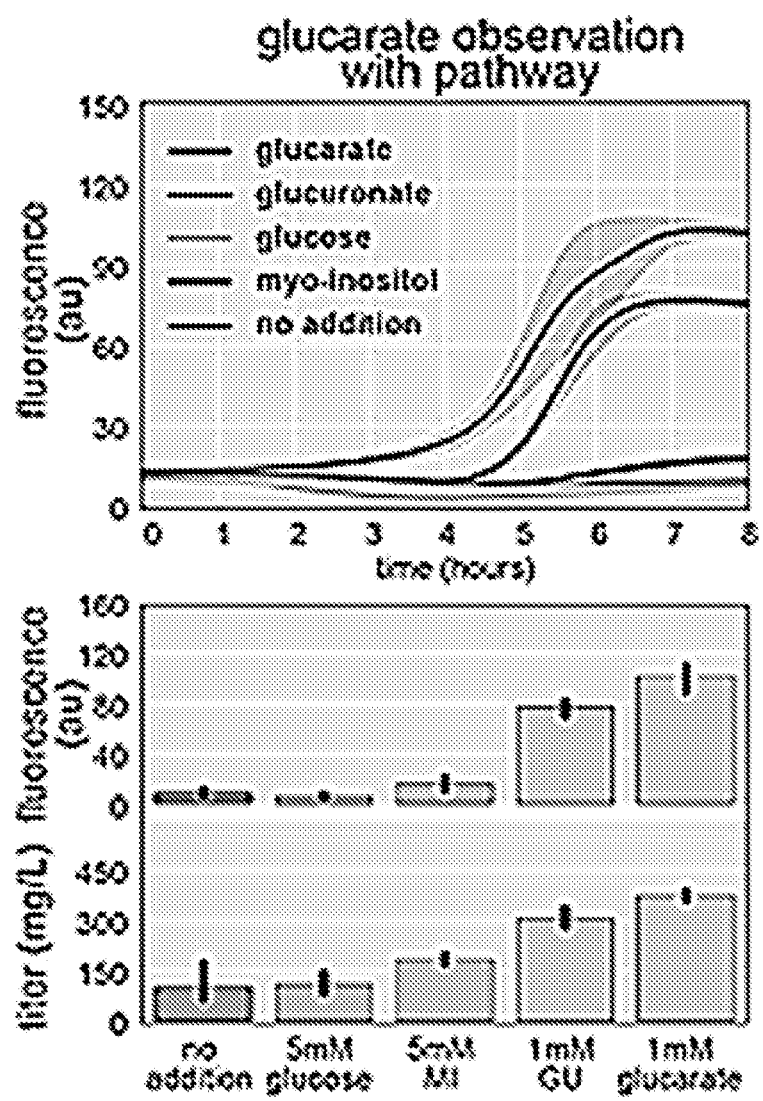
Figure 21C:
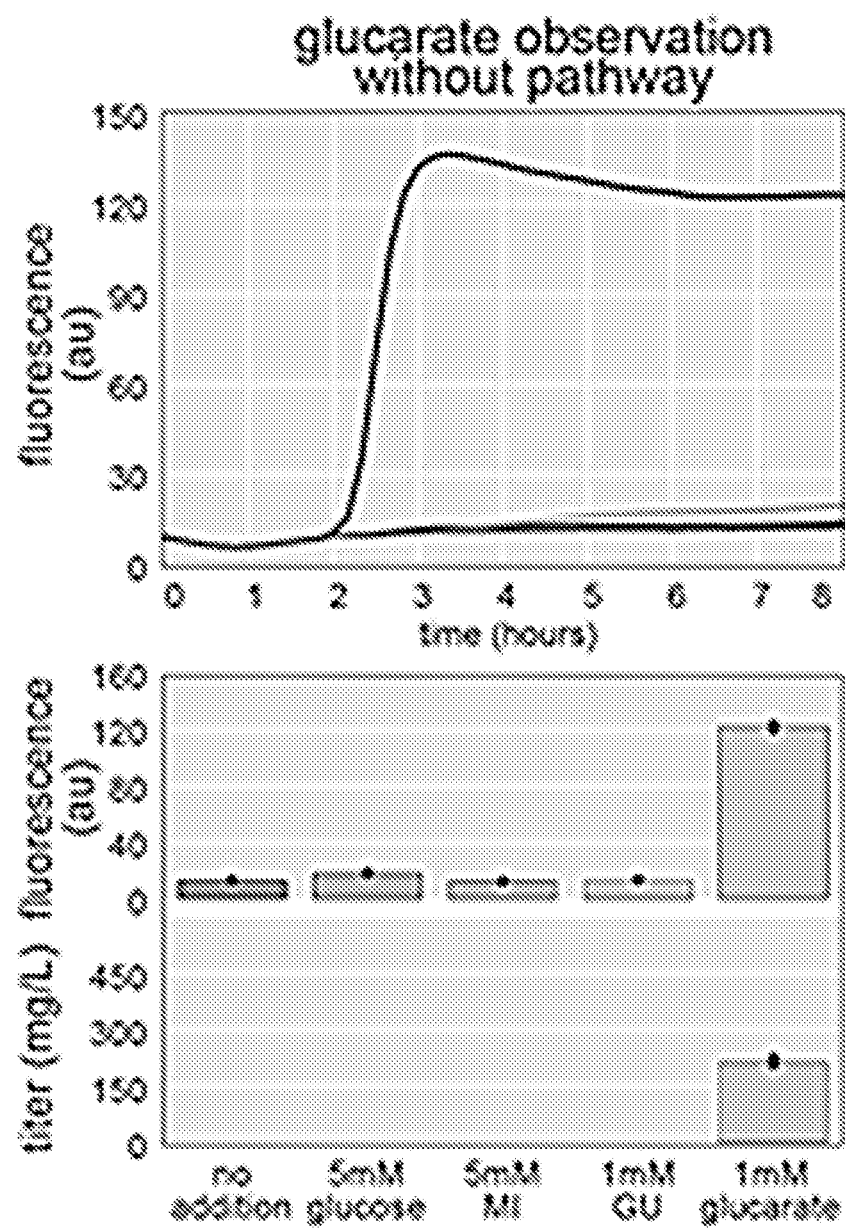

FIG. 21A, FIG. 21B and FIG. 21C depict real-time observation of glucarate production. FIG. 21A is a schematic depicting that glucarate can be produced from glucose with the expression of three heterologous enzymes of various activities. Udh has high activity, MIOX has low activity and Ino1 competes with glycolysis for glucose-6-phosphate. The presence of glucarate activates the biosensor. FIG. 21B is a graph depicting intermediates of glucarate biosynthesis added to the media. Fluorescence is observed over time as the intermediates are converted to glucarate. Biosensor activation by glucuronate (blue line) lags behind activation by glucarate (green line). Both glucarate and glucuronate activation are faster than activation by myo-inositol (purple line) or glucose (tan line), reflecting the dynamics of the biosynthesis pathway. End-point fluorescence trends well with LC/MS determined glucarate titers. FIG. 21C is a graph depicting that in the absence of the glucarate biosynthesis pathway there is no biosensor activation or glucarate production (as determined by LC/MS) from any of the pathway intermediates. Addition of glucarate resulted in biosensor activation (green line). Error bars and confidence bands represent the 95% confidence interval (n=3).

Figure 22:
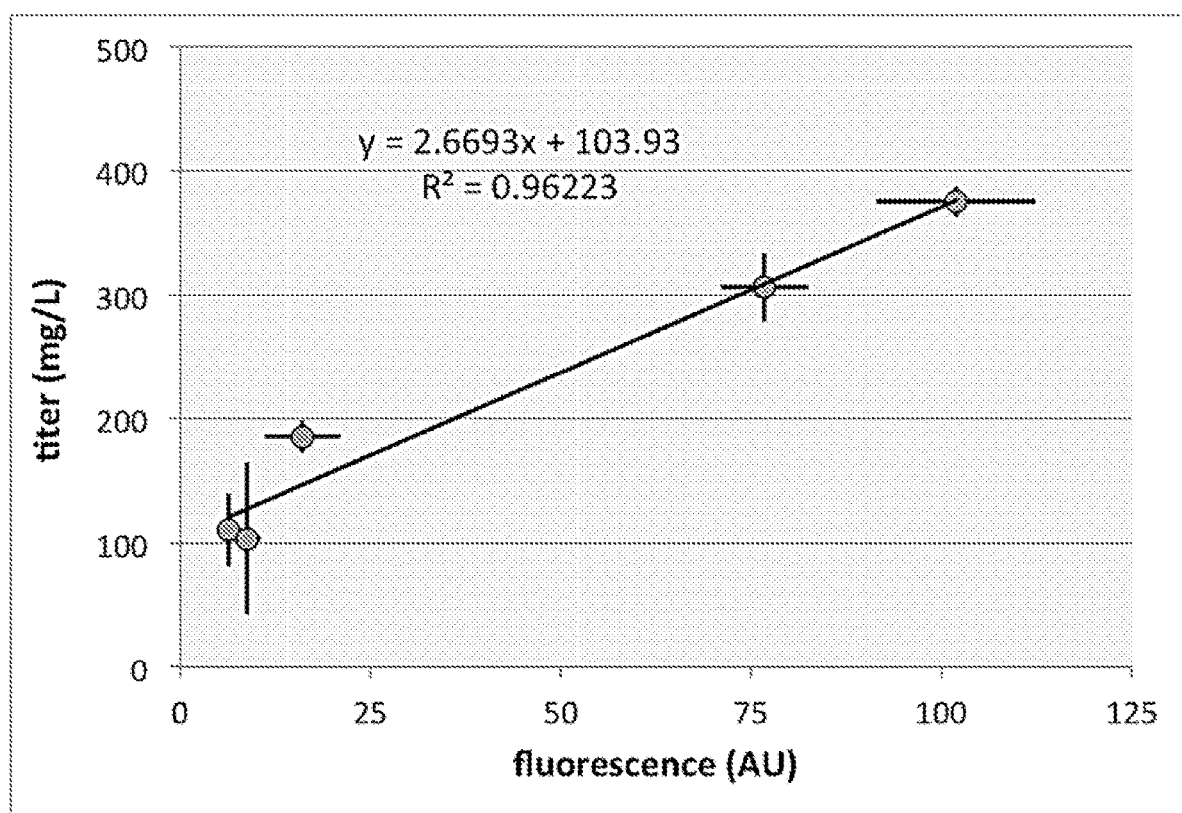

FIG. 22 is a graph depicting glucarate titer plotted as a function of biosensor output. Low fluorescence is a good indicator of low titer, while high fluorescence indicates high production titers.

Figure 23C:
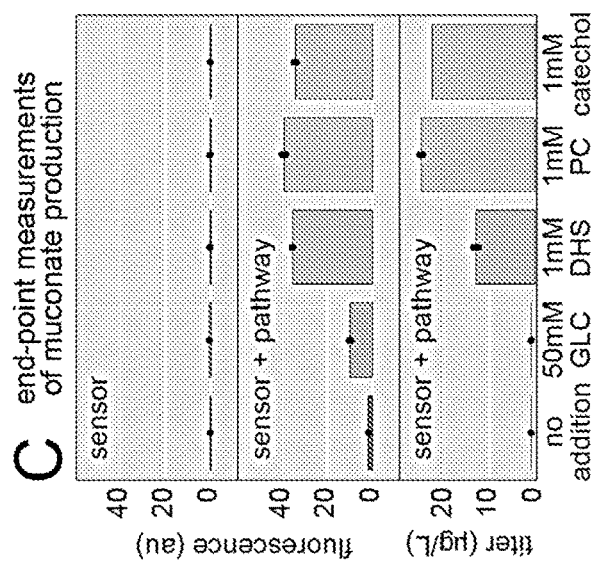
Figure 23B:
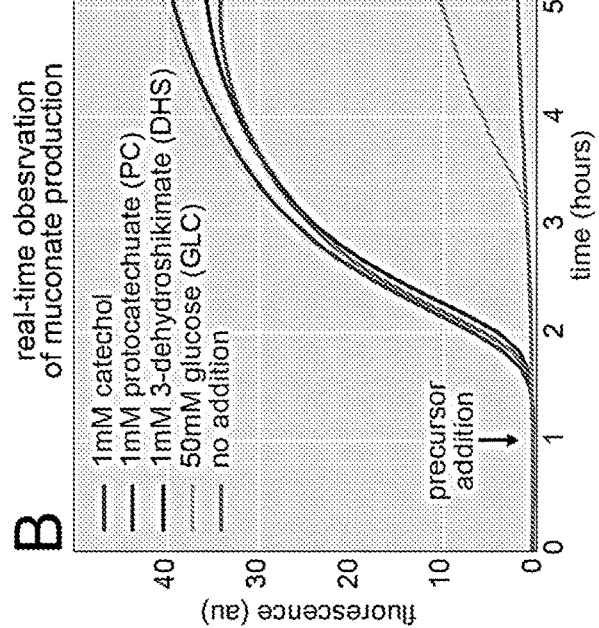
Figure 23A:
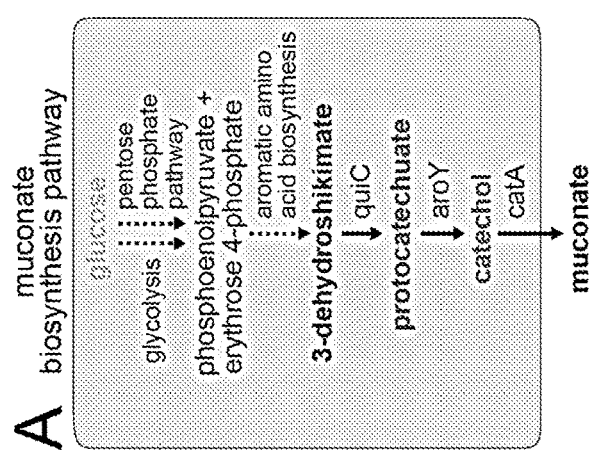

FIG. 23A, FIG. 23B and FIG. 23C depict real-time observation of muconate production. FIG. 23A is a schematic depicting that muconate is produced from glucose by expression of three heterologous enzymes. The committed step of muconate biosynthesis is the conversion of 3-dehydroshikimate (DHS) to protocatechuate (PC). FIG. 23B is a graph depicting that muconate pathway intermediates were added after one hour and fluorescence was monitored over time. Each late pathway intermediate activated the biosensor within an hour. Conversion of glucose to muconate was much slower (pink line). FIG. 23C is a graph depicting that end-point measurements of fluorescence reveal that the muconate biosynthesis pathway is necessary for biosensor activation by pathway intermediates (top panel). The presence of the pathway enables precursors to trigger the biosensor. Consistent with its place far upstream in the metabolic pathway, glucose is the only substrate that achieves lower fluorescence (pink bar—middle panel). Background fluorescence is observed without glucose (grey bar—middle panel). Muconate supernatant titers were determined by HPLC. Less muconate was produced by DHS (purple bar—bottom panel) than the subsequent intermediates (blue, green bars—bottom panel). Muconate production from glucose (pink bar—bottom panel) was below the limit of quantification by HPLC. Error bars and confidence bands represent the 95% confidence interval (n=3).

DETAILED DESCRIPTION

Aspects of the present disclosure are directed to the determination and/or observation of a target compound or metabolite production in a cell genetically modified to include a sensor (which may also be referred to herein as a "biosensor") and a reporter or detector system. The cell may also be genetically modified to include a pathway for production of the target compound or metabolite. The biosensor is a small-molecule inducible system producing a protein, such as a detectable protein, proportional to the amount of target compound or metabolite inside of the cell. The pathway consists of all the genes necessary to produce the target compound or metabolite from a desired starting point, typically a low-cost feedstock such as glucose or biomass. Rates of target compound or metabolite formation vary depending on the amount of intermediate supplied, the number of reactions leading from that intermediate to the final product, and how fast those reactions take place. Final titers depend on these factors as well as the amount of starting material that is shunted into side products or used for energy by the cell. Pathways for target compound or metabolite production are available in the literature or may be determined by those of skill in the art.

Embodiments of the present disclosure are directed to methods, systems and compounds useful for the identification of cells producing cellular metabolites using screening methods, such as fluorescence detection and measurement or selection methods, such as antibiotic resistance. Both screening and selection methods are contemplated as being useful to embodiments described herein. Fluorescent screening methods as described herein provide real-time observation of metabolite production. Increase or decrease of fluorescence can be observed over time and the increase or decrease of fluorescence is proportional to the amount of metabolite produced by the cell. According to one aspect, a cell is genetically modified to include one or more nucleic acids which when expressed produce a metabolite. The cell is genetically modified to include one or more nucleic acids which when expressed produce a sensor for the metabolite. The cell is genetically modified to include one or more nucleic acids which when expressed produce a reporter. Reporters within the scope of the present disclosure include those known to those of skill in the art. Reporters may provide light which can be detected. Reporters may be toxic to a cell leading to cell death when expressed. A sensor described herein may also be referred to as a biosensor. The terms are used interchangeably. The sensor, according to certain aspects, is an allosteric sensor. The sensor, according to certain aspects, is a regulator of, for example, fluorescent protein production or antidote or toxin production. According to one aspect where the reporter is a fluorescent molecule, presence of the metabolite within the cell causes the sensor to induce production of the fluorescent molecule which can be detected. According to one aspect, the amount or intensity of the detected fluorescence is proportional to the amount of metabolite produced by the cell. In this manner, cells that produce a greater amount of the metabolite can be identified, and optionally, isolated, and further optionally, grown, so that a population of cells having significant or desirable or increased metabolite production can be created. According to this aspect, sensors that can bind to or "sense" the presence of a metabolite and also regulate production of a fluorescent molecule can be used in high-throughput screening methods for cells that produce desired amounts of metabolites. The sensors are coupled to fluorescent reporter gene expression in methods of high-throughput single cell measurements or multiplexed identification of metabolite production resulting from genetic modification, using methods described, for example, in Dietrich, J. A., McKee, A. E. and Keasling, J. D. (2010) High-Throughput Metabolic Engineering: Advances in Small-Molecule Screening and Selection. *Annu Rev Biochem,* 79, 563-590 hereby incorporated by reference in its entirety.

According to aspects described herein, metabolite-responsive biosensors regulate fluorescent reporters and provide real-time observation of metabolite production and internal cell states.

According to certain aspects, methods are provided where gene expression is placed under control of target compound or metabolite concentration. A transcription factor binds to the promoter region of the gene to be controlled, either promoting or repressing the transcription of that gene. The transcription factor is in turn controlled by the binding of an effector molecule, such as a target compound or metabolite. When there is more effector molecule present, the transcription factor promotes transcription and more of the target protein is made. In simple cases, the effector molecule is the target compound or metabolite of interest and production of the target compound or metabolite of interest directly regulates the transcription factor. According to one aspect, the chemical of interest does not have a known transcription factor to which it binds. Accordingly, the target compound or metabolite is chemically or enzymatically transformed into a derivative molecule that is an effector molecule having a transcription factor. In this manner, production of the target compound or metabolite of interest indirectly regulates the transcription factor. However, regulation of the transcription factor is proportional to the amount of target compound or metabolite produced.

According to one aspect, methods are provided of using genetically encoded biosensors coupled to cellular fluorescence to identify metabolites. Genetically encoded biosensors link the expression of a fluorescent protein to the intracellular concentration of a target metabolite through the use of an allosteric transcription factor.

The fluorescent monitoring methods described herein utilize, for example, allosteric transcriptional regulators that are known for many common intermediates of metabolism, such as pyruvate (Ogasawara, H., Ishida, Y., Yamada, K., Yamamoto, K. and Ishihama, A. (2007) PdhR (pyruvate dehydrogenase complex regulator) controls the respiratory electron transport system in *Escherichia coli. J Bacteriol,* 189, 5534-55410), phosphoenol pyruvate (Cortay, J. C., Negre, D., Galinier, A., Duclos, B., Perriere, G. and Cozzone, A. J. (1991) Regulation of the Acetate Operon in *Escherichia-Coli*—Purification and Functional-Characterization of the Icir Repressor. *Embo J,* 10, 675-679), citrate (Martin, M. G., Magni, C., de Mendoza, D. and Lopez, P. (2005) CitI, a transcription factor involved in regulation of citrate metabolism in lactic acid bacteria. *J Bacteriol,* 187, 5146-5155), lactate (Gao, C., Hu, C. H., Zheng, Z. J., Ma, C. Q., Jiang, T. Y., Dou, P. P., Zhang, W., Che, B., Wang, Y. J., Lv, M. et al. (2012) Lactate Utilization Is Regulated by the FadR-Type Regulator LldR in *Pseudomonas aeruginosa. J Bacteriol,* 194, 2687-2692), unsaturated fatty acids (Henry, M. F. and Cronan, J. E. (1991) *Escherichia-coli* Transcription Factor That Both Activates Fatty-Acid Synthesis and Represses Fatty-Acid Degradation. *J Mol Biol,* 222, 843-849) and NADH (Wang, E., Bauer, M. C., Rogstam, A., Linse, S., Logan, D. T. and von Wachenfeldt, C. (2008) Structure and functional properties of the *Bacillus subtilis* transcriptional repressor Rex. *Mol Microbiol,* 69, 466-478). Genetically encoded biosensors within cells as described herein allow detection of production of a target compound, such as from glucose or other starting materials. Each cell expresses a fluorescent protein or other reporter at a rate proportional to its ability to produce the target compound thereby providing a method of screening for cells with desirable target compound production characteristics. Exemplary screening methods include flow-cytometry methods and those described in van Sint Fiet, S., van Beilen, J. B. and Witholt, B. (2006) Selection of biocatalysts for chemical synthesis. *Proceedings of the National Academy of Sciences of the United States of America,* 103, 1693-1698 or Dietrich, J. A., Shis, D. L., Alikhani, A. and Keasling, J. D. (2013) Transcription factor-based screens and synthetic selections for microbial small-molecule biosynthesis. *ACS synthetic biology,* 2, 47-58 each of which are hereby incorporated by reference in its entirety.

Sensor/Metabolite Pairs

According to certain aspects, known sensor/metabolite pairs can be used in the fluorescent monitoring methods described herein where the binding of the sensor to the metabolite results in production of fluorescent molecules by the cell. Exemplary known sensor/metabolite pairs include those shown in Table 1 below. Others are known in the art.

TABLE 1

| Sensor Gene | Molecule | Type of Sensor |
|---|---|---|
| cdaR | glucaric acid | Transcriptional activator |
| ttgR | naringennin (flavanoids) | Transcriptional repressor |
| btuB riboswitch | cobalamin | Riboswitch |
| mphR | macrolides | Transcriptional repressor |
| tetR | tetracycline derivates | Transcriptional repressor |
| benM | muconic acid | Transcriptional activator |
| alkS | medium chain n-alkanes | Transcriptional activator |
| xylR | xylose | Transcriptional activator |
| araC | Arabinose | Transcriptional activator |
| gntR | Gluconate | Transcriptional repressor |
| galS | Galactose | Transcriptional repressor |
| trpR | tryptophan | Transcriptional repressor |
| qacR | Berberine | Transcriptional repressor |
| rmrR | Phytoalexin | Transcriptional repressor |
| cymR | Cumate | Transcriptional repressor |
| melR | Melibiose | Transcriptional activator |
| rafR | Raffinose | Transcriptional activator |
| nahR | Salicylate | Transcriptional activator |
| nocR | Nopaline | Transcriptional activator |
| clcR | Chlorobenzoate | Transcriptional activator |
| varR | Virginiamycin | Transcriptional repressor |
| rhaR | Rhamnose | Transcriptional repressor |
| PhoR | Phosphate | Two-component system |
| MalK | Malate | Two-component system |
| GlnK | Glutamine | Two-component system |
| Retinoic acid receptor | Retinoic acid | Nuclear hormone receptor |
| Estrogen receptor | Estrogen | Nuclear hormone receptor |
| Ecdysone receptor | Ecdysone | Nuclear hormone receptor |

According to certain aspects described herein, sensor/metabolite pairs can be selected based upon the following considerations: (1) the relationship between stimulus strength and circuit activation; (2) the response time of the biosensor to a stimulus; (3) the heterogeneity of biosensor activation between cells in an isogenic population and/or (4) the cross-reactivity with stimuli of other biosensors. Exemplary biosensors are useful DNA binding proteins having a cognate promoter/operator and that are induced by a target compound such as a metabolite that can be produced enzymatically through metabolic engineering.

It is to be understood that the examples of sensors and their corresponding metabolite binding partners are exemplary only and that one of skill in the art can readily identify additional sensors and their corresponding metabolite binding partners for use in the present disclosure. The transformed microorganism is intended to express the sensors and the metabolite under suitable conditions.

The biosynthetic pathways for production of any particular metabolite binding partner are known to those of skill in the art. The sensor sequence is known to those of skill in the art, such as being based on a published literature search. For example, biosynthetic pathways for the above metabolite binding partners and sensors are fully described in the following: cdaR (Monterrubio et al. 2000 J. Bacteriol 182 (9):2672-4), tetR (Lutz and Bujard Nucleic Acids Res. 1997 25(6):1203-10), alkS (Canosa et al. Mol Micriobiol 2000 35(4):791-9), ttgR (Teran, et al. Antimicrob Agents Chemother. 47(10):3067-72 (2003)), btuB riboswitch (Nahvi, et al. Nucleic Acids Res. 32:143-150 (2004)); glucaric acid (Moon, et al. Appl Env Microbiol. 75:589-595 (2009)), naringenin (Santos, et al. Metabolic Engineering. 13:392-400 (2011)), alkanes (Steen, et al. 463:559-562 (2009)), cobalamin (Raux, et al. Cell Mol Life Sci. 57:1880-1893. (2000)), muconic acid (Niu, et al. Biotechnol Prog. 18:201-211. (2002)) each of which are hereby incorporated by reference in its entirety. Methods described herein can be used to insert the nucleic acids into the genome of the microorganism that are responsible for production of sensors and metabolite binding partners.

According to certain aspects, a cell can be genetically engineered or modified to include one or more nucleic acids which when expressed produce one or more target compounds or target metabolites. According to certain aspects, a cell can be genetically engineered or modified to include one or more nucleic acids which when expressed produce one or more sensor molecules. According to certain aspects, a cell can be genetically engineered or modified to include one or more nucleic acids which when expressed produce one or more reporter molecules or systems.

According to certain aspects, a cell can be genetically engineered or modified to include one or more nucleic acids which when expressed produce one or more target compounds or target metabolites, one or more nucleic acids which when expressed produce one or more sensor molecules, and/or one or more nucleic acids which when expressed produce one or more reporter molecules or systems.

According to certain aspects, a cell can be genetically engineered or modified to include one or more nucleic acids which when expressed produce a plurality of target compounds or target metabolites, one or more nucleic acids which when expressed produce a plurality of sensor molecules, and/or one or more nucleic acids which when expressed produce a plurality of reporter molecules or systems. According to one aspect, the reporter molecule or molecules can be a fluorescent molecule(s) with a specific fluorescent molecule being representative for a given metabolite or metabolites.

According to certain aspects, a cell can be genetically engineered or modified to express a plurality of metabolites and a corresponding plurality of sensor molecules. The cell can also be genetically engineered or modified to express a plurality of fluorescent molecules, with a specific fluorescent molecule being representative for a given metabolite or metabolites. According to one aspect, each metabolite has a corresponding unique fluorescent molecule, so that different fluorescent molecules can be detected indicating that different metabolites are being produced by the cell. According to this aspect, each sensor is orthogonal to other sensors, and to other common inducible systems. A single cell can be genetically modified to express different metabolites, with each metabolite being detected by a corresponding different fluorescent molecule.

Standard recombinant DNA and molecular cloning techniques used herein are well known in the art and are described in Sambrook, J., Fritsch, E. F. and Maniatis, T., *Molecular Cloning: A Laboratory Manual*, $2^{nd}$ ed.; Cold Spring Harbor Laboratory: Cold Spring Harbor, N.Y., (1989) and by Silhavy, T. J., Bennan, M. L. and Enquist, L. W., *Experiments with Gene Fusions*; Cold Spring Harbor Laboratory: Cold Spring Harbor, N.Y., (1984); and by Ausubel, F. M. et. al., *Current Protocols in Molecular Biology*, Greene Publishing and Wiley-Interscience (1987) each of which are hereby incorporated by reference in its entirety.

Additional useful methods are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992) each of which are hereby incorporated by reference in its entirety.

Microorganisms may be genetically modified to delete genes or incorporate genes by methods known to those of skill in the art. Vectors and plasmids useful for transformation of a variety of host cells are common and commercially available from companies such as Invitrogen Corp. (Carlsbad, Calif.), Stratagene (La Jolla, Calif.), New England Biolabs, Inc. (Beverly, Mass.) and Addgene (Cambridge, Mass.).

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression in Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts.

Certain vectors are capable of replicating in a broad range of host bacteria and can be transferred by conjugation. The complete and annotated sequence of pRK404 and three related vectors-pRK437, pRK442, and pRK442(H) are available. These derivatives have proven to be valuable tools for genetic manipulation in Gram-negative bacteria (Scott et al., Plasmid 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., *J. Bacteriol.* 174(17):5633-5638 (1992)). Additionally, in vitro transposomes are available to create random mutations in a variety of genomes from commercial sources such as EPICENTRE® (Madison, Wis.).

Vectors useful for the transformation of *E. coli* are common and commercially available. For example, the desired genes may be isolated from various sources, cloned onto a modified pUC19 vector and transformed into *E. coli* host cells. Alternatively, the genes encoding a desired biosynthetic pathway may be divided into multiple operons, cloned onto expression vectors, and transformed into various *E. coli* strains.

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAM.beta.1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (van Kranenburg R, Golic N, Bongers R, Leer R J, de Vos W M, Siezen R J, Kleerebezem M. *Appl. Environ. Microbiol.* 2005 March; 71(3): 1223-1230), which may be used for transformation.

Initiation control regions or promoters, which are useful to drive expression of the relevant pathway coding regions in the desired *Lactobacillus* host cell, may be obtained from *Lactobacillus* or other lactic acid bacteria, or other Gram-positive organisms. A non-limiting example is the nisA promoter from *Lactococcus*. Termination control regions may also be derived from various genes native to the preferred hosts or related bacteria.

The various genes for a desired biosynthetic or other desired pathway may be assembled into any suitable vector or vectors, such as those described above. A single vector need not include all of the genetic material encoding a complete pathway. One or more or a plurality of vectors may be used in any aspect of genetically modifying a cell as described herein. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (*Molecular Genetics and Genomics* 224:1252-154 (1990)), Bringel and Hubert (*Appl. Microbiol. Biotechnol.* 33: 664-670 (1990)), and Teresa Alegre, Rodriguez and Mesas (*FEMS Microbiology Letters* 241:73-77 (2004)). Plasmids can also be introduced to *Lactobacillus plantatrum* by conjugation (Shrago, Chassy and Dobrogosz *Appl. Environ. Micro.* 52: 574-576 (1986)). The desired biosynthetic pathway genes can also be integrated into the chromosome of *Lactobacillus* using integration vectors (Hols et al. *Appl. Environ. Micro.* 60:1401-1403 (1990); Jang et al. *Micro. Lett.* 24:191-195 (2003)).

Microorganisms which may serve as host cells and which may be genetically modified to produce recombinant microorganisms as described herein may include one or members of the genera *Clostridium, Escherichia, Rhodococcus, Pseudomonas, Bacillus, Lactobacillus Saccharomyces*, and *Enterococcus*. Particularly suitable microorganisms include *Escherichia coli, Bacillus subtilis*, and *Saccharomyces cerevisiae*.

Methods for Screening Cells Using a Reporter

Methods described herein utilize the detection and measurement of detectable reporters expressed by cells. Exemplary detectable reporters include fluorescent molecules or fluorescent proteins. Exemplary fluorescent reporters include those identified in Shaner et al., Nature methods, Vol. 2, No. 12, pp. 905-909 (2005) hereby incorporated by reference in its entirety. An exemplary list of fluorescent reporters known to those of skill in the art includes mPlum, mCherry, tdTomato, mStrawberry, J-Red, DsRed-monomer, mOrange, mKO, mCitrine, Venus, YPet, EYFP, Emerald, EGFP, CyPet, mCFPm, Cerulean and T-Sapphire, and the like.

Exemplary non-fluorescent, but light emitting reporters include luciferase and its derivatives such as those disclosed in Thorne et al., Chemistry and Biology, vol. 17, issue 6, pp. 646-657 (2010) hereby incorporated by reference in its entirety. An exemplary list of non-fluorescent reporter known to those of skill in the art include Firefly (FLuc), modified firefly (Ultra-Clo), Click beetle (CBLuc), Sea pansy (RLuc), Copepod crustacean (GLuc), Ostracod crustacean (CLuc) and the like.

Genetically encoded biosensors link intracellullar metabolite levels to fluorescent protein expression and enable fluorescence-based screens. Combined with fluorescent activated cell sorting (FASC), biosensor-based screens can provide evaluation rates of up to $1 \times 10^9$ designs per day. According to certain aspects, any method for evaluating cellular fluorescence is envisioned. Groups of cells can be evaluated with fluorescent plate readers in 96 or 384-well plates and is useful for prototyping the screening system. Flow cytometry can be used to evaluate millions of cells individually. Fluorescent activated cell sorting can be used to isolate the cells with the highest fluorescence. These highly fluorescent cells will be producing the highest amounts of target compounds or metabolites. These cells can be used for the next round of design or chosen for a commercial production system.

Methods of detecting and/or measuring fluorescent cells include fluorescence activate cell sorting, such as described in Herzenberg et al., Clin. Chem. 2002 October; 48(10): 1819-27 hereby incorporated by reference in its entirety. Further methods include microscopy, such as where a large number of cells can be viewed using microscopy and the fluorescence cells can be identified and selected and separated or the non-fluorescence cells can be destroyed selectively. Further methods include microtiter plate assays, for example where screening by fluorescence cis done robotically in microtiter plates, such as 1536-well plates or 9600 well plates. Such methods may be combined with robotic handling and advanced plate readers typical of high throughput screening. Further methods include emulsion assays, for example, where cells can be trapped within emulsions and assayed using microfluidics, such as described in Wang et al., Nature Biotechnology, Volume 32, pp. 473-478 (2014) hereby incorporated by reference in its entirety. Other microfluidic assays can be used to evaluate cells such as those described in Guo et al., Lab Chip, 2012, 12, 2146-2155 hereby incorporated by reference in its entirety.

Other methods and assays which do not rely on fluorescent or light emitting reporters can be used to detect cells according to the methods described herein. Such methods include those that use transcription but not necessarily fluorescence or luminescence. Exemplary methods include pull-down assays, such as where transcriptional readout drives production of a cell surface marker which makes the cell stick to a surface thus retaining only cells with high metabolite production capabilities. Further methods include luciferase high-throughput screening such as described in Fan et al., ASSAY and Drug Development Technologies, Volume 5, Number 1, pp. 127-136 (2007) hereby incorporated by reference in its entirety.

Methods for Selecting Cells Using an Antidote/Toxin System

Selection methods according to the present disclosure using a sensor and its binding metabolite allow cells exhibiting a particular phenotype to live. Methods described herein utilize antidote/toxin systems for selecting cells which produce an antidote to a toxin in response to a target compound or metabolite. Selection for cells producing high amounts of the target compound or metabolite is accomplished by treating a population of cells (typically up to 10 billion) with an antibiotic. Cells will only be able to survive if they produce the antidote in response to high amounts of the target compound or metabolite. Cells that produce the highest amounts of the target compound or metabolite will grow faster than cells producing slightly lower amounts of the target compound or metabolite and will take over the population. The result is a new culture of cells that excel at producing the target compound or metabolite. According to certain aspects, a microorganism is genetically modified to include one or more exogenous nucleic acids encoding an antidote to a toxin. Antidote and toxin pairs are known to those of skill in the art and include SDS:tolC, colicin:tolC (negative selection), kanamycin:kanamycin nucleotidyltransferase, chloramphenicol:chloramphenicol acyl transferase, ampicillin:beta lactamase, tetracycline:tetracycline efflux pump tetA, nickel chloride:tetracycline efflux pump tetA (negative selection), 5-fluoroorotic acid:URA3 (negative selection). The transformed microorganism is intended to express the antidote under suitable conditions.

The genes for production of any particular antidote are known to those of skill in the art. For example, the genes for the above antidotes are fully described in tetA (Postle et al. Nucleic Acid Research 1984 12(12)4849-4863) tolC (Fralick J. Bacteriol 1996 178(19)5803-5805) Chloramphenicol acetyl tranferase (Shaw et al. J Bacteriol. 1970 104(3):1095-1105). Methods described herein can be used to insert the nucleic acids into the genome of the microorganism that are responsible for production of DNA binding molecules and metabolite binding partners.

According to one aspect, the transformed, recombinant microorganism expresses the sensor which regulates production of the antidote. When expressed, the sensor prevents the cell from expressing the antidote gene, either by blocking the expression (i.e. a repressor) or failing to activate the expression (i.e. activator) of the antidote unless the sensor is bound by the target metabolite, which leads to antidote expression by changing sensor function. Several regulation mechanisms are possible: for an allosteric transcription factor that is a repressor, the repressor protein blocks transcription of the antidote gene by binding a region of DNA 5' to the antidote gene unless the desired metabolite binds the repressor; for an allosteric transcription factor that is an activator, the activator recruits RNA polymerase to a region of DNA 5' to the antidote gene only when the desired metabolite binds to the activator; for an attenuating riboswitch, the riboswitch is encoded in the 5' untranslated region of a repressor regulating the transcription of the antidote gene, and attenuates translation of this repressor when bound to the target metabolite. According to a further aspect, the transformed, recombinant microorganism expresses the biosynthetic genes that produce the metabolite which binds to the sensor in a manner to promote production of the antidote. According to one aspect, the production of the antidote is proportional to the amount of metabolite binding partner that is produced by the microorganism and bound to sensor. In the absence of the metabolite, the sensor prevents production of antidote. Many individual sensor molecules are expressed in the cell. The binding of the metabolite to a sensor molecule is a reversible event, and switches that individual sensor molecule from a state in which it prevents antidote expression to a state in which it allows antidote expression. When the concentration of metabolite is low, the proportion of the sensor molecules bound to metabolite is low at any given time, hence the antidote is not expressed or expressed only slightly. As the concentration of metabolite increases, the proportion of sensor molecules bound to metabolite increases, which results in higher expression of antidote. This gives rise to dose-dependence of the antidote production and metabolite level. That is, the more metabolite binding partner that is produced by the cell, the higher the proportion of sensor molecules bound to metabolite molecules the cell to produce more antidote. The metabolite concentration below which there is no production of antidote is the detection threshold, and the metabolite concentration above which there is no further production of the antidote is the saturation point; these limits give rise to the dynamic range of the sensor-antidote system.

The following examples are set forth as being representative of the present disclosure. These examples are not to be construed as limiting the scope of the present disclosure as these and other equivalent embodiments will be apparent in view of the present disclosure, figures and accompanying claims.

Example I

Chemicals and Reagents

All reagents were obtained from Sigma (St. Louis, Mo.) unless otherwise noted. Antibiotics and IPTG were obtained from Gold Biotechnology (St. Louis, Mo.). Anhydrotetracycline (aTC) was obtained from Clontech (Mountain View, Calif.). Polymerase chain reaction (PCR) mix was purchased from Kapa Biosystems (Wilmington, Mass.). Erythromycin and aTC were dissolved in ethanol while naringenin was dissolved in dimethyl sulfoxide. All other inducers were dissolved in deionized water.

Example II

Plasmid Construction

Plasmids were constructed using Gibson isothermal assembly methods (see Gibson, D. G., Young, L., Chuang, R. Y., Venter, J. C., Hutchison, C. A., 3rd and Smith, H. O. (2009) Enzymatic assembly of DNA molecules up to several hundred kilobases. *Nat Methods,* 6, 343-345 incorporated herein by reference in its entirety) and transformed into DH5α electrocompetent cells (New England Biolabs, Ipswich Mass.). All standard induction plasmids contained the rrnB strong terminator (see Orosz, A., Boros, I. and Venetianer, P. (1991) Analysis of the complex transcription termination region of the *Escherichia coli* rrnB gene. *European journal of biochemistry/FEBS,* 201, 653-659 incorporated herein by reference in its entirety) followed by the inducible promoter and the strong g10 RBS (see Olins, P. O., Devine, C. S., Rangwala, S. H. and Kavka, K. S. (1988) The T7 phage gene 10 leader RNA, a ribosome-binding site that dramatically enhances the expression of foreign genes in *Escherichia coli. Gene,* 73, 227-235 incorporated herein by reference in its entirety) 'tttaactttaagaaggagatatacat,' (SEQ ID NO:1) driving the expression of sfGFP (see Pedelacq, J. D., Cabantous, S., Tran, T., Terwilliger, T. C. and Waldo, G. S. (2006) Engineering and characterization of a superfolder green fluorescent protein. *Nature biotechnology,* 24, 79-88 incorporated herein by reference in its entirety) (except in the case of CdaR which used the native RBS). GFP was followed by a transcriptional terminator prefixing the proB promoter (see Davis, J. H., Rubin, A. J. and Sauer, R. T. (2011) Design, construction and characterization of a set of insulated bacterial promoters. *Nucleic acids research,* 39, 1131-1141 incorporated herein by reference in its entirety) and strong RBS 'gaaataaggaggtaatacaa,' (SEQ ID NO:2) which facilitated expression of the transcriptional regulator. Each inducible system was implemented on high and low copy plasmids. High copy pJKR-H plasmids were constructed with the pUC origin and beta lactamase antibiotic resistance marker derived from pUC19 (New England Biolabs, Ipswich Mass.). Low copy pJKR-L plasmids were constructed in the same way, except that the pUC origin was replaced by the SC101 origin (including repA) from pSC101 obtained from American Type Culture Collection (ATCC #37032). In the case of the MphR inducible system, the eryR erythromycin resistance cassette was included as well. The sequences of the transcriptional regulators and their cognate promoters are provided in Table 2. The plasmids MphR-p15a-SPEC-mCherry and AcuR-colA-KAN-CFP were designed for compatible maintenance with pJKR-H-CdaR. In both these plasmids the antibiotic resistance gene and origin of replication were replaced with p15a-aadA and colA-kanR. Sequence and organism names for each of the MIOX enzymes are provided in Table 3. Each enzyme was cloned downstream of the constitutive promoter P2 (see Mutalik, V. K., Guimaraes, J. C., Cambray, G., Lam, C., Christoffersen, M. J., Mai, Q. A., Tran, A. B., Paull, M., Keasling, J. D., Arkin, A. P. et al. (2013) Precise and reliable gene expression via standard transcription and translation initiation elements. *Nat Methods,* 10, 354-360 hereby incorporated by reference in its entirety) and g10 RBS to create pJKR-MIOX variants. These expression plasmids used the colA origin of replication and kanamycin resistance gene for maintenance. Sequences and plasmids are available on Addgene (plasmid numbers 62557-62570).

Example III

Induction and Toxicity

DH5α cells transformed with pJKR plasmids and maintained with carbenicillin were used in the induction assays. For each induction evaluation experiment, the cells were grown overnight to saturation before being diluted 1:100 into fresh LB media and incubated at 200 RPM and 37° C. After four hours, 150 µl of the log-phase cells were transferred to 96-well plates and stock inducer was added to achieve the desired range of induction concentrations. Three separate wells were inoculated and independently supplemented with the appropriate amount of inducing chemical for each level of induction. Measurements were made on the same Biotek (Winooksi, Vt.) HT plate reader using the same settings: excitation 485/20, emission 528/20, 37° C. and fast shaking. Fluorescence and absorbance were measured every 10 minutes for 15 hours. Fluorescence was measured in arbitrary units (AFU) while optical density was determined by absorbance (OD). Normalized fluorescence was determined by dividing fluorescence by optical density for a given measurement. Five independent wells containing control strains, transformed with pUC19, were included to provide a measurement of background autofluorescence. The same protocol modified to observe fluorescence after 90 minutes was used to evaluate induction of the TtgR biosensor with phenol and related compounds.

The ratio of fluorescence to absorbance at 600 nm was used in order to compensate for changes in cell density over time and between experiments (AFU/OD). Normalized fluorescence at the 15$^{th}$ hour was used to determine the relationship between inducer concentration and fluorescent response. This transfer function is plotted on a log-log scale in FIG. 1A and FIG. 1B to capture the wide range of inducer concentrations and resulting fluorescence values. The Mathematica Hypothesis Testing Package function MeanCI was used to calculate the 95% confidence interval of the estimated mean based upon a Student's t-distribution derived from the three induction replicates. Time-courses of cell growth and biosensor activation were normalized and plotted with the Python module Seaborn using bootstrapping to produce 95% confidence intervals for the standard error of the sample mean (assuming a normal error distribution) for the three independently induced replicates (see FIG. 2, FIG. 10 and FIG. 11). For visualization purposes, normalization was performed on the fluorescence time-course data by dividing all data in a graph by 110% of the highest value such that the trends in each graph can be observed on a common axis. For visualization purposes, growth time-course data was normalized such that each growth curve was divided by its mid-point value and offset to zero at time zero.

Induction ratios were determined after 15 hours of induction. Standard error of the derived fold-induction value was determined from the standard error of the mean (assuming a normal error distribution) for the induced, uninduced and control sample means such that the standard error of fold-induction is:

$$\sigma_F = \bar{F}\sqrt{\frac{\sigma_I^2 + \sigma_C^2}{\bar{I}_B^2} + \frac{\sigma_U^2 + \sigma_C^2}{\bar{U}_B^2}}$$

$\bar{F}$ is the mean magnitude of the fold induction, $\sigma_I$, $\sigma_U$ and $\sigma_C$ are the SEM for the fluorescence of induced, uninduced and control cells, while $\bar{I}_B$ and $\bar{U}_B$ are the mean fluorescence of the induced and uninduced cells with mean background fluorescence subtracted. For cases where the mean fluorescence of the uninduced cells was within the background fluorescence of the strain, a lower bound on the fold-induction was determined by dividing the 95% confidence interval lower bound of $\bar{I}_B$ by the 95% confidence interval upper bound of $\bar{U}_B$. The range of the 95% confidence interval was approximated by doubling the standard error of the background-subtracted fluorescence.

Toxicity of the inducer chemicals and their solvents were determined at each of the concentrations evaluated for induction response. In these experiments, DH5α cells were diluted 1:100 from overnight growth into fresh selective LB and grown for 2 hours at 200 RPM and 37° C. pUC19 was used as a control plasmid in each case except for the erythromycin evaluation in which pJKR-H-MphR was used to provide eryR expression. 150 µl of cells were transferred into 96-well plates and the assayed chemical was immediately added in triplicate before further incubation at 600 RPM and 37° C. After 15 hours the absorbance at 600 nm was measured and normalized to the absorbance observed in the control wells in which no chemical was added the cells.

The cross-reactivity matrix was determined by inducing cells that contained target and off-target biosensors. The cells were prepared and evaluated in the same way as described in the induction evaluation experiments. The following inducer concentrations were used: acrylate (5 mM), arabinose (165 µM), glucarate (4.4 mM), erythromycin (37 µg/ml), naringenin (9 mM), IPTG (1 mM), rhamnose (10 mM), cumate (20 µM), DMSO (1%), ethanol (1%).

Example IV

Mathematical Modeling

The GFP expression rate was calculated at each time-point with the formula ΔGFP/OD. Scipy was used to perform a non-linear least-squares fit of the maximum GFP expression rate to the corresponding inducer concentration using the Hill function $$\left(\frac{\Delta GFP}{\Delta t}\right)_{max} = V_{max} \cdot \frac{I^h}{I^h + K_L^h} + V_{min}$$

$V_{max}$ is the maximum rate of GFP expression, $V_{min}$ is basal rate of GFP expression, I is the concentration of inducer, h is the hill coefficient and $K_L$ is the lumped half-maximal parameter described in Results. The variance of each parameter was determined from the least-squares covariance matrix. The square of the variance is the parameter error reported in Table 4 below.

TABLE 4

| | Copy Number | Fold Induction | Hill Coefficient | Half Maximal Parameter | | Max Expression Velocity (s$^{-1}$) | Basal Expression Velocity (s$^{-1}$) |
|---|---|---|---|---|---|---|---|
| AcuR | High | >90 | 3.2 ± 0.3 | 2.6 ± 0.1 | mM | 910 ± 40 | 5 ± 7 |
| | Low | >50 | 1.3 ± 0.1 | 1.0 ± 0.1 | mM | 150 ± 10 | 15 ± 2 |
| AraC | High | 210 ± 9 | 1.3 ± 0.1 | 59 ± 3 | µM | 3150 ± 60 | 20 ± 50 |
| | Low | 29 ± 3 | 1.3 ± 0.2 | 250 ± 30 | µM | 1260 ± 50 | 40 ± 30 |
| CdaR | High | 168 ± 6 | 1 ± 0.1 | 490 ± 60 | µM | 2600 ± 100 | 0 ± 60 |
| | Low | 78 ± 8 | 1 ± 0.2 | 8 ± 2 | mM | 1000 ± 100 | 30 ± 20 |
| MphR | High | 108 ± 9 | 1.6 ± 0 | 97 ± 2 | µM | 2070 ± 20 | 9 ± 7 |
| | Low | 8 ± 1 | 1.6 ± 0.1 | 22 ± 1 | µM | 66 ± 1 | 5 ± 0.4 |
| TetR | High | 63 ± 3 | 4.2 ± 0.1 | 81 ± 1 | nM | 1760 ± 10 | 8 ± 6 |
| | Low | >50 | 3.1 ± 0.3 | 54 ± 2 | nM | 116 ± 2 | 2 ± 1 |
| TtgR | High | 70 ± 20 | 3.8 ± 0.6 | 550 ± 50 | µM | 180 ± 6 | 4 ± 3 |
| | Low | 3 ± 0 | 2.3 ± 0.4 | 190 ± 20 | µM | 25 ± 1 | 6 ± 1 |

Points in FIG. 3 and FIG. 12 reflect the mean of three independently induced replicates with error bars corresponding to the 95% confidence interval determined for the standard error of the mean by bootstrapping. Lines reflect the model fitted to the data.

Example V

Flow Cytometry

D5Hα cells containing the plasmid to be evaluated were grown to saturation overnight and diluted 1:100 in 1 mL of selective LB media and incubated in 96-well deep well blocks at 900 RPM and 37° C. After 4 hours, inducers were added to the desired final concentration and incubation was resumed for 15 hours. Induced cultures were diluted 1:100 in cold phosphate buffered saline (PBS) and kept on ice until evaluated on the LSRFortessa flow cytometer (BD Biosciences, San Jose, Calif.). At least 100,000 events were captured for each sample. Gating was performed on forward and side scatter to avoid debris and clumped cells. Data was exported to FloJo for visualization and Mathematica for subsequent analysis.

Cells that were transformed with pJKR-H-CdaR, MphR-p15a-SPEC-mCherry (designated pJKR-O-MphR) and AcuR-colA-KAN-CFP (designated pJKR-O-AcuR) were maintained in LB with all three antibiotics. The cells were induced in the same manner as above with induction concentrations of 5 mM acrylate, 40 mM glucarate and 37 µg/mL erythromycin. Collection and gating were performed as above. 10,000 events were plotted in FIG. 7.

Example VI

Glucarate Production

For observation of glucarate production via fluorescence, BL21 DE3 (New England Biolabs, Ipswich Mass.) cells that were doubly transformed with pJKR-H-CdaR and pJKR-MIOX were diluted 1:100 from saturated culture into carbenicillin and kanamycin selective LB. After 4 hours the cells were transferred to 96-well plates in triplicate and 50 mM myo-inositol was added to the media. Fluorescence and absorbance (600 nm) were measured with a Biotek HT plate reader in 15-minute intervals for 48 hours with fast shaking at 37° C.

In order to directly measure glucarate titers, BL21 DE3 cells transformed with pJKR-MIOX variants were prepared as above, except for production took place in 1 mL cultures within 96-well deep well blocks incubating at 900 RPM and 37° C. for 48 hours. Supernatants were collected via centrifugation and filtration and glucarate was determined by mass spectrometry Example VII Identification of Metabolites by Fluorescent Reporter The following sensors were studied: AcuR, CdaR, MphR and TtgR. AcuR binds acrylate in order to regulate dimethylsulfoniopropionate (DMSP) catabolism in *Rhodobacter sphaeroides* (see Sullivan, M. J., Curson, A. R., Shearer, N., Todd, J. D., Green, R. T. and Johnston, A. W. (2011) Unusual regulation of a leaderless operon involved in the catabolism of dimethylsulfoniopropionate in *Rhodobacter sphaeroides*. *PloS one*, 6, e15972). CdaR is a transcriptional activator from *E. coli* that has been shown to regulate transcription in response to several diacids: glucarate, galactarate and glycerate (see Monterrubio, R., Baldoma, L., Obradors, N., Aguilar, J. and Badia, J. (2000) A common regulator for the operons encoding the enzymes involved in D-galactarate, D-glucarate, and D-glycerate utilization in *Escherichia coli*. *J Bacteriol*, 182, 2672-2674.) MphR mediates transcription in the presence of erythromycin and other macrolide antibiotics such as josamycin and azithromycin (see Noguchi, N., Takada, K., Katayama, J., Emura, A. and Sasatsu, M. (2000) Regulation of transcription of the mph(A) gene for macrolide 2'-phosphotransferase I in *Escherichia coli*: characterization of the regulatory gene mphR(A). *J Bacteriol*, 182, 5052-5058.) MphR was first identified in a macrolide resistant strain of *E. coli* and has subsequently been used in both mammalian (see Kramer, B. P., Viretta, A. U., Daoud-El-Baba, M., Aubel, D., Weber, W. and Fussenegger, M. (2004) An engineered epigenetic transgene switch in mammalian cells. *Nature biotechnology*, 22, 867-870 and Weber, W., Fux, C., Daoud-el Baba, M., Keller, B., Weber, C. C., Kramer, B. P., Heinzen, C., Aubel, D., Bailey, J. E. and Fussenegger, M. (2002) Macrolide-based transgene control in mammalian cells and mice. *Nature biotechnology*, 20, 901-907) and microbial (see Mohrle, V., Stadler, M. and Eberz, G. (2007) Biosensor-guided screening for macrolides. *Analytical and bioanalytical chemistry*, 388, 1117-1125) transgene activation. In *Pseudomonas putida*, TtgR regulates expression of a multi-drug efflux pump in response to flavonoids such as naringenin, phloretin and genistein (see Teran, W., Felipe, A., Segura, A., Rojas, A., Ramos, J. L. and Gallegos, M. T. (2003) Antibiotic-dependent induction of *Pseudomonas putida* DOT-T1E TtgABC efflux pump is mediated by the drug binding repressor TtgR. *Antimicrobial agents and chemotherapy*, 47, 3067-3072), and has also been used for mammalian transgene activation (see Rossger, K., Charpin-El-Hamri, G. and Fussenegger, M. (2013) A closed-loop synthetic gene circuit for the treatment of diet-induced obesity in mice. *Nature communications*, 4, 2825.) AcuR, MphR and TtgR are members of the TetR transcriptional repressor family. The regulators TetR and AraC are included for comparison.

Biosensors were constructed as a single plasmid encoding both the allosteric transcriptional regulator and a fluorescent reporter. The reporter mRNA is transcribed from a promoter/operator sequence controlled by the allosteric transcriptional regulator. For transcriptional repressors, a medium-strength constitutive promoter (see Davis, J. H., Rubin, A. J. and Sauer, R. T. (2011) Design, construction and characterization of a set of insulated bacterial promoters. *Nucleic acids research*, 39, 1131-1141) was used to drive regulator transcription. For the transcriptional activators, the native promoter sequence of the activator was used in order to preserve the auto-regulating behavior of the AraC and CdaR regulators (see Monterrubio, R., Baldoma, L., Obradors, N., Aguilar, J. and Badia, J. (2000) A common regulator for the operons encoding the enzymes involved in D-galactarate, D-glucarate, and D-glycerate utilization in *Escherichia coli*. *J Bacteriol*, 182, 2672-2674 and Hahn, S. and Schleif, R. (1983) In vivo regulation of the *Escherichia coli* araC promoter. *J Bacteriol*, 155, 593-600. The biosensors were constructed in commonly used high and low copy plasmids to evaluate their behavior in different contexts. High copy plasmids employed a pUC origin of replication (~100-500 copies), while the low copy plasmids encoded the SC101 replication origin (2-5 copies). All plasmids expressed beta-lactamase, enabling the use of carbenicillin for plasmid maintenance. In the case of the MphR biosensor, an erythromycin resistance gene was also included to protect the cells from the high macrolide concentrations required for induction.

Figure 1A:
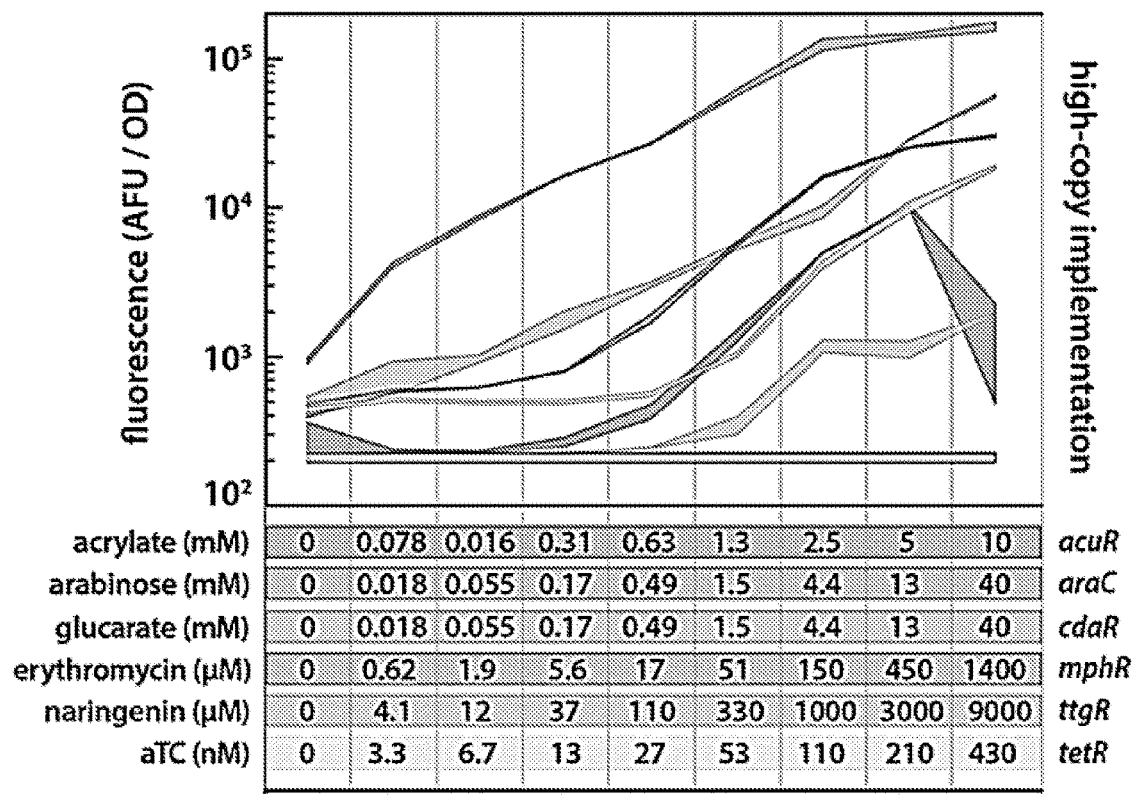
FIG. 1A and FIG. 1B depict induction dynamics for inducible systems. The relationship between fluorescent response and inducer concentration is represented as a 95% confidence band (n=3) for both the high-copy (FIG. 1A) and low-copy (FIG. 1B) implementations of the inducible systems. The plots are log scale to capture the wide range of inducer concentrations and biosensor responses. Inducer concentrations are the same for both high and low-copy implementations. Each curve is matched to a color-coded table of inducer concentration ranges.
Figure 1B:
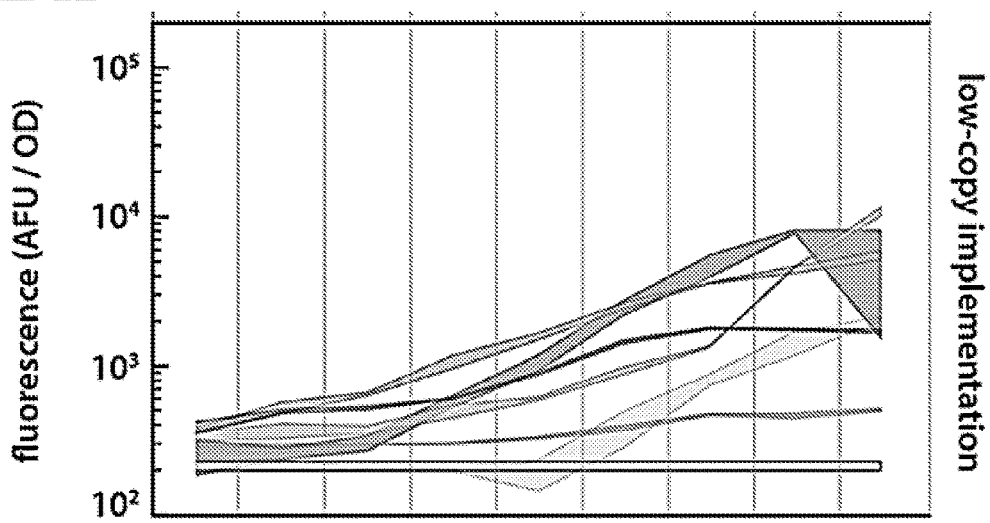

The relationship between inducer concentration and expression of the fluorescent reporter was evaluated for six inducible systems as shown in FIG. 1A and FIG. 1B. The resulting biosensor transfer functions encompass the complete range of sensor outputs, allowing determination of each biosensor's dynamic range. Evaluation of the transfer function also reveals the minimum and maximum expression level obtainable in each biosensor implementation. The calculated fold-induction (maximum fluorescence divided by uninduced fluorescence) of high-copy biosensors ranged from 63 to 210 as shown in Table 4. The fold-induction values indicated as being above a certain number are the result of the mean uninduced fluorescence residing within, or very near, the intensity of the cellular auto-fluorescence. A true number for fold-induction is undefined in this scenario, so a minimum fold-induction was determined using the bounds of the 95% confidence intervals. The greatest magnitude of induction among the high-copy biosensors was achieved with AraC, followed by CdaR and MphR as shown in FIG. 1A. For the low-copy biosensors, fold induction ranged from 3 to 78. The AcuR biosensor demonstrated the lowest uninduced accumulation of GFP, with no fluorescence above background in the absence of acrylate for both the high and low copy systems. This is in contrast to the TtgR biosensor, which showed higher uninduced accumulation of GFP in the low-copy configuration. The opposite effect was observed for the TetR biosensor, which demonstrated a lower uninduced accumulation of GFP, such that fluorescence was within that of the background in the low-copy configuration as shown in FIG. 1B.

The time required for induction was evaluated for each biosensor as shown in FIG. 2, FIG. 10 and FIG. 11. Reporter expression was monitored for eight hours with a wide range of inducer concentrations. All high-copy biosensors began producing fluorescence above background within 30 minutes, and achieved maximum levels of fluorescence within five hours under the highest induction conditions. Low-copy biosensors began producing measurable fluorescence within 50 minutes, but could require more than eight hours to achieve maximum fluorescence at the highest levels of induction. While the onset of expression began rapidly and without much variability between biosensors, the maximum fluorescence was sensor-dependent. For example, the CdaR biosensor achieved maximum fluorescence from moderate induction in nearly one hour, while the highest glucarate induction condition required six hours to reach maximal fluorescence. This is in contrast to the high-copy MphR biosensor, which approached maximal fluorescence around three hours regardless of the intensity of induction. The low copy variant of the MphR biosensor showed a similar trend, but required additional time to achieve maximum fluorescence as shown in FIG. 10. Variability in the kinetics of induction may be related to the intrinsic strength of the regulated promoter, sensor-DNA equilibrium, or the relationship between biosensor activity and growth-phase. Each repressor besides AcuR ceased to accumulate additional fluorescence at the onset of stationary phase. This is in contrast to the activators, which achieved maximal fluorescence well before stationary phase. Contrary to the behavior of the other repressors, strong induction of AcuR by acrylate is enabled by entry into stationary phase.

Complex synthetic circuits can be mathematically modeled to aid in component selection and system design. A model of gene activation is applied as described herein to relate promoter activity to inducer concentration. Promoter activity is defined as the time derivative of fluorescence corrected for cell growth. The time required for fluorophore maturation was considered and found to be less than two minutes (see Pedelacq, J. D., Cabantous, S., Tran, T., Terwilliger, T. C. and Waldo, G. S. (2006) Engineering and characterization of a superfolder green fluorescent protein. *Nature Biotechnology*, 24, 79-88). Likewise, degradation of GFP was ignored because the half-life in *E. coli* is greater than 24 hours (see Andersen, J. B., Sternberg, C., Poulsen, L. K., Bjorn, S. P., Givskov, M. and Molin, S. (1998) New unstable variants of green fluorescent protein for studies of transient gene expression in bacteria. *Applied and Environmental Microbiology*, 64, 2240-2246). Gene expression rates were fit to a Hill function adapted to account for both the maximum velocity of gene expression and the basal expression of the uninduced cells. Activators, AraC and CdaR, had Hill coefficients indicating low cooperatively. The repressors TetR, AcuR and TtgR all exhibited high cooperatively. The exception is the repressor MphR, which has a lower Hill coefficient. See Table 4. Examination of the activity-induction curves of the high-copy sensors reveals that the induction behavior of MphR is more similar to that of the activators AraC and CdaR, rather than the other repressors TetR, AcuR and TtgR. See FIG. 3. The same trend holds for the activity-induction curves of the low-copy sensors except that AcuR demonstrates less cooperatively in this implementation, potentially due to its dependence on growth phase for activation. See FIG. 12. Due to the toxicity of acrylate at 10 mM, this induction condition was omitted from the data used for modeling. Likewise, the highest concentrations of erythromycin were omitted from the low-copy MphR biosensor model as they showed substantial toxicity, likely due to lower expression of the erythromycin resistance gene. The maximum velocity of the high-copy sensors was always greater than the low-copy versions. However, the magnitude of the change was greater in the repressors than the activators. The activator-based sensors control their own expression and this feedback may provide some expression stability in the face of copy number variation. Basal promoter activity was less than 3% of the maximum promoter activity for each high-copy biosensor. Low-copy biosensors had higher and more variable basal promoter activity due to lower maximum activities, and in some cases, less effective transcriptional repression.

Individual cells were evaluated by flow cytometry to determine whether the ensemble induction dynamics were indicative of single cell behavior, or were instead an averaged result of stochastic, all-or-nothing responses in individual cells. See FIG. 4 and FIG. 13. This type of characterization is useful, as some inducible systems have been observed to produce bimodal or otherwise heterogeneous induction patterns due to positive feedback or inducer transport properties. Basal, low and high induction levels were measured after overnight induction. For each biosensor, it was shown that the majority of individual cells exhibit fluorescence in response to inducer concentration. In cases where a small group of cells do not fluoresce, the population represents less than 2% of the total cell population and may consist of dead cells, or cells containing dysfunctional plasmids. Nonetheless, the individual cell responses reflect the population-averaged behavior observed in ensemble measurements. High-copy AraC and CdaR biosensors both have high basal levels of reporter expression when evaluated in bulk. See FIG. 1A. These sensors demonstrated the widest uninduced fluorescence distributions when evaluated at the single cell level. See FIG. 4. The TetR biosensor has a broad fluorescence distribution when partially induced. When partially induced, both low copy MphR and high copy TtgR fluorescence distributions are compressed against the limit of detection. See FIG. 13. This could indicate that the left tail of the distribution is below the limit of detection, or that some cells are not activating in response to the inducer. As observed in the ensemble measurements, TtgR induction is weak. In the case of the low copy TtgR plasmid, the induced and uninduced populations almost entirely overlap when observed by flow cytometry. See FIG. 13.

Toxicity of the inducer chemicals was measured to help guide the choice of inducer concentration for biosensor applications. See FIG. 5. In applications where maximum protein production is the goal, toxicity will be less of a consideration. In contrast, sub-toxic induction is important for complex circuits that require the cell to maintain a healthy cell state. As expected, erythromycin was toxic to *E. coli* at concentrations as low as 50 µM. However, with expression of the erythromycin resistance gene (eryR), only slight toxicity was observed at erythromycin concentrations up to 1.4 mM. A similar growth defect was observed with 430 nM anhydrotetracycline (aTC). Both growth defects are likely due to the solvent, in this case ethanol. Naringenin showed significant toxicity at concentrations of 330 µM and above. This toxicity is likely due to the flavonoid itself, rather than the solvent dimethylsulfoxide (DMSO). Acrylate showed substantial toxicity at 5 mM and 10 mM. High concentrations of arabinose resulted in higher growth rates due to *E. coli*'s ability to use the sugar as a carbon source. Similar but more modest growth benefits were observed at the highest concentration of glucarate and at low levels of ethanol supplementation.

Example VIII

Sensor Orthogonality

The cross-reactivity of each biosensor was evaluated with a panel of inducing compounds: acrylate, arabinose, glucarate, erythromycin, aTC, naringenin, IPTG, rhamnose, cumate and the solvents, DMSO and ethanol. The inducing compounds not otherwise evaluated were included to provide forward compatibility for future biosensor implementations. No sensor was observed to respond to any of the evaluated compounds except for its cognate inducer. See FIG. 6. Cumate, glucarate and acrylate all feature a carboxylate, yet are discriminated by their respective sensors. TtgR is not activated by cumate although it binds many similar molecules, one of which is chloramphenicol. TtgR activation by chloramphenicol precludes engineered systems containing TtgR alongside a plasmid maintained by chloramphenicol acetyl transferase.

While the cross-reactivities of the biosensors were evaluated with a single sensor per cell, methods provided herein utilize multiple orthogonal sensors within a single cell. According to this aspect, several sensors were constructed and introduced into the same cell to allow stable maintenance and non-overlapping fluorescent readouts. The MphR biosensor was reconstructed such that erythromycin controlled the expression of mCherry in a vector backbone encoding the p15a replication origin and spectinomycin resistance. Similarly, the AcuR biosensor was reconstructed in a vector backbone encoding the colA origin and kanamycin resistance to facilitate acrylate-mediated expression of CFP. These plasmids were co-transformed with the pJKR-H-CdaR plasmid (encoding GFP) and stably maintained in DH5α cells. Overnight induction of this strain with every combination of glucarate, erythromycin and acrylate induction resulted in eight distinct cell states as measured by fluorescence in the three channels. See FIG. 7. High, but non-toxic, levels of inducer were chosen for each orthogonal induction channel.

Flow cytometry was used to evaluate individual cell behavior. Without induction, there is low fluorescence in all channels, as represented by the orange population in FIG. 7. Induction with only glucarate results in individual cells changing their cell state by producing GFP with no CFP or RFP expression (light blue population in FIG. 7). The trend continues with induction by erythromycin producing the dark blue cell population exhibiting high fluorescence in the red channel, but low fluorescence in the blue and green channels. Similarly, the dark green points represent acrylate-induced cells with high fluorescence in the blue channel. Induction by all three ligands results in the light green cell population demonstrating high fluorescence in all three channels.

In principle, 16 distinct cell states can be defined with four orthogonal inducible systems, and 32 distinct cell states can be defined with five inducible systems. In these cases, output channels may become limiting, as there may be limited distinct fluorescent proteins. If three levels of induction are considered (none, intermediate and high), rather than the binary case exemplified, the number of cell states increases from 8 to 27 for the system of three orthogonal biosensors, and from 16 to 81 for the theoretical system of four orthogonal biosensors.

Example IX

Sensors for Metabolic Flux Monitoring

The CdaR biosensor was used to monitor production of glucarate from myo-inositol. Glucarate can be produced from biomass as a renewable replacement for nylon and other plastics (see Werpy, T. a. P., G. (2004) In Energy, U. S. D. o. (ed.), however high titers are currently limited by the activity of myo-inositol oxygenase (MIOX) (see Moon, T. S., Yoon, S. H., Lanza, A. M., Roy-Mayhew, J. D. and Prather, K. L. (2009) Production of glucaric acid from a synthetic pathway in recombinant *Escherichia coli. Applied and environmental microbiology*, 75, 589-595, which converts myo-inositol into glucuronate. Glucuronate is in turn oxidized to glucarate by the fast-acting enzyme glucuronate dehydrogenase (Udh). By co-transforming plasmids containing the CdaR biosensor, a constitutively expressed Udh gene and a library of five constitutively expressed MIOX orthologs, enzymes producing higher glucarate titers in *E. coli* were identified. The four MIOX variants produced a 20-fold range in fluorescence after 16 hours (see FIG. 8). Mass spectrometry was used to determine actual glucarate titers in order to determine if biosensor readout was predictive of an enzyme's potential for glucarate production. Glucarate titers were well correlated with fluorescence (see FIG. 8), enabling the use of biosensors in high throughput discovery and optimization of enzymatic activity. *Mus musculus* MIOX ortholog produced the highest fluorescence and titer. A very similar glucarate titer and biosensor response was obtained from the *Flavobacterium johnsoniae* MIOX ortholog that shares only 45% identity with the *Mus musculus* variant.

Example X

TtgR as a Sensor for Phenol

Phenol is an important commodity chemical for which novel production routes would provide economic and environmental benefits. Some success has been shown in enzymatic conversion of benzene to phenol (see Farinas, E. T., Alcalde, M. and Arnold, F. (2004) Alkene epoxidation catalyzed by cytochrome P450 BM-3 139-3. *Tetrahedron*, 60, 525-528 and Karich, A., Kluge, M., Ullrich, R. and Hofrichter, M. (2013) Benzene oxygenation and oxidation by the peroxygenase of *Agrocybe aegerita*. AMB Express, 3, 5), however these enzymes function with low $k_{cat}$, and in some cases continue oxidizing phenol to catechol, an undesirable side product. Separate populations of the TtgR biosensor strain were incubated with 0.1% phenol, 0.1% catechol and up to 0.4% benzene. As shown in FIG. 9, only phenol activated the sensor, indicating a selective response of TtgR to phenol, but not byproducts of phenol production. Accordingly to this aspect, phenol production is coupled to expression of fluorescent proteins or antibiotic selection markers in individual cells using a TtgR sensor.

Example XI

Indirect Sensing of 3-Hydroxypropionate 3-hydroxypropionate (3-HP) is an important commercial reagent in the production, for example, of acrylate. According to one aspect, cells can be genetically modified to produce 3-HP, however, there is no known transcriptional sensor for 3-HP. According to methods described herein, cells are genetically modified to transform 3-HP into an effector molecule having a transcriptional sensor. FIG. 14 depicts a schematic showing one biological route to 3-HP from glucose and the enzymatic reactions used to convert 3-HP into an effector molecule having a transcription factor.

According to a first aspect, 3-HP is transformed into 2-methylcitrate in the presence of a 2-methylcitrate sensor. The resulting system is a 3-HP biosensor. The transcriptional regulator prpR from *E. coli* is used to control gene expression in proportion to the concentration of 2-methylcitrate inside the cell. This inducible system has been described previously with the aim of sensing propionate—a distinct chemical from 3HP (WO 2007005837 A3, http://www.ncbi.nlm.nih.gov/pubmed/16269719). The endogenous enzyme, 2-methylcitrate synthase (prpC), and the heterologous multifunctional enzyme propionyl-CoA synthase (pcs) from the carbon fixation pathway of *Chloroflexus aurantiacus* (see Mattozzi, M., Ziesack, M., Voges, M. J., Silver, P. A. and Way, J. C. (2013) Expression of the sub-pathways of the *Chloroflexus aurantiacus* 3-hydroxypropionate carbon fixation bicycle in *E. coli*: Toward horizontal transfer of autotrophic growth. *Metab Eng*, 16, 130-139 hereby incorporated by reference in its entirety) are used to produce 2-methylcitrate from 3-HP. Together the system of three genes (pcs, prpC, prpR) comprises the prpR-based 3HP biosensor (see FIG. 15A). The fluorescent response of the prpR-based biosensor to concentrations of 3HP up to 25 mM with and without the presence of pcs was evaluated (see FIG. 15B). The pcs is necessary for a fluorescent response to 3-HP. The response increases with increasing concentrations of 3-HP, indicating that the intracellular concentrations of 3HP and 2-methylcitrate are linked. As a result of this linkage, 3-HP concentration controls expression of green fluorescent protein (GFP). When induced with 12 mM 3-HP, the prpR-based 3-HP biosensor produces a fluorescent response 2.4-fold greater than uninduced fluorescence. The fluorescent response of the prpR-based biosensor to 3-HP induction is half-maximal at 5 hours and requires approximately 8 hours to reach 90% induction (see FIG. 15C). The proportion of 2-methylcitrate produced in this way is proportional to the amount of 3-HP inside the cell. The expression of the controlled gene is thus a measurement of intracellular 3-HP concentration.

According to a second aspect, 3-HP is transformed into acrylate in the presence of an acrylate biosensor. The transcriptional regulator acuR is used to regulate transcription of a target gene in proportion to the amount of acrylate present in the cell. Accordingly, the acrylate biosensor reports intracellular 3HP concentration. A truncated version of the multifunctional enzyme pcs is used to convert 3HP into acrylyl-CoA, which is subsequently hydrolyzed to acrylate by the acrylyl-CoA hydrolase (ach) from *Acinetobacter baylyi* (see Valle F., A., N. J., Noriega, C. (2013). In *Chloroflexus aurantiacus*, pcs catalyzes three subsequent reactions: 3HP to 3HP-CoA to acrylyl-CoA to propionyl-CoA (see Mattozzi, M., Ziesack, M., Voges, M. J., Silver, P. A. and Way, J. C. (2013) Expression of the sub-pathways of the *Chloroflexus aurantiacus* 3-hydroxypropionate carbon fixation bicycle in *E. coli*: Toward horizontal transfer of autotrophic growth. *Metab Eng*, 16, 130-139 hereby incorporated by reference in its entirety). All three reactions are useful for a prpR-based biosensor, but for the acuR-based biosensor, accumulation of acrylyl-CoA rather than propionyl-CoA is necessary. Separation of pcs into its functional domains has been shown to increase the rates of the individual reactions (see Alber, B. E. and Fuchs, G. (2002) Propionyl-coenzyme A synthase from *Chloroflexus aurantiacus*, a key enzyme of the 3-hydroxypropionate cycle for autotrophic $CO_2$ fixation. *The Journal of biological chemistry*, 277, 12137-12143). Accordingly, the domain responsible for conversion of acrylyl-CoA to propionyl-CoA was removed while preserving the activity of the other two domains. The truncated enzyme is referred to as $pcs^{\Delta 3}$, and its co-expression with ach and acuR constitute the acuR-based 3HP biosensor (see FIG. 16A). Increasing concentrations of 3HP in the media resulted in increasing levels of fluorescence when $pcs^{\Delta 3}$ and ach were present, but resulted in no biosensor activation in their absence (see FIG. 16B) indicating that 3-HP is being converted to acrylate and sensed by acuR. A 90-fold increase in fluorescence was obtained when the acuR-based biosensor was induced with 10 mM 3HP. The induction kinetics of 3HP and the authentic activator acrylate were compared by monitoring biosensor activation in real-time. 3HP-mediated induction only slightly lagged the time-course of acrylate induction (see FIG. 16C). Fluorescence remained at background levels for greater than 16 hours in the absence of $pcs^{\Delta 3}$ and ach (see FIG. 17).

Accordingly, the resulting system maintains acrylate at a level that is proportional to 3HP concentration and transcriptional output at a level proportional to acrylate concentration. Transcriptional readout is thus a measurement of intracellular 3HP concentration.

FIG. 18 shows the response of the prpR-based 3-HP biosensor to increasing concentrations of 3-HP. The green bars show the complete system is responsive to 3-HP while the gray bars show that the prpR sensor alone cannot detect 3-HP.

FIG. 19 shows the response of the acuR-based 3-HP biosensor to increasing concentrations of 3-HP. The blue bars show the complete system is responsive to increasing amounts of 3-HP while the gray bars show that the acuR sensor alone does not react to the presence of 3-HP.

Example XII

Real-Time Metabolite Observation Using prpR-Based 3-HP Biosensor to Induce Production of a Fluorescent Reporter 3-HP production was monitored in real time by using the prpR-based 3-HP biosensor. As shown in FIG. 20A, the 3-HP production pathway consists of the endogenous biosynthesis of malonyl-CoA and the bi-functional enzyme malonyl-CoA reductase (mcr) from the carbon fixation pathway of *Chloroflexus aurantiacus*. Mcr shunts malonyl-CoA away from fatty acid biosynthesis by catalyzing the conversion of malonyl-CoA, first into malonate semialdehyde, and then into 3HP at the expensive of two NADPH+. This route from glucose to 3HP has been published previously, achieving titers of 60 mg/L with expression of mcr alone (see Rathnasingh, C., Raj, S. M., Lee, Y., Catherine, C., Ashok, S. and Park, S. (2012) Production of 3-hydroxypropionic acid via malonyl-CoA pathway using recombinant *Escherichia coli* strains. *Journal of biotechnology*, 157, 633-640). Titers were increased to 180 mg/L with overexpression of the ACC complex and pntAB, increasing availability of malonyl-CoA and NADPH+, respectively. The amount of malonyl-CoA available for 3HP production was increased by use of the fatty acid inhibitor cerulenin rather than through genetic manipulations. Fatty acid biosynthesis is the primary sink for malonyl-CoA and operates at a much higher velocity than heterologously expressed mcr. Since cerulenin inhibits the activities of fabB and fabF, increasing its concentration results in lower fatty acid biosynthesis rates and a higher concentration of available malonyl-CoA. In each of the 3-HP implementations, the biosensor helper enzymes, pcs and pcs$^{\Delta 3}$/ach, were constitutively expressed while mcr was expressed conditionally with the addition of IPTG.

Co-expression of mcr and the prpR-based 3HP biosensor facilitates observation of 3HP production without the need for HPLC or mass spectrometry (see FIG. 20B). Cells containing both the biosensor and mcr showed higher fluorescence over time than cells containing just the biosensor. When mcr activity was increased by induction with IPTG, the mcr containing cells showed a higher rate of GFP accumulation, ultimately achieving higher levels of fluorescence. The cells without mcr were unaffected by IPTG induction. When the prpR-based biosensor was used for 3-HP observation, 3-HP was produced using rich LB media as the carbon source. Sensitivity of prpR to catabolite repression precluded the use of glucose as the starting material for 3-HP production. Even low levels of glucose result in the prpR transcriptional regulator becoming non-responsive to induction. The uninduced expression of GFP from the prpR biosensor is significant, likely due to basal levels of 2-methylcitrate in the cell. Nonetheless, end point fluorescence measurements revealed that cells with the capacity to produce 3HP (mcr+) are 20% more fluorescent than cells without mcr (see FIG. 20C). When induced, the mcr+ cells are 50% more fluorescent, approaching induction levels observed with 1.5 mM of exogenous 3-HP.

Example XIII

Real-Time Metabolite Observation Using acuR-Based 3-HP Biosensor to Induce Production of a Fluorescent Reporter 3-HP production was monitored in real time by using the acuR-based 3-HP biosensor as shown in FIG. 20D. The acuR biosensor is not affected by catabolite repression and can be used to observe 3-HP production from glucose. Mcr was co-expressed with the acuR-based biosensor and fluorescence was observed for twelve hours. Cells that were incubated with 50 mM glucose, but no IPTG or cerulenin, produced fluorescence indistinguishable from background levels. Cells incubated with glucose and IPTG showed a significant increase in fluorescence. The most dramatic increase in fluorescence was observed when both IPTG and cerulenin were used. Production of 3-HP with glucose, IPTG and cerulenin resulted in higher rates of GFP expression and end-point fluorescence values than either of the other two culture conditions. End-point measurements reveal an eight-fold increase in fluorescence for mcr+ cells versus mcr– cells when incubated with glucose, IPTG and cerulenin (see FIG. 20E). Incubation with glucose and IPTG results in a two-fold increase. Incubation with glucose alone results in only a 20% increase in fluorescence compared to cells lacking mcr.

Example XIV

Real-Time Glucarate Observation Using cdaR-Based Glucarate Biosensor to Induce Production of a Fluorescent Reporter Production of glucarate in a cell was observed in real time. A cell was genetically modified to include the glucarate biosensor cdaR regulating production of a fluorescent molecule with the glucarate biosynthesis pathway of IPTG inducible myo-inositol-1-phosphate synthase (Ino1, *Saccharomyces cerevisiae*), myo-inositol oxygenase (MIOX, *Mus musculus*) and uronate dehydrogenase (Udh, *Agrobacterium tumefaciens*) as shown in FIG. 21A. The glucarate biosensor produced a fluorescent response proportional to the amount of glucarate produced within the cell. In representative examples, identical production conditions (genetics, media composition) were maintained but the exogenously supplemented precursor molecules were varied. Compounds further along in the biosynthesis pathway (i.e. separated from glucarate by fewer reactions) resulted in a faster rate of glucarate formation. Addition of glucarate itself resulted in the fastest rate of GFP production and ultimately the highest amount fluorescence as shown in FIG. 21B. The fluorescent response to glucarate was observed in biosensor strains with and without the biosynthesis pathway. None of the other exogenously supplied molecules resulted in a fluorescent response in the biosensor strain lacking the glucarate biosynthesis pathway as shown in FIG. 21C. In the strain containing both the biosensor and the biosynthesis pathway, addition of glucuronate to the media resulted in a fluorescent response lagging glucarate by about 90 minutes, ultimately achieving an end-point fluorescence that was 80% that of glucarate. This is in contrast to the addition of myo-inositol, which resulted in a fluorescence response lagging that of glucuronate by 60 minutes. The end-point fluorescence achieved by the addition of myo-inositol is just 20% that of glucuronate addition. Media supplemented with 50 mM glucose resulted in no fluorescent response within the duration of the experiment as shown in FIG. 21B.

The fluorescent output of the glucarate biosensor reflects the properties of the glucarate biosynthesis pathway. The conversion of glucuronate to glucarate is known to be the fastest heterologous reaction in the biosynthesis of glucarate. Correspondingly, robust biosensor activation is seen when glucuronate is the starting material. The fluorescent response to myo-inositol addition is slow and may be due to using *M. musculus* MIOX in the catalysis of myo-inositol to glucuronate in *E. coli*. The lack of biosensor response to additional glucose may be because glucarate biosynthesis is competing with glycolysis for glucose-6-phosphate. Substantial Ino1 activity may be required to create meaningful quantities of myo-inositol. Low myo-inositol production can result from weak MIOX activity, ultimately yielding low glucarate titers and biosensor mediated fluorescence. Accordingly, methods are provided for tuning the endogenous metabolism to balance glycolysis with glucarate production, while screening for fluorescence resulting from glucose supplementation, to identify strains that produce high glucarate titers. Similar method are provided for identifying a useful and effective variant of MIOX from a library of targeted or untargeted mutations.

While the kinetics of the fluorescence response reveals the relative rates of product formation, end-point fluorescence is a good proxy for product titer. The fluorescence observed eight hours after addition of the precursor molecules was measured and compared to the glucarate titers achieved under similar conditions. Glucarate production was observed in every condition tested when the cells contained the biosynthesis pathway, but no production was observed without the pathway. Glucarate formation was observed in rich LB media even without additional substrate added. Addition of 5 mM glucose did not result in a significant increase in glucarate titer within eight hours, consistent with the observed lack of a fluorescent response. However, addition of myo-inositol resulted in an elevated glucarate titer as reflected in the fluorescent response. Addition of glucuronate resulted in glucarate production at a 97% yield (background production of glucarate from LB was subtracted). This yield reflects the high fluorescence achieved by glucarate addition. Plotting titer as a function of fluorescence reaffirms that fluorescence is a good predictor of titer across the four culture conditions evaluated ($R^2=0.96$) as indicated in FIG. 22.

Example XV

Real-Time Muconate Observation Using benM-Based Muconate Biosensor to Induce Production of a Fluorescent Reporter Production of muconate in a cell was observed in real time. A cell was genetically modified to include the muconate biosensor benM regulating production of a fluorescent molecule, and a LysR-type transcriptional regulator derived from *Acinetobacter baylyi* (see Craven, S. H., Ezezika, O. C., Haddad, S., Hall, R. A., Momany, C. and Neidle, E. L. (2009) Inducer responses of BenM, a LysR-type transcriptional regulator from *Acinetobacter baylyi* ADP1. *Mol Microbiol*, 72, 881-894 hereby incorporated by reference in its entirety). This setup is analogous to the previously described muconate artificial selection in which benM controls expression of an antibiotic resistance gene (see Raman, S., Rogers, J. K., Taylor, N. D. and Church, G. M. (2014) Evolution-guided optimization of biosynthetic pathways. *Proceedings of the National Academy of Sciences of the United States of America*, 111, 17803-17808 hereby incorporated by reference in its entirety. In order to achieve various muconate production rates for real-time observation, muconate was produced from a range of precursor molecules by implementing the biosynthetic pathway developed by Draths and Frost (see Niu, W., Draths, K. M. and Frost, J. W. (2002) Benzene-free synthesis of adipic acid. *Biotechnology progress*, 18, 201-211 and Draths, K. M. and Frost, J. W. (1994) Environmentally Compatible Synthesis of Adipic Acid from D-Glucose. *Journal of the American Chemical Society*, 116, 399-400 each of which are hereby incorporated by reference in its entirety.) This pathway uses three heterologous enzymes to convert 3-dehydroshikimate (DHS), an intermediate of aromatic amino acid biosynthesis, to cis,cis-muconate as shown in FIG. 23A. The branch-point from endogenous metabolism is catalyzed by DHS dehydratase (*Acinetobacter baylyi*, quiC) resulting in protocatechuate, which in turn is decarboxylated to catechol by protocatechuate decarboxylase (*Klebsiella pneumonia*, aroY) before oxygenation to muconate by catechol 1,2-dioxygenase (*Acinetobacter baylyi*, catA). A rapid fluorescence response was observed for the pathway intermediates DHS, protocatechuate and catechol, while a slow response was observed when muconate production started from glucose as shown in FIG. 23B. No fluorescent response to any of the intermediates was observed when the muconate biosynthesis pathway was absent. The observation that DHS produces a response as fast as the other pathway intermediates suggests that competition with aromatic amino acid biosynthesis is not limiting the rate of muconate production under these conditions. In contrast, the slow rate of GFP expression resulting from the addition of glucose indicates that achieving a sufficient endogenous DHS supply may be limiting in the genetic background used. This is consistent with the negative feedback that exists at both the transcriptional and allosteric levels in aromatic amino acid biosynthesis. The negative feedback is designed to throttle the production of DHAP (the precursor to DHS and consequently muconate) in the presence of aromatic amino acids. Strains optimized for muconate biosynthesis overexpress a feedback resistant mutant of aroF that is defective in product inhibition. Other genetic modifications aimed at increasing the DHS pool have included knockout of aroE and overexpression of aroB and tktA (see Niu, W., Draths, K. M. and Frost, J. W. (2002) Benzene-free synthesis of adipic acid. *Biotechnology progress*, 18, 201-211 hereby incorporated by reference in its entirety.

Examining end-point fluorescence indicates that the final fluorescence achieved is consistent with the muconate titers measured in the supernatant at that time-point as shown in FIG. 23C. While the end-point fluorescence of the late intermediates is similar, it is dramatically lower for glucose. This is reflected in the titers, as muconate production from glucose was lower than the limit of detection at this early time-point. The biosensor is more sensitive than the traditional methods of quantification. This may be attributed to intracellular versus extracellular sensing; unless muconate is actively transported out of the cell, intracellular concentrations would be expected to rise before supernatant concentrations. Using this intermediate biosensor with the muconate biosensor to control GFP and RFP provides method of screening which minimize the concentration of potentially toxic pathway intermediates and maximize end-product formation.

Example XVI

Methods Used for Examples XI to XVI

The following methods and materials were used for Examples XI to XVI.
Chemicals and Reagents All reagents were obtained from Sigma unless otherwise noted. Antibiotics and IPTG were obtained from Gold Biotechnology. PCR mix was purchased from Kapa Biosystems. 3-hydroxypropionate was purchased from Toronto Research Chemicals. Cerulenin was purchased from Cayman Chemical and dissolved in ethanol. Acrylic acid was stored at room temperature with 200 ppm MEHQ as an inhibitor and diluted immediately prior to use. All cell culture additives were dissolved in deionized water to achieve appropriate working concentrations.

Strains and Plasmids

Plasmids were constructed using Gibson isothermal assembly methods (see Gibson, D. G., Young, L., Chuang, R. Y., Venter, J. C., Hutchison, C. A., 3rd and Smith, H. O. (2009) Enzymatic assembly of DNA molecules up to several hundred kilobases. *Nat Methods,* 6, 343-345 hereby incorporated by reference in its entirety) and cloned into DH5α electrocompetent cells purchased from New England Biolabs. Biosynthesis of product molecules was carried out in either BL21 (DE3) or DH5α. The prpR-based 3HP biosensor was implemented as a two-plasmid system. The first plasmid is pPro24-GFP (Addgene plasmid #18880), which expresses GFPuv under the control of the methyl-citrate responsive transcription factor, prpR, on a pBR322 origin of replication providing β-lactam resistance. The second plasmid (pJKR-PCS) was constructed such that the enzyme propionyl-CoA synthase was under the control of the constitutive promoter proD on a ColA origin of replication providing kanamycin resistance. The acuR-based 3-HP biosensor is composed of two plasmids. The first is the previously characterized high-copy acrylate biosensor pJKR-H-acuR (Addgene plasmid #62567), which expresses sfGFP under the control of the acrylate responsive transcription factor, acuR, on a pUC origin of replication providing β-lactam resistance. The second is derived from pJKR-PCS such that PCS is truncated between amino acids 1400 and 1401. The enzyme acrylyl-CoA hydrolase from *Acinetobacter baylyi* was subsequently cloned into the plasmid under the control of the P2 constitutive promoter (see Mutalik, V. K., Guimaraes, J. C., Cambray, G., Lam, C., Christoffersen, M. J., Mai, Q. A., Tran, A. B., Paull, M., Keasling, J. D., Arkin, A. P. et al. (2013) Precise and reliable gene expression via standard transcription and translation initiation elements. *Nat Methods,* 10, 354-360 hereby incorporated by reference in its entirety). The resulting plasmid is designated pJKR-PCSfrag-ACH. The 3-HP biosynthesis plasmid, designated pJKR-MCR, was constructed such that malonyl-CoA reductase from *Chloroflexus aurantiacus* was expressed by the pLlacO promoter (see Lutz, R. and Bujard, H. (1997) Independent and tight regulation of transcriptional units in *Escherichia coli* via the LacR/O, the TetR/O and AraC/I1-I2 regulatory elements. *Nucleic acids research,* 25, 1203-1210) under the control of LacI on a p15a origin of replication with spectinomycin resistance. The glucarate biosensor is the previously characterized plasmid pJKR-H-cdaR (Addgene plasmid #62557), which expresses sfGFP under the control of the glucarate responsive transcription factor, cdaR, on a pUC origin of replication providing β-lactam resistance. The glucarate biosynthesis pathway was implemented on a single plasmid, pJKR-GA-EXP, which expresses the genes MIOX, Ino1 and Udh co-cistronically from an IPTG-regulated T7 promoter on a p15a origin of replication providing kanamycin resistance. MIOX from *Mus musculus* and Ino1 from *Saccharomyces cerevisiae* were synthesized with codons optimized for *E. coli* expression. Udh was obtained from *Agrobacterium tumefaciens* genomic DNA (ATCC #33970D-5). The muconate biosensor was constructed with sfGFP under the control of the muconate-responsive transcription factor benM (*Acinetobacter baylyi*) on a pUC origin of replication providing spectinomycin resistance. BenM was constitutively expressed with the proB promoter (see Davis, J. H., Rubin, A. J. and Sauer, R. T. (2011) Design, construction and characterization of a set of insulated bacterial promoters. *Nucleic acids research,* 39, 1131-1141 hereby incorporated by reference in its entirety.) To provide an option for expression normalization, the RFP mKate2 was constitutively expressed from the P11(32) promoter (see Mutalik, V. K., Guimaraes, J. C., Cambray, G., Lam, C., Christoffersen, M. J., Mai, Q. A., Tran, A. B., Paull, M., Keasling, J. D., Arkin, A. P. et al. (2013) Precise and reliable gene expression via standard transcription and translation initiation elements. *Nat Methods,* 10, 354-360 hereby incorporated by reference in its entirety). The resulting plasmid is designated pJKR-H-benM. The muconate biosynthesis pathway was constructed as a single plasmid with codon optimized variants of the biosynthesis genes expressed co-cistronically from an IPTG inducible T7 promoter on a p15a origin of replication providing β-lactam resistance.

3-Hydroxypropionate Biosensor Characterization

DH5α cells doubly transformed with plasmids pPro24-GFP and pJKR-PCS, or plasmids pJKR-H-acuR and pJKR-PCSfrag-ACH, were exposed to increasing concentrations of 3-HP and monitored for GFP expression. Cells were grown overnight to saturation before being diluted 1:100 into fresh LB media and incubated at 200 RPM and 37° C. After four hours, 150 μl of the log-phase cells were transferred to 96-well plates and 3HP was added to the appropriate final concentration. Each inoculation and induction was performed in triplicate. Strains lacking the biosensor helper plasmids were included to reveal that the biosensor activation was indeed dependent on the presence of the helper plasmids. In the case of the end-point measurements, fluorescence was measured 16 hours after 3-HP addition with a Biotek HT plate reader (excitation 485/20, emission 528/20). Time course data was collected over a 16 hour period on the same plate reader at 37° C. with fast shaking and 10 minute measurement intervals. Fluorescence was normalized by optical density. Fold induction was determined by dividing the fluorescence obtained at the current induction level by the fluorescence obtained without induction. Error bars represent the 95% confidence interval derived from the standard error of the mean.

3-Hydroxypropionate Production and Monitoring

DH5α cells containing the plasmids for the prpR- and acuR-based 3-HP biosensors were transformed with the plasmid pJKR-MCR. These production strains were grown up overnight and back-diluted 1:100 into fresh LB media and incubated at 200 RPM and 37° C. After four hours, 150 μl of the log-phase cells were transferred to 96-well plates and exposed to 3-HP production conditions. The prpR-based biosensor production strain was incubated with and without 1 mM IPTG and 20 μg/ml cerulenin in LB. The acuR-based biosensor production strain was incubated with 50 mM glucose and different combinations of 1 mM IPTG and 20 μg/ml cerulenin. Growth-normalized fluorescence was observed in the Biotek HT plate reader as described above. End-point measurements were taken after 12 hours. 3-HP production titers were determined by liquid-chromatography and mass spectrometry (LC/MS). The strain used for titer measurements only contained the production plasmid pJKR-MCR. Overnight cultures were inoculated 1:100 into 1 mL of LB supplemented with 1 mM IPTG, 20 μg/ml cerulenin and 50 mM glucose in 96-well blocks. Production took place at 900 RPM and 37° C. for 16 hours before supernatants were isolated and filtered at 0.2 μm for LC/MS. All production runs were setup in triplicate. Error bars represent the 95% confidence interval derived from the standard error of the mean.

Glucarate Production and Monitoring

Glucarate production monitoring was carried out in BL21 cells doubly transformed with pJKR-H-cdaR and pJKR-GA-EXP. BL21 transformed with pJKR-H-cdaR alone was used as a control. Overnight cultures back-diluted 1:100 into Davis media supplemented with 5 g/L glucose. After four hours incubating at 200 RPM and 37° C., 150 µl of the log-phase cells were transferred to 96-well plates and exposed to 1 mM IPTG with the pathway intermediates described. Normalized fluorescence was observed for eight hours after addition of the pathway intermediates. End-point measurements were taken after eight hours. Glucarate production for titer measurement was carried out in BL21 transformed with pJKR-GA-EXP. An overnight culture was inoculated 1:100 into 1 mL of LB supplemented with 1 mM IPTG and the specified concentration of pathway intermediate. Production took place in 96-well blocks at 900 RPM and 37° C. for eight hours before supernatants were isolated and 0.2 µm filtered for LC/MS. All production runs were setup in triplicate. Error bars represent the 95% confidence interval derived from the standard error of the mean.

Muconate Production and Monitoring

Muconate production monitoring was carried out in BL21 cells doubly transformed with pJKR-H-benM and the muconate production plasmid. Overnight cultures were grown overnight before being diluted 1:100 into LB and incubated at 200 RPM and 37° C. After four hours, 150 µl of the log-phase cells were transferred to 96-well plates and monitored in the plate reader. After one hour, the specified concentration of pathway intermediate was added in triplicate and fluorescence monitoring was resumed. End-point measurements were made five hours after the addition of intermediates. Strains transformed with the muconate production plasmid alone were used to determine product titers. An overnight culture was inoculated 1:100 into 1 mL of LB supplemented with the specified concentration of pathway intermediate. Production took place in 96-well blocks at 900 RPM and 37° C. for five hours. The quantity of muconate in the supernatant was determined by HPLC. All production runs were setup in triplicate. Error bars represent the 95% confidence interval derived from the standard error of the mean.

TABLE 2

Sequence of regulator proteins and cognate promoter/operators.

| Regulator | Promoter/Operator Sequence | Regulator Sequence |
|---|---|---|
| acuR | GCTTCACAACCGCACTTGATTTAATAGACCATACCGTCTATTATTTCTGG (SEQ ID NO: 3) | ATGCCGCTGACCGACACCCCGCCGTCTGTTCCGCAGAAACCGCGTCGTGGTCGTCCGCGTGGTGCTCCGGACGCTTCTCTGGCTCACCAGTCTCTGATCCGTGCTGGTCTGGAACACCTGACCGAAAAAGGTTACTCTTCTGTTGGTGTTGACGAAATCCTGAAAGCTGCTCGTGTTCCGAAAGGTTCTTTCTACCACTACTTCCGTAACAAAGCTGACTTCGGTCTGGCTCTGATCGAAGCTTACGACACCTACTTCGCTCGTCTCCTCGACCAGGCGTTCCTGGACGGTTCGCTGGCTCCGCTGGCTCGTCTGCGTCTGTTCACCCGTATGGCTGAAGAAGGTATGGCTCGTCACGGTTTCCGTCGTGGTTGCCTGGTTGGTAACCTGGGTCAGGAAATGGGTGCTCTGCCGGACGACTTCCGTGCTGCTCTGATCGGTGTTCTGGAAACCTGGCAGCGTCGTACCGCTCAGCTGTTCCGTGAAGCTCAGGCTTGCGGTGAACTGTCTGCTGACCACGACCCGGACGCTCTGGCTGAAGCTTTCTGGATCGGTTGGGAAGGTGCTATCCTGCGTGCTAAACTGGAACTGCGTCCGGACCCGCTGCACTCTTTCACCCGTACCTTCGGTCGTCACTTCGTTACCCGTACCCAGGAATAA (SEQ ID NO: 9) |
| araC | AGAAACCAATTGTCCATATTGCATCAGACATTGCCGTCACTGCGTCTTTTACTGGCTCTTCTCGCTAACCCCAACCGGTAACCCGCTTATTAAAAGCATTCTGTAACAAAGCGGGACCAAAGCCATGACAAAACGCGTAACAAAGTGTCTATAATCACGGCAGAAAAGTCCACATTGATTATTTGCACGGCGTCACACTTTGCTATGCCATAGCATTTTTATCCATAAGATTAGCGGATCCTACCTGACGCTTTTTATCGCAACTCTCTACTGTTTCTCCATACCCGCTTTCATATCTTTCACTTTTTTTGGGCTAAC (SEQ ID NO: 4) | ATGGCTGAAGCGCAAAATGATCCCCTGCTGCCGGGATACTCGTTTAACGCCCATCTGGTGGCGGGTTTAACGCCGATTGAGGCCAACGGTTATCTCGATTTTTTTATCGACCGACCGCTGGGAATGAAAGGTTATATTCTCAATCTCACCATTCGCGGTCAGGGGGTGGTGAAAAATCAGGGACGAGAATTTGTCTGCCGACCGGGTGATATTTTGCTGTTCCCGCCAGGAGAGATTCATCACTACGGTCGTCATCCGGAGGCTCGCGAATGGTATCACCAGTGGGTTTACTTTCGTCCGCGCGCCTACTGGCATGAATGGCTTAACTGGCCGTCAATATTTGCCAATACGGGTTTCTTTCGCCCGGATGAAGCGCACCAGCCGCATTTCAGCGACCTGTTTGGGCAAATCATTAACGCCGGGCAAGGGGAAGGGCGCTATTCGGAGCTGCTGGCGATAAATCTGCTTGAGCAATTGTTACTGCGGCGCATGGAAGCGATTAACGAGTCGCTCCATCCACCGATGGATAATCGGGTACGCGAGGCTTGTCAGTACATCAGCGATCACCTGGCAGACAGCAATTTTGATATCGCCAGCGTCGCACAGCATGTTTGCTTGTCGCCGTCGCGTCTGTCACATCTTTTCCGCCAGCAGTTAGGGATTAGCGTCTTAAGCTGGCGCGAGGACCAACGCATTAGTCAGGCGAAGCTGCTTTTGAGCACTACCCGGATGCCTATCGCCACCGTCGGTCGCAATGTTGGTTTTGACGATCAACTCTATTTCTCGCGAGTATTTAAAAAATGCACCGGGGCCAGCCCGAGCGAGTTTCGTGCCGGTTGTGAAGAAAAAGTGAATGATGTAGCCGTCAAGTTGTCAtaa (SEQ ID NO: 10) |
| cdaR | ATGCTGTTGATTGACGCCAGTGAGAACCCGGAACCGGAAACGGAATCAAATCCGTGGGTCGAACAGTGGGGCACGCTGTTGTCCTGATATGTTCAGCGAGCGGTAAATGTCGTTTTAGCGGTGCTGAATCGAATCTTTTCAGGCAAATGCCAGTAAAAACTGCTTCATAG | ATGGCTGGCTGGCATCTTGATACCAAAATGGCGCAGGATATCGTGGCACGTACCATGCGCATCATCGATACCAATATCAACGTAATGGATGCCCGTGGGCGAATTATCGGCAGCGGCGATCGTGAGCGTATTGGTGAATTGCACGAAGGTGCATTGCTGGTACTTTCACAGGGACGAGTCGTCGATATCGATGACGCGGTAGCACGTCATCTGCACGGTGTGCTGGCAGGGGATTAATCTACCGTTACGGCTGGAAGGTGAAATTGTCGGCGTAATTGGCCTGACAGGTGAACCAGAGAATCTGCTAAATATGGCGAACTGGTCTGCATGACGGCTGAAATGATGCTGGAACAGTCGCGGTTGATGCACTTGTTGGCGCAGGATAGCCGTTTGCGGGAAGAACTGGTGATGAACCTGATTCAGGCAGAGGAGAATACTCCCGCACTTACTGAATGGGCGCAACGGCTGGGGATCGATCTCAATCAACCGCGAGTGGTGGCTATTGTTGAGGTCGACAGCGGTCAGCTTGGCGTGGACAGC |

TABLE 2-continued

Sequence of regulator proteins and cognate promoter/operators.

| Regulator | Promoter/ Operator Sequence | Regulator Sequence |
|---|---|---|
| | CGCGGATTTTTACTGGC GTTTGCCTGGAGTCAAG CGATCCATTTCATACTC TTCTTTATTTCTTCGTT TTAACCCTTCCTTTCTT GTTCTTGTTTTCATTTC CGTGAAGTGGATTCCAC CGTCCAGGGCTAATGCC AAAATCGGGCCTCATTG AACGCATTAATGTTGTG TTGTTGCACGGTGAGCC GCTATGGCGCGCTTTTT ATACTGCTATTGCCAGA TATAAACACGCGCCGTA TTCGGCGAACGACCTAT AAAAACGGCAAAAAACA CCCTACGTCACCTCTGA TTTCCTGGCGATGTCGC AGTCCAGAGTGAGCGTG GCTAACGCGAATTTTCA GGAGTGCAACA (SEQ ID NO: 5) | GCAATGGCGGAGTTACAACAACTGCAAAACGCGCTGACTACGCCCGAGCGTAAT AATCTGGTGGCGATTGTCTCGCTAACCGAAATGGTGGTGTTGAAACCGGCGTTG AACTCTTTTGGGCGCTGGGATGCAGAAGATCATCGTAAGCGAGTTGAACAACTG ATTACCCGCATGAAAGAGTACGGCCAGCTGCGTTTTCGCGTTTCACTGGGCAAC TATTTTACCGGTCCTGGCAGTATTGCCCGATCCTATCGTACGGCGAAAACGACG ATGGTGGTGGGTAAACAGCGGATGCCAGAAAGTCGCTGCTATTTTTATCAGGAT CTGATGTTACCTGTGTTACTCGACAGTTTGCGTGGCGACTGGCAGGCCAACGAA CTGGCGCGACCGCTGGCGCGGCTGAAAACGATGGACAATAACGGCTTGCTGCGA CGAACGCTGGCGGCGTGGTTTCGCCACAATGTGCAACCGCTGGCAACGTCAAAG GCGTTGTTTATTCATCGTAATACCCTGGAGTATCGGCTTAATCGTATATCGGAA CTGACCGGGCTTGATTTGGGCAATTTTGATGACAGGTTGCTGCTGTATGTGGCG TTACAACTGGATGAAGAGCGGtag (SEQ ID NO: 11) |
| mphR | GGATTGAATATAACCGA CGTGACTGTTACATTTA GGTGGCTAAACCCGTCA A (SEQ ID NO: 6) | ATGCCGCGTCCGAAACTGAAATCTGACGACGAAGTTCTGGAAGCGGCGACCGTT GTTCTGAAACGTTGCGGTCCGATCGAATTCACCCTGTCTGGTGTTGCGAAAGAA GTTGGTCTGTCTCGTGCGGCGCTGATCCAGCGTTTCACCAACCGTGACACCCTG CTGGTTCGTATGATGGAACGTGGTGTTGAACAGGTTCGTCACTACCTGAACGCG ATCCCGATCGGTGCGGGTCCGCAGGGTCTGTGGGAATTCCTGCAGGTTCTGGTT CGTTCTATGAACACCCGTAACGACTTCTCTGTTAACTACCTGATCTCTTGGTAC GAACTGCAGGTTCGGAACTGCGTACCCTGGCGATCGAGCGTAACCGTGCGGTT GTTGAAGGTATCCGTAAACGTCTGCCGCCGGGTGCGCCGGCGGCGGCCGGAACT GCTGCTGCACTCTGTTATCGCGGGTGCGACCATGCAGTGGGCGGTTGACCCGGA CGGTGAACTGGCGGACCACGTTCTGGCGCAGATCGCGGCGATCCTGTGCCTGAT GTTCCCGGAACACGACGACTTCCAGCTGCTGCAGGCGCACGCGTAA (SEQ ID NO: 12) |
| tetR | TCGAGTCCCTATCAGTG ATAGAGATTGACATCCC TATCAGTGATAGAGATA CTGAGCACATCAGCAGG ACGCACTGACCGAATTC ATTAAA (SEQ ID NO: 7) | ATGTCTCGTTTAGATAAAAGTAAAGTGATTAACAGCGCATTAGAGCTGCTTAAT GAGGTCGGAATCGAAGGTTTAACAACCCGTAAACTCGCCCAGAAGCTAGGTGTA GAGCAGCCTACATTGTATTGGCATGTAAAAAATAAGCGGGCTTTGCTCGACGCC TTAGCCATTGAGATGTTAGATAGGCACCATACTCACTTTTGCCCTTTAGAAGGG GAAAGCTGGCAAGATTTTTTACGTAATAACGCTAAAAGTTTTAGATGTGCTTTA CTAAGTCATCGCGATGGAGCAAAAGTACATTTAGGTACACGGCCTACAGAAAAA CAGTATGAAACTCTCGAAAATCAATTAGCCTTTTTTATGCCAACAAGGTTTTTCA CTAGAGAATGCATTATATGCACTCAGCGCAGTGGGGCATTTTACTTTAGGTTGC GTATTGGAAGATCAAGAGCATCAAGTCGCTAAAGAAGAAAGGGAAACACCTACT ACTGATAGTATGCCGCCATTATTACGACAAGCTATCGAATTATTTGATCACCAA GGTGCAGAGCCAGCCTTCTTATTCGGCCTTGAATTGATCATATGCGGATTAGAA AAACAACTTAAATGTGAAAGTGGGTCTTAA (SEQ ID NO: 13) |
| ttgR | CACCCAGCAGTATTTAC AAACAACCATGAATGTA AGTATATTCCTTAGCAA (SEQ ID NO: 8) | ATGGTGCGTCGCACCAAAGAAGAAGCACAGGAAACGCGTGCGCAGATTATCGAA GCGGCCGAACGCGCGTTTTATAAACGTGGTGTGGCACGTACCACGCTGGCAGAT ATTGCAGAACTGGCAGGTGTTACCCGCGGTCAATCTACTGGCATTTCAACAAT AAAGCCGAACTGGTTCAGGCACTGCTGGATTCTCTGCACGAAACGCATGATCAC CTGGCCCGTGCAAGCGAATCTGAAGATGAACTGGACCCGCTGGGCTGCATGCGC AAACTGCTGCTGCAGGTGTTTAACGAACTGGTTCTGGATGCACGTACCCGTCGC ATTAATGAAATCCTGCATCACAAATGCGAATTTACGGATGATATGTGTGAAATT CGTCAGCAGCGCCAGAGCGCCGTGCTGGATTGTCATAAAGGTATCACCCTGGCA CTGGCAAACGCAGTTCGTCGCGGTCAGCTGCCGGGTGAACTGGATGCTGGAACGC GCAGCGGTTGCGATGTTTGCCTATGTGGATGGCCTGATTGGTCGTTGGCTGCTG CTGCCGGATAGTGTTGATCTGCTGGGCGATGTGAAAAATGGGTTGATACCGGT CTGGATATGCTGCGTCTGAGCCCGGCGCTGCGCAAATAA (SEQ ID NO: 14) |

TABLE 3

Sequence of MIOX orthologs

| MIOX Variant | Sequence |
| --- | --- |
| Candida albicans | ATGGTAAACAAGGTCGGTAAATCTACTCTCGATAAGAGCACAAACCTAGATAAATCCAAAGGGAATATATT<br>AGAGAAACTAGATGATGATATACTTCATGTCAATAGAATTCGAGGCTCTTTAACTAACAAAACTCCAATCA<br>CCAAAACCCATTCGATAGATGATGAGCTTAAACTAGAAGAACAATCAGAAACTGCCGCCGATGAAATTGG<br>CAAATAGCATCGGAATATTATAAAAACATAGCACGAAGGCTTTCCGCCAATATGAATTAGCTTGTGATAG<br>AGTCAAACAGTTTTATGAAGAACAACATGAAAAACAAACCGTGGCTATAATATTCAAGCAAGAATTAATT<br>TCAAAACTAAAACAAGAGCAAGAATGACAGTTTGGGAAGGACTAGAGAAATTAAACAAATTGTTAGATGAT<br>TCTGATCCCGACACCGAATTGTCACAAATAGATCATGCATTACAGACGGCAGAAGCTATACGGCGAGATGG<br>GAAACCACGATGGTTTCAATTAGTTGGGTTGATTCATGATTTAGGGAAATTACTATATTTTTTTGATTCTC<br>GTGGTCAATGGGATGTAGTGGGTGATACTTTCCCTGTTGGTTGTAAATTCCTGAAACGGATTATTTTCCCT<br>GATAGTTTTAAAAATAATCCAGATTTCCTAAATCCATTGTATAATACCAAATATGGCATATATTCAAAACA<br>TTGTGGATTAGATAAAGTCATGTTGAGTTGGGGTCATGATGAGTATATGTATCATGTTGCGAAAAAGAATT<br>CGACATTACCACCGGAAGCATTGGCAATGATAAGGTATCATTCATTTTATCCTTGGCATCAAGAATTGGCA<br>TATAGTTATTTAATGGATGAGCATGATAAAGAGATGTTGAAAGCAGTCAAAGCTTTCAATTCCTATGATTT<br>ATATTCCAAGATAGATCAACAGTATGATGTTGAAGAGTTGAAACCATATTACCTAGAGTTGATTGATGAGT<br>TTTTCCCAAATAAAGTAATTGATTTTTAA<br>(SEQ ID NO: 15) |
| Francisella sp. TX077308 | ATGAGTCAGACCGTGGAAAACACGTTTGGCGAATTTCGTAACTACACCGATAGCAAATTCCAGGATCGTGT<br>GGAACGCACGTACAAAGATATGCACATTAACCAGAATCTGGAATACGTTACCCAGATGAAAGATAAATACT<br>TCAAACTGGATCTGGGTAAAATGGATGTGTACGAAGTTTTCAAACTGCTGGAAAACGTTCATGATGAAAGC<br>GATCCGGATAATGATCTGCCGCAGATCGAACACGCATATCAGACCGCGGAAGCCTGCCAGAACAAATTCCT<br>GAAATCTGATACGGAACTGCGCGAAAATGCGCTGATTCGTAGTATCTTTCGCGATCATGAATGGCAGAGCA<br>TTCCGAAAATCTGGCAGGATTTCTATACCAAAAAACAGAGTCTGGGCAATCTGTACAGCCATATTAAAGAT<br>TGGTCTTGGTTTCCGCTGGTTGGCTTCGTTCACGATCTGGGTAAAATCATGACCCTGCCGGAATATGGTCA<br>GCTGCCGCAGTGGAGCACCGTGGGTGATACGTACCCGATTGCCTGCCCGTTTGCAAGCGCGAACGTGTTTT<br>CTCACCGTGAATTTGTTAAAGATTCTAAAGATTACAACAATTACAATACCGAAAGTGAAACGCATTATGGC<br>AAATACGAGAAAAAATGTGGTTTCGATAACGTGGATATGAGCTTCGGTCACGATAATACATCTACAAAGT<br>TTTCGAACAGGGCAGCGATATCCCGTATGAAGGTCTGTACCTGCTGCGCTATCATTCTTTCTACCCGTGGC<br>ACACCCCGCAGACGGGCGGTCATGCGTATCAGGAACTGGCCAACGAAAAAGATTGGCTGCTGCTGCCGCTG<br>CTGAAAGCCTTTCAGAAAGCGGATCTGTATTCTAAACTGCCGGAACTGCCGCCGAAAGAAGTGCTGGAGAA<br>AAAATACAAAAGTCTGCTGGATAAATGGGTTCCGAACAAGAAAATTAACTGGTAA<br>(SEQ ID NO: 16) |
| Flavobacterium johnsoniae | ATGAAAAAGCATATAGACACAGACAATCCGTTGAAAAATTTAGATGAGTGGGAAGATGATTTGTTAATGCG<br>ATATCCTGACCCTTCTGAAGTAAATGAAAGTTTAAAAGAAAAGCAGAAAGAAGAATTTAGAAAATTATGTCG<br>ATTCTGAAAGAGTAGAAACGGTAAAAGAATTTTACAGGATAAACCATACCTACCAAACTTATGACTTTGTA<br>TGCAGTAAAGAACAAGAATTTCTGCAATTTAATAGAAAAGAAATGTCAATCTGGGAAGCTGTCGAGTTTTT<br>AAACACGCTTGTAGACGACAGTGACCCAGATATTGACTTAGACCAGACACAGCACCTTTTACAGACTTCAG<br>AAGCCATTCGTGCTGATGGTCATCCGGATTGGTTTGTACTGACAGGTTTCATTCACGATTTGGGTAAAGTT<br>TTATGCTTATTTGGAGAACCGCAATGGGCAGTCGTTGGCGATACTTTTCCGGTTGGCTGTGCGTATTCGGA<br>TAAAATTGTGTATTCAGAATTTTTTAAAGAAAATCCGGATTATACAGATGAGAGATTCAATACTAAACTAG<br>GAATCTACACTGAAAACTGCGGATTAGATAACGTAAAAATGAGCTGGGGTCATGACGAATATTTGTATCAG<br>ATTATGAAAGATTATTTACCGGATCCTGCTTTATACATGATTCGTTATCACTCTTTTTATTCGCAGCATAA<br>AGAAAATGCGTATGCACATTTAATGAATGAAAAAGACATCGAAATGTTTGACTGGGTTCGAAAATTCAATC<br>CGTACGATTTGTATACAAAGGCTCCTGTAAAACCAGATGTTCAGGCATTACTTCCTTATTATAAAGAATTA<br>GTTGCTAAATATTTGCCTGAAAAATTGAAGTTTTAA<br>(SEQ ID NO: 17) |
| Mus musculus | ATGAAAGTGGATGTTGGCCCGGACCCGAGCCTGGTTTACCGCCCGGATGTGGACCCGGAAATGGCAAAAAG<br>CAAAGATTCGTTTCGTAACTACACCAGTGGCCCGCTGCTGGATCGTGTGTTTTTACCACGTATAAACTGATGC<br>ATACCCACCAGACGGTTGACTTTGTCAGCCGTAAACGCATTCAATATGGCGGTTTCTCTTACAAGAAAATG<br>ACCATCATGGAAGCGGTGGGCATGCTGGATGACCTGGTTGATGAATCAGATCCGGACGTCGATTTTCCGAA<br>TTCGTTTCATGCGTTCCAGACGGCCGAAGGTATTCGCAAAGCCCACCCGGACAAAGATTGGTTCCATCTGG<br>TCGGCCTGCTGCACGATCTGGGTAAAATCATGGCACTGTGGGGTGAACCGCAGTGGGCTGTGGTTGGTGAT<br>ACCTTTCCGGTGGGTTGCCGTCCGCAAGCAAGTGTCGTGTTTTGTGACTCCACCTTCCAGGACAACCCGGA<br>TCTGCAAGACCCCGCGCTATTCAACGGACTGGGCATGTACCAGCCGCATTGCGGTCTGGAAAACGTGCTGA<br>TGTCGTGGGGTCACGATGAATACCTGTACCAGATGATGAAATTCAACAAATTCAGCCTGCCGTCTGAAGCC<br>TTCTACATGATCCGTTTCCATAGTTTCTACCCGTGGCACACCGGCGGTGATTATCGCCAGCTGTGCTCCCA<br>GCAAGACCTGGATATGCTGCCGTGGGTGCAAGAATTCAACAAATTCGATCTGTACACGAAATGTCCGGATC<br>TGCCGGACGTTAATCTCTGCGTCCGTACTACCAAGGTCTGATTGATAAATACTGTCCGGGCACCCTGTCG<br>TGGTAA<br>(SEQ ID NO: 18) |

The invention claimed is:

1. A method of selecting a subset of microbes for the production of a metabolite comprising:
   (a) providing a population of microbes,
   wherein the population of microbes has been genetically modified to include exogenous DNA encoding for a reporter, the reporter being a fluorescent protein,
   wherein the population of microbes has been genetically modified to include exogenous DNA encoding a sensor biomolecule, wherein the sensor biomolecule is a transcription factor, which when expressed regulates expression of the reporter by the microbes,
   wherein the population of microbes has been genetically modified to include exogenous DNA encoding genes to produce a metabolite binding partner of the sensor, wherein the sensor biomolecule and the metabolite binding partner is a member pair selected from the group consisting of cdaR/glucaric acid, ttgR/naringennin, tetR/tetracycline derivates, benM/muconic acid, alkS/medium chain n-alkanes, xylR/xylose, araC/Arabinose, gntR/Gluconate, galS/Galactose, trpR/tryptophan, qacR/Berberine, rmrR/Phytoalexin, cymR/Cumate, melR/Melibiose, rafR/Raffinose, nahR/Salicylate, nocR/Nopaline, cicR/Chlorobenzoate, varR/Virginiamycin, PhoR/Phosphate, MalK/Malate, GlnK/Glutamine, Retinoic acid receptor/Retinoic acid, Estrogen receptor/Estrogen and Ecdysone receptor/Ecdysone, and
   wherein the microbes produce the metabolite binding partner which binds to the sensor to induce expression of the reporter in a manner dependent on the concentration of the produced metabolite, and
   (b) screening the population of microbes by detecting the reporter to identify a subset of microbes.

2. A method of selecting a subset of microbes for the production of a metabolite comprising:
   (a) providing a population of microbes,
   wherein the population of microbes has been genetically modified to include exogenous DNA encoding for a reporter, the reporter being a fluorescent protein, wherein the reporter is a member selected from the group consisting of mPlum, mCherry, tdTomato, mStrawberry, J-Red, mOrange, mKO, mCitrine, Venus, YPet, Emerald, CyPet, mCFPm, Cerulean, T-Sapphire, Firefly (FLuc), modified firefly (Ultra-Clo), Click beetle (CBLuc), Sea pansy (RLuc), Copepod crustacean (GLuc), and Ostracod crustacean (CLuc),
   wherein the population of microbes has been genetically modified to include exogenous DNA encoding a sensor biomolecule, wherein the sensor biomolecule is a transcription factor, which when expressed regulates expression of the reporter by the microbes,
   wherein the population of microbes has been genetically modified to include exogenous DNA encoding genes to produce a metabolite binding partner of the sensor, wherein the sensor biomolecule and the metabolite binding partner is a member pair selected from the group consisting of cdaR/glucaric acid, ttgR/naringennin, tetR/tetracycline derivates, benM/muconic acid, alkS/medium chain n-alkanes, xylR/xylose, araC/Arabinose, gntR/Gluconate, galS/Galactose, trpR/tryptophan, qacR/Berberine, rmrR/Phytoalexin, cymR/Cumate, melR/Melibiose, rafR/Raffinose, nahR/Salicylate, nocR/Nopaline, cicR/Chlorobenzoate, varR/Virginiamycin, PhoR/Phosphate, MalK/Malate, GlnK/Glutamine, Retinoic acid receptor/Retinoic acid, Estrogen receptor/Estrogen and Ecdysone receptor/Ecdysone, and
   wherein the microbes produce the metabolite binding partner which binds to the sensor to induce expression of the reporter in a manner dependent on the concentration of the produced metabolite, and
   (b) screening the population of microbes by detecting the reporter to identify a subset of microbes.

3. The method of claim 1, wherein the screening is carried out by fluorescence activated cell sorting, microscopy, microtiter plate assay, emulsion assay, microfluidic assay, pull-down assay or luciferase high throughput screening.

4. The method of claim 1, further comprising
genetically modifying the subset of microbes to alter genes that affect production of the metabolite directly or indirectly, and
screening the subset of microbes by detecting the reporter to identify a subsequent subset of microbes.

5. The method of claim 1, wherein the reporter is enhanced green fluorescent protein (EGFP).

6. The method of claim 1, wherein the screening further comprises selecting a subset of microbes that produce the metabolite based on detection of the reporter.

7. The method of claim 2, wherein the screening is carried out by fluorescence activated cell sorting, microscopy, microtiter plate assay, emulsion assay, microfluidic assay, pull-down assay or luciferase high throughput screening.

8. The method of claim 2, further comprising
genetically modifying the subset of microbes to alter genes that affect production of the metabolite directly or indirectly, and
screening the subset of microbes by detecting the reporter to identify a subsequent subset of microbes.

9. The method of claim 2, wherein the reporter is EGFP.

10. The method of claim 2, wherein the screening further comprises selecting a subset of microbes that produce the metabolite based on detection of the reporter.

\* \* \* \* \*

SEQUENCE LISTING

<160> NUMBER OF SEQ ID NOS: 18

<210> SEQ ID NO 1
<211> LENGTH: 26
<212> TYPE: DNA
<213> ORGANISM: Artificial

```
<220> FEATURE:
<223> OTHER INFORMATION: Binding site

<400> SEQUENCE: 1
tttaacttta agaaggagat atacat                                          26

<210> SEQ ID NO 2
<211> LENGTH: 20
<212> TYPE: DNA
<213> ORGANISM: Artificial
<220> FEATURE:
<223> OTHER INFORMATION: Promoter

<400> SEQUENCE: 2
gaaataagga ggtaatacaa                                                 20

<210> SEQ ID NO 3
<211> LENGTH: 50
<212> TYPE: DNA
<213> ORGANISM: Artificial
<220> FEATURE:
<223> OTHER INFORMATION: Promoter

<400> SEQUENCE: 3
gcttcacaac cgcacttgat ttaatagacc ataccgtcta ttatttctgg                 50

<210> SEQ ID NO 4
<211> LENGTH: 320
<212> TYPE: DNA
<213> ORGANISM: Artificial
<220> FEATURE:
<223> OTHER INFORMATION: Promoter

<400> SEQUENCE: 4
agaaaccaat tgtccatatt gcatcagaca ttgccgtcac tgcgtctttt actggctctt      60
ctcgctaacc caaccggtaa ccccgcttat taaaagcatt ctgtaacaaa gcgggaccaa     120
agccatgaca aaaacgcgta acaaaagtgt ctataatcac ggcagaaaag tccacattga     180
ttatttgcac ggcgtcacac tttgctatgc catagcattt ttatccataa gattagcgga     240
tcctacctga cgctttttat cgcaactctc tactgtttct ccatacccgc tttcatatct     300
ttcacttttt ttgggctaac                                                320

<210> SEQ ID NO 5
<211> LENGTH: 521
<212> TYPE: DNA
<213> ORGANISM: Artificial
<220> FEATURE:
<223> OTHER INFORMATION: Promoter

<400> SEQUENCE: 5
atgctgttga ttgacgccag tgagaacccg gaaccggaaa cggaatcaaa tccgtgggtc      60
gaacagtggg gcacgctgtt gtcctgatat gttcagcgag cggtaaatgt cgttttagcg     120
gtgctgaatc gaatcttttc aggcaaatgc agtaaaaaac tgcttcatag cgcggatttt     180
tactggcgtt tgcctggagt caagcgatcc atttcatact cttctttatt tcttcgtttt     240
aacccttcct ttcttgttct tgttttcatt tccgtgaagt ggattccacc gtccagggct     300
aatgccaaaa tcgggcctca ttgaacgcat taatgttgtg ttgttgcacg gtgagccgct     360
atggcgcgct tttatactg ctattgccag atataaacac gcgccgtatt cggcgaacga     420
cctataaaaa cggcaaaaaa caccctacgt cacctctgat ttcctggcga tgtcgcagtc     480
```

-continued cagagtgagc gtggctaacg cgaattttca ggagtgcaac a                521

<210> SEQ ID NO 6
<211> LENGTH: 52
<212> TYPE: DNA
<213> ORGANISM: Artificial
<220> FEATURE:
<223> OTHER INFORMATION: Promoter

<400> SEQUENCE: 6
ggattgaata taaccgacgt gactgttaca tttaggtggc taaacccgtc aa    52

<210> SEQ ID NO 7
<211> LENGTH: 91
<212> TYPE: DNA
<213> ORGANISM: Artificial
<220> FEATURE:
<223> OTHER INFORMATION: Promoter

<400> SEQUENCE: 7
tcgagtccct atcagtgata gagattgaca tccctatcag tgatagagat actgagcaca    60
tcagcaggac gcactgaccg aattcattaa a                                   91

<210> SEQ ID NO 8
<211> LENGTH: 51
<212> TYPE: DNA
<213> ORGANISM: Artificial
<220> FEATURE:
<223> OTHER INFORMATION: Promoter

<400> SEQUENCE: 8
cacccagcag tatttacaaa caaccatgaa tgtaagtata ttccttagca a    51

<210> SEQ ID NO 9
<211> LENGTH: 660
<212> TYPE: DNA
<213> ORGANISM: Artificial
<220> FEATURE:
<223> OTHER INFORMATION: Regulator

<400> SEQUENCE: 9
atgccgctga ccgacacccc gccgtctgtt ccgcagaaac cgcgtcgtgg tcgtccgcgt    60
ggtgctccgg acgcttctct ggctcaccag tctctgatcc gtgctggtct ggaacacctg    120
accgaaaaag gttactcttc tgttggtgtt gacgaaatcc tgaaagctgc tcgtgttccg    180
aaaggttctt tctaccacta cttccgtaac aaagctgact cggtctggc tctgatcgaa    240 gcttacgaca cctacttcgc tcgtctcctc gaccaggcgt tcctggacgg ttcgctggct    300
ccgctggctc gtctgcgtct gttcacccgt atggctgaag aaggtatggc tcgtcacggt    360
ttccgtcgtg gttgcctggt tggtaacctg ggtcaggaaa tgggtgctct gccggacgac    420
ttccgtgctg ctctgatcgg tgttctggaa acctggcagc gtcgtaccgc tcagctgttc    480
cgtgaagctc aggcttgcgg tgaactgtct gctgaccacg acccggacgc tctggctgaa    540 gcttttctgga tcggttggga aggtgctatc ctgcgtgcta aactggaact gcgtccggac    600
ccgctgcact ctttcacccg taccttcggt cgtcacttcg ttacccgtac caggaataa    660

<210> SEQ ID NO 10
<211> LENGTH: 879
<212> TYPE: DNA
<213> ORGANISM: Artificial
<220> FEATURE:
<223> OTHER INFORMATION: Regulator

<400> SEQUENCE: 10

```
atggctgaag cgcaaaatga tccccctgctg ccgggatact cgtttaacgc ccatctggtg    60
gcgggtttaa cgccgattga ggccaacggt tatctcgatt tttttatcga ccgaccgctg   120
ggaatgaaag gttatattct caatctcacc attcgcggtc agggggtggt gaaaaatcag   180
ggacgagaat ttgtctgccg accgggtgat attttgctgt tcccgccagg agagattcat   240
cactacggtc gtcatccgga ggctcgcgaa tggtatcacc agtgggttta ctttcgtccg   300
cgcgcctact ggcatgaatg gcttaactgg ccgtcaatat ttgccaatac gggtttcttt   360
cgcccggatg aagcgcacca gccgcatttc agcgacctgt ttgggcaaat cattaacgcc   420
gggcaagggg aagggcgcta ttcggagctg ctggcgataa atctgcttga gcaattgtta   480
ctgcggcgca tggaagcgat taacgagtcg ctccatccac cgatggataa tcgggtacgc   540
gaggcttgtc agtacatcag cgatcacctg gcagacagca ttttgatat cgccagcgtc    600
gcacagcatg tttgcttgtc gccgtcgcgt ctgtcacatc ttttccgcca gcagttaggg   660
attagcgtct taagctggcg cgaggaccaa cgcattagtc aggcgaagct gcttttgagc   720
actacccgga tgcctatcgc caccgtcggt cgcaatgttg ttttgacga tcaactctat    780
ttctcgcgag tatttaaaaa atgcaccggg gccagcccga gcgagtttcg tgccggttgt   840
gaagaaaaag tgaatgatgt agccgtcaag ttgtcataa                          879
```

<210> SEQ ID NO 11
<211> LENGTH: 1158
<212> TYPE: DNA
<213> ORGANISM: Artificial
<220> FEATURE:
<223> OTHER INFORMATION: Regulator

<400> SEQUENCE: 11

```
atggctggct ggcatcttga taccaaaatg gcgcaggata tcgtggcacg taccatgcgc    60
atcatcgata ccaatatcaa cgtaatggat gcccgtgggc gaattatcgg cagcggcgat   120
cgtgagcgta ttggtgaatt gcacgaaggt gcattgctgg tactttcaca gggacgagtc   180
gtcgatatcg atgacgcggt agcacgtcat ctgcacggtg tgcggcaggg gattaatcta   240
ccgttacggc tggaaggtga aattgtcggc gtaattggcc tgacaggtga accagagaat   300
ctgcgtaaat atgcgaact ggtctgcatg acggctgaaa tgatgctgga acagtcgcgg    360
ttgatgcact gttggcgca ggatagccgt ttgcgggaag aactggtgat gaacctgatt   420
caggcagagg agaatactcc cgcacttact gaatgggcgc aacggctggg gatcgatctc   480
aatcaaccgc gagtggtggc tattgttgag gtcgacagcg gtcagcttgg cgtggacagc   540
gcaatggcgg agtacaaca actgcaaaac gcgctgacta cgcccgagcg taataatctg    600
gtggcgattg tctcgctaac cgaaatggtg tgttgaaac cggcgttgaa ctcttttggg    660
cgctgggatg cagaagatca tcgtaagcga gttgaacaac tgattacccg catgaaagag   720
tacggccagc tgcgttttcg cgtttcactg gcaactatt ttaccggtcc tggcagtatt    780
gcccgatcct atcgtacggc gaaaacgacg atggtggtgg gtaaacagcg gatgccagaa   840
agtcgctgct attttatca ggatctgatg ttacctgtgt tactcgacag tttgcgtggc    900
gactggcagg ccaacgaact ggcgcgaccg ctggcgcggc tgaaaacgat ggacaataac   960
ggcttgctgc gacgaacgct ggcggcgtgg tttcgccaca atgtgcaacc gctggcaacg  1020
tcaaaggcgt tgtttattca tcgtaatacc ctggagtatc ggcttaatcg tatatcggaa  1080
```

```
ctgaccgggc ttgatttggg caattttgat gacaggttgc tgctgtatgt ggcgttacaa    1140
ctggatgaag agcggtag                                                  1158

<210> SEQ ID NO 12
<211> LENGTH: 585
<212> TYPE: DNA
<213> ORGANISM: Artificial
<220> FEATURE:
<223> OTHER INFORMATION: Regulator

<400> SEQUENCE: 12
atgccgcgtc cgaaactgaa atctgacgac gaagttctgg aagcggcgac cgttgttctg      60
aaacgttgcg gtccgatcga attcaccctg tctggtgttg cgaaagaagt tggtctgtct    120
cgtgcggcgc tgatccagcg tttcaccaac cgtgacaccc tgctggttcg tatgatggaa    180
cgtggtgttg aacaggttcg tcactacctg aacgcgatcc cgatcggtgc gggtccgcag    240
ggtctgtggg aattcctgca ggttctggtt cgttctatga cacccgtaa cgacttctct     300 gttaactacc tgatctcttg gtacgaactg caggttccgg aactgcgtac cctggcgatc    360
cagcgtaacc gtgcggttgt tgaaggtatc cgtaaacgtc tgccgccggg tgcgccggcg    420
gcggcggaac tgctgctgca ctctgttatc gcggtgcga ccatgcagtg ggcggttgac      480
ccggacggtg aactggcgga ccacgttctg gcgcagatcg cggcgatcct gtgcctgatg    540
ttcccggaac acgacgactt ccagctgctg caggcgcacg cgtaa                    585

<210> SEQ ID NO 13
<211> LENGTH: 624
<212> TYPE: DNA
<213> ORGANISM: Artificial
<220> FEATURE:
<223> OTHER INFORMATION: Regulator

<400> SEQUENCE: 13
atgtctcgtt tagataaaag taaagtgatt aacagcgcat tagagctgct taatgaggtc      60
ggaatcgaag gtttaacaac ccgtaaactc gcccagaagc taggtgtaga gcagcctaca    120
ttgtattggc atgtaaaaaa taagcgggct ttgctcgacg ccttagccat tgagatgtta    180
gataggcacc atactcactt ttgcccttta gaagggaaa gctggcaaga tttttttacgt     240 aataacgcta aaagttttag atgtgcttta ctaagtcatc gcgatggagc aaaagtacat    300
ttaggtacac ggcctacaga aaaacagtat gaaactctcg aaaatcaatt agccttttta    360
tgccaacaag ttttttcact agagaatgca ttatatgcac tcagcgcagt ggggcatttt    420
actttaggtt gcgtattgga agatcaagag catcaagtcg ctaaagaaga agggaaaca     480 cctactactg atagtatgcc gccattatta cgacaagcta tcgaattatt tgatcaccaa    540
ggtgcagagc cagccttctt attcggcctt gaattgatca tatgcggatt agaaaaacaa    600
cttaaatgtg aaagtgggtc ttaa                                           624

<210> SEQ ID NO 14
<211> LENGTH: 633
<212> TYPE: DNA
<213> ORGANISM: Artificial
<220> FEATURE:
<223> OTHER INFORMATION: Regulator

<400> SEQUENCE: 14
atggtgcgtc gcaccaaaga agaagcacag gaaacgcgtg cgcagattat cgaagcggcc      60
gaacgcgcgt tttataaacg tggtgtggca cgtaccacgc tggcagatat tgcagaactg    120
```

```
gcaggtgtta cccgcggtgc aatctactgg catttcaaca ataaagccga actggttcag    180
gcactgctgg attctctgca cgaaacgcat gatcacctgg cccgtgcaag cgaatctgaa    240
gatgaactgg acccgctggg ctgcatgcgc aaactgctgc tgcaggtgtt aacgaactg     300 gttctggatg cacgtacccg tcgcattaat gaaatcctgc atcacaaatg cgaatttacg    360
gatgatatgt gtgaaattcg tcagcagcgc cagagcgccg tgctggattg tcataaaggt    420
atcaccctgg cactggcaaa cgcagttcgt cgcggtcagc tgccgggtga actggatgtg    480
gaacgcgcag cggttgcgat gtttgcctat gtggatggcc tgattggtcg ttggctgctg    540
ctgccggata tgttgatct gctgggcgat gtggaaaaat gggttgatac cggtctggat    600
atgctgcgtc tgagcccggc gctgcgcaaa taa                                 633
```

<210> SEQ ID NO 15
<211> LENGTH: 1023
<212> TYPE: DNA
<213> ORGANISM: Artificial
<220> FEATURE:
<223> OTHER INFORMATION: MIOX variant
<400> SEQUENCE: 15

```
atggtaaaca aggtcggtaa atctactctc gataagagca caaacctaga taaatccaaa     60
gggaatatat tagagaaact agatgatgat atacttcatg tcaatagaat tcgaggctct    120
ttaactaaca aaactccaat caccaaaacc cattcgatag atgatgagct taaactagaa    180
gaacaatcag aaactgccgc cgatgaaaat tggcaaatag catcggaata ttataaaaac    240
atagacacga aggctttccg ccaatatgaa ttagcttgtg atagagtcaa acagttttat    300
gaagaacaac atgaaaaaca aaccgtggcg tataatattc aagcaagaat taatttcaaa    360
actaaaacaa gagcaagaat gacagtttgg gaaggactag agaaattaaa caaattgtta    420
gatgattctg atcccgacac cgaattgtca caaatagatc atgcattaca gacggcagaa    480
gctatacggc gagatgggaa accacgatgg tttcaattag ttgggttgat tcatgattta    540
gggaaattac tatattttt tgattctcgt ggtcaatggg atgtagtggg tgatactttc     600
cctgttggtt gtaaattcct gaaacggatt attttccctg atagttttaa aaataatcca    660
gatttcctaa atccattgta taataccaaa tatggcatat attcaaaaca ttgtggatta    720
gataaagtca tgttgagttg gggtcatgat gagtatatgt atcatgttgc gaaaaagaat    780
tcgacattac caccggaagc attggcaatg ataaggtatc attcattta tccttggcat    840 caagaattgg catatagtta tttaatggat gagcatgata aagagatgtt gaaagcagtc    900
aaagctttca attcctatga tttatattcc aagatagatc aacagtatga tgttgaagag    960
ttgaaaccat attacctaga gttgattgat gagttttcc caaataaagt aattgatttt   1020
taa                                                                 1023
```

<210> SEQ ID NO 16
<211> LENGTH: 978
<212> TYPE: DNA
<213> ORGANISM: Artificial
<220> FEATURE:
<223> OTHER INFORMATION: MIOX variant
<400> SEQUENCE: 16

```
atgagtcaga ccgtggaaaa cacgtttggc gaatttcgta actacaccga tagcaaattc     60
caggatcgtg tggaacgcac gtacaaagat atgcacatta accagaatct ggaatacgtt    120
```

```
acccagatga aagataaata cttcaaactg gatctgggta aatggatgt gtacgaagtt        180 ttcaaactgc tggaaaacgt tcatgatgaa agcgatccgg ataatgatct gccgcagatc        240
gaacacgcat atcagaccgc ggaagcctgc cagaacaaat tcctgaaatc tgatacggaa        300
ctgcgcgaaa atgcgctgat tcgtagtatc tttcgcgatc atgaatggca gagcattccg        360
aaaatctggc aggatttcta taccaaaaaa cagagtctgg gcaatctgta cagccatatt        420
aaagattggt cttggtttcc gctggttggc ttcgttcacg atctgggtaa atcatgacc        480 ctgccggaat atggtcagct gccgcagtgg agcaccgtgg gtgatacgta cccgattgcc        540
tgcccgtttg caagcgcgaa cgtgttttct caccgtgaat tgttaaaga ttctaaagat        600 tacaacaatt acaataccga agtgaaacg cattatggca atacgagaa aaaatgtggt        660 ttcgataacg tggatatgag cttcggtcac gatgaataca tctacaaagt tttcgaacag        720
ggcagcgata tcccgtatga aggtctgtac ctgctgcgct atcattcttt ctacccgtgg        780 cacacccgc agacgggcgg tcatgcgtat caggaactgg ccaacgaaaa agattggctg        840
ctgctgccgc tgctgaaagc ctttcagaaa gcggatctgt attctaaact gccggaactg        900
ccgccgaaag aagtgctgga gaaaaatac aaaagtctgc tggataaatg ggttccgaac        960
aagaaaatta actggtaa                                                     978
```

<210> SEQ ID NO 17
<211> LENGTH: 888
<212> TYPE: DNA
<213> ORGANISM: Artificial
<220> FEATURE:
<223> OTHER INFORMATION: MIOX variant

<400> SEQUENCE: 17

```
atgaaaaagc atatagacac agacaatccg ttgaaaaatt tagatgagtg ggaagatgat         60
ttgttaatgc gatatcctga cccttctgaa gtaaatgaaa gtttaaaaga aaagcagaaa        120
gaagaattta gaaattatgt cgattctgaa agagtagaaa cggtaaaaga attttacagg        180
ataaaccata cctaccaaac ttatgacttt gtatgcagta agaacaaga atttctgcaa        240 tttaatagaa agaaaatgtc aatctgggaa gctgtcgagt ttttaaacac gcttgtagac        300
gacagtgacc cagatattga cttagaccag acacagcacc ttttacagac ttcagaagcc        360
attcgtgctg atggtcatcc ggattggttt gtactgacag gtttcattca cgatttgggt        420
aaagttttat gcttatttgg agaaccgcaa tgggcagtcg ttggcgatac ttttccggtt        480
ggctgtgcgt attcggataa aattgtgtat tcagaatttt ttaaagaaaa tccggattat        540
acagatgaga gattcaatac taaactagga atctacactg aaaactgcgg attagataac        600
gtaaaaatga gctggggtca tgacgaatat ttgtatcaga ttatgaaaga ttatttaccg        660
gatcctgctt tatacatgat tcgttatcac tctttttatt cgcagcataa agaaaatgcg        720
tatgcacatt taatgaatga aaaagacatc gaaatgtttg actgggttcg aaaattcaat        780
ccgtacgatt tgtatacaaa ggctcctgta aaaccagatg ttcaggcatt acttccttat        840
tataaagaat tagttgctaa atatttgcct gaaaaattga gtttttaa                    888
```

<210> SEQ ID NO 18
<211> LENGTH: 858
<212> TYPE: DNA
<213> ORGANISM: Artificial
<220> FEATURE:
<223> OTHER INFORMATION: MIOX variant

<400> SEQUENCE: 18

```
atgaaagtgg atgttggccc ggacccgagc ctggtttacc gcccggatgt ggacccggaa    60
atggcaaaaa gcaaagattc gtttcgtaac tacaccagtg gcccgctgct ggatcgtgtt   120
tttaccacgt ataaactgat gcatacccac cagacggttg actttgtcag ccgtaaacgc   180
attcaatatg gcggtttctc ttacaagaaa atgaccatca tggaagcggt gggcatgctg   240
gatgacctgg ttgatgaatc agatccggac gtcgattttc cgaattcgtt tcatgcgttc   300
cagacggccg aaggtattcg caaagcccac ccggacaaag attggttcca tctggtcggc   360
ctgctgcacg atctgggtaa aatcatggca ctgtggggtg aaccgcagtg ggctgtggtt   420
ggtgatacct ttccggtggg ttgccgtccg caagcaagtg tcgtgttttg tgactccacc   480
ttccaggaca acccggatct gcaagacccg cgctattcaa cggaactggg catgtaccag   540
ccgcattgcg gtctggaaaa cgtgctgatg tcgtggggtc acgatgaata cctgtaccag   600
atgatgaaat tcaacaaatt cagcctgccg tctgaagcct tctacatgat ccgtttccat   660
agtttctacc cgtggcacac cggcggtgat tatcgccagc tgtgctccca gcaagacctg   720
gatatgctgc cgtgggtgca agaattcaac aaattcgatc tgtacacgaa atgtccggat   780
ctgccggacg ttgaatctct gcgtccgtac taccaaggtc tgattgataa atactgtccg   840
ggcaccctgt cgtggtaa                                                 858
```